United States Patent
Unger et al.

(10) Patent No.: US 8,652,424 B2
(45) Date of Patent: Feb. 18, 2014

(54) LABELS, CONTAINERS, SYSTEM AND METHOD FOR PROVIDING REAGENTS

(75) Inventors: Axel Unger, Munich (DE); Elgin Topfer, Munich (DE); Nicole Busch, Hamburg (DE); Tom Hynek, Munich (DE); Fredrik Aidehag, Munich (DE); Todd Pelman, Munich (DE); Martin Naley, Chevy Chase, MD (US)

(73) Assignee: Life Technologies Corporation, Carlsbad, CA (US)

( * ) Notice: Subject to any disclaimer, the term of this patent is extended or adjusted under 35 U.S.C. 154(b) by 1215 days.

(21) Appl. No.: 12/135,988

(22) Filed: Jun. 9, 2008

(65) Prior Publication Data

US 2009/0037293 A1    Feb. 5, 2009

Related U.S. Application Data

(63) Continuation of application No. 11/497,093, filed on Aug. 1, 2006, now Pat. No. 8,329,470.

(60) Provisional application No. 60/704,866, filed on Aug. 1, 2005.

(51) Int. Cl.
*B01L 3/00*    (2006.01)

(52) U.S. Cl.
USPC ......... 422/556; 422/547; 422/551; 435/288.1

(58) Field of Classification Search
USPC ............ 422/547, 551, 556; 435/287.1, 288.3, 435/288.1
See application file for complete search history.

(56) References Cited

U.S. PATENT DOCUMENTS

| 1,633,618 | A | 6/1927 | Thomas |
|---|---|---|---|
| D101,590 | S | 10/1936 | Patterson |
| D110,477 | S | 7/1938 | Carpenter |
| 2,135,239 | A | 11/1938 | Patterson |
| D124,054 | S | 12/1940 | Ansell |
| 2,560,761 | A | 7/1951 | Fergusion |
| 2,858,036 | A | 10/1958 | Earle et al. |
| 2,920,777 | A | 1/1960 | Cole |
| 3,033,375 | A | 5/1962 | Cole |
| D200,969 | S | 4/1965 | Wildgen |

(Continued)

FOREIGN PATENT DOCUMENTS

| EP | 0141104 | 5/1985 |
|---|---|---|
| EP | 0393174 | 6/1995 |

(Continued)

OTHER PUBLICATIONS

"Colour Coded lab bottle-caps", *Chemistry and industry* 06/200, 1.

(Continued)

*Primary Examiner* — Jill Warden
*Assistant Examiner* — Dwayne K Handy

(57) ABSTRACT

The invention relates to systems and methods for marketing and using products such as liquid materials, especially liquid reagents for use in microbiological and cellular biological laboratory settings include the use of unique color and simple numeric or alphanumeric identifiers to quickly and easily identify any product from a catalog list of products. Methods of marketing, advertising and producing such products are also disclosed. Particular embodiments include products, product packaging and product labeling. The invention also relates to collars and sleeves for containers, as well as related methods of use.

17 Claims, 41 Drawing Sheets

(56) References Cited

U.S. PATENT DOCUMENTS

| | | | |
|---|---|---|---|
| 3,449,210 | A | 6/1969 | Rohde |
| 3,702,806 | A | 11/1972 | Oliva |
| D234,042 | S | 1/1975 | Barton |
| D238,331 | S | 1/1976 | Meierhoefer |
| D247,092 | S | 1/1978 | Evangelista et al. |
| D264,127 | S | 4/1982 | Peterson |
| 4,534,483 | A | 8/1985 | Kassis et al. |
| 4,707,337 | A * | 11/1987 | Jeffs et al. ............... 422/525 |
| 4,770,854 | A | 9/1988 | Lyman |
| 4,851,351 | A | 7/1989 | Akamine |
| D302,658 | S | 8/1989 | Grinde |
| 4,858,776 | A | 8/1989 | Mehra |
| 4,935,371 | A | 6/1990 | Rickloff |
| D309,080 | S | 7/1990 | Buchholz |
| 5,002,199 | A | 3/1991 | Frahm |
| 5,011,032 | A | 4/1991 | Rollman |
| D328,431 | S | 8/1992 | Skidmore et al. |
| D337,863 | S | 7/1993 | Bowell |
| D343,093 | S | 1/1994 | Sabin et al. |
| D343,766 | S | 2/1994 | Bastidos |
| D347,554 | S | 6/1994 | Wingate et al. |
| D359,361 | S | 6/1995 | Swift et al. |
| 5,570,802 | A | 11/1996 | Wang et al. |
| D379,520 | S | 5/1997 | Stevens et al. |
| D379,521 | S | 5/1997 | Stevens et al. |
| 5,681,748 | A | 10/1997 | DiSorbo et al. |
| 5,693,537 | A | 12/1997 | Wilson et al. |
| 5,783,440 | A | 7/1998 | Stevens |
| 5,793,440 | A | 8/1998 | Nakasaka |
| 5,861,306 | A | 1/1999 | Pugh et al. |
| 5,924,583 | A | 7/1999 | Stevens et al. |
| 6,190,878 | B1 | 2/2001 | Pierson et al. |
| 6,210,959 | B1 | 4/2001 | Lodri et al. |
| 6,322,242 | B1 | 11/2001 | Lang et al. |
| D454,788 | S | 3/2002 | Pezzoli et al. |
| 6,508,801 | B1 | 1/2003 | Fineberg |
| 6,669,910 | B1 | 12/2003 | Bienhaus et al. |
| 6,818,438 | B2 | 11/2004 | Muser |
| D540,174 | S | 4/2007 | Lux |
| D548,612 | S | 8/2007 | Berman |
| D586,221 | S | 2/2009 | Shaikh |
| D586,656 | S | 2/2009 | Mount et al. |
| 2007/0031963 | A1 * | 2/2007 | Chang et al. ............... 435/304.3 |

FOREIGN PATENT DOCUMENTS

| | | |
|---|---|---|
| GB | 2007544 | 5/1979 |
| GB | 2027982 | 2/1980 |
| JP | 3051314 | 6/1998 |
| JP | 2002-297922 | 10/2002 |
| JP | 2005-110542 | 4/2005 |
| WO | WO-2007/016421 | 2/2007 |

OTHER PUBLICATIONS

Fisher Biotechnology Catalog, 1995, 248.
Fisher Catalog, May 2004, 201 & 242.
Food and Drug Packaging, May 2004.
2007016421, , "Subsequent International Search Report", WO-2007016421A2, Oct. 25, 2007.
Cox, R. P. et al., "Alkaline Phosphate Content and the Effects of Prednisolone on Mammalian Cells in Culture", *The Journal of General Physiology* 1962, 439-485.
International Search Report, and Written Opinion for PCT/US06/29584, Aug. 8, 2007.
Park, Paula, "A Better Bottle?", *The Scientist* Oct. 20, 2003, 33.
EP06800507.3, Extended European Search Report, mailed on May 6, 2010, 6 pgs.
EP09180494.8, Extended European Search Report, mailed on May 7, 2010, 6 pgs.

* cited by examiner

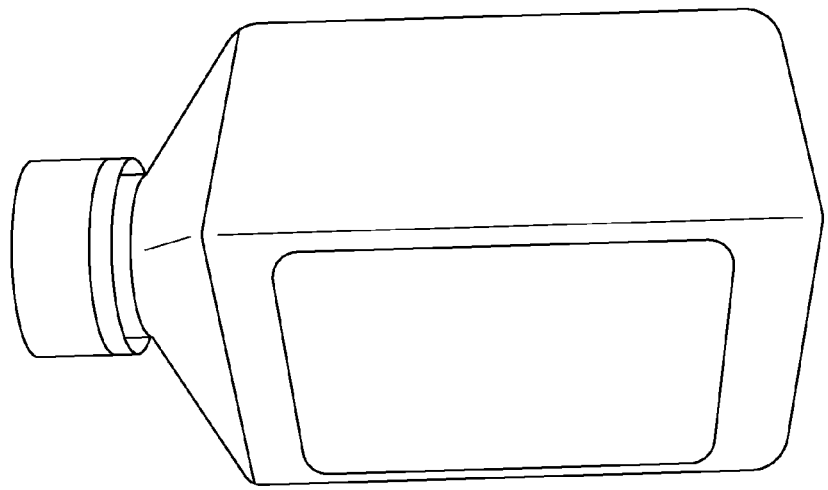
(PRIOR ART) *FIG. 2*
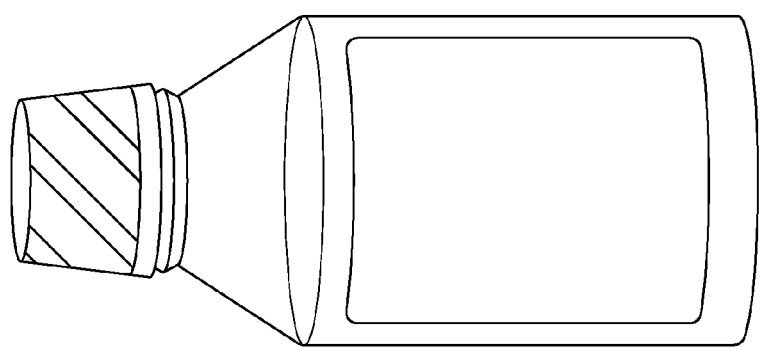
(PRIOR ART) *FIG. 1*

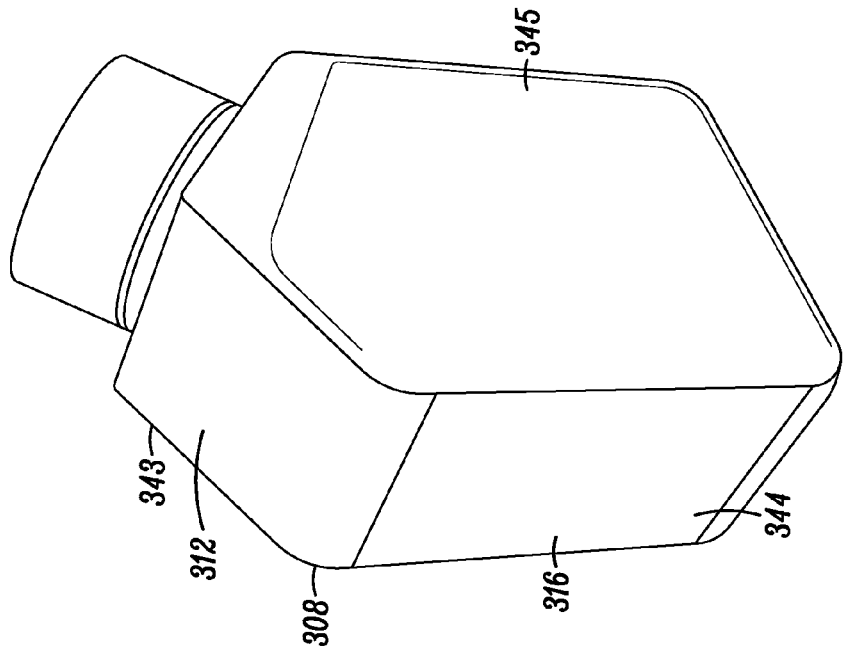
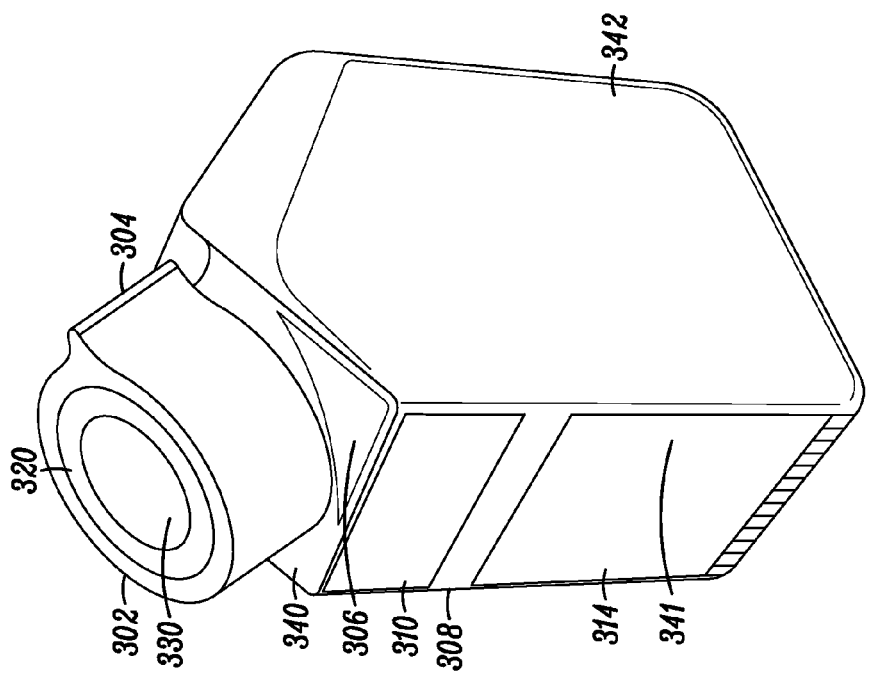
FIG. 9 BACK
FIG. 8 FRONT

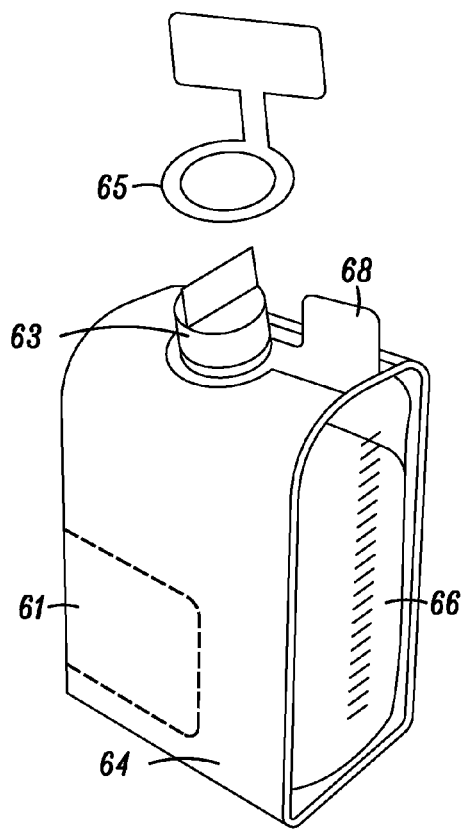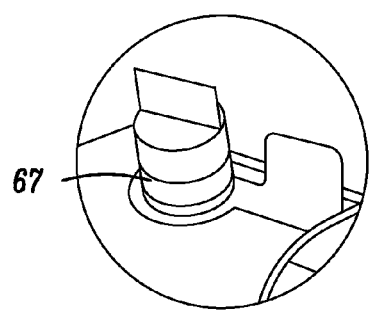
FIG. 13A
FIG. 13B

FRONT

BACK

LABELS, CONTAINERS, SYSTEM AND METHOD FOR PROVIDING REAGENTS

CROSS-REFERENCE TO RELATED APPLICATIONS

This application is a continuation of U.S. patent application Ser. No. 11/497,093, filed Aug. 1, 20006, which claims the benefit of U.S. Provisional Patent Application No. 60/704,866, filed Aug. 1, 2005, which disclosures are herein incorporated by reference.

STATEMENT REGARDING FEDERALLY SPONSORED RESEARCH OR DEVELOPMENT

N/A

BACKGROUND OF THE INVENTION

In the fields of molecular and cellular biology, particularly in a laboratory setting, it is of vital importance that the correct reagents and media are used in every instance, including use on the bench or in a sterile hood, and when selecting, ordering or re-ordering supplies. There are various factors that exist in a laboratory setting that can make this more difficult and less efficient. For example, bottles of media and sera are often stored in refrigerators where condensation may cause labels to be hard to read, and the important information may be small print that is easily obscured by moisture, user writing to label and identify additions, or other information about a particular bottle such as the user's initials, date opened, etc. Another difficulty is the manual dexterity required for sterile transfer of materials from a reagent or media bottle. Laboratory workers routinely wear protective gloves and must hold a pipette in one hand while also holding and opening a bottle, all while maintaining the sterility of the pipette, the cover and the contents of the bottle. Prior to the present disclosure, it has been difficult to quickly identify with assurance the contents of a particular bottle. This concern is of particular importance in the context of cell culture media bottles where mixing culture media types or solutions can have disastrous effects on research projects, greatly increasing the cost and time associated. Often, different types of media are indistinguishable by merely looking at the contents, requiring reading of small print, or re-orienting a bottle in order to positively identify the contents.

Although conventional labels often include the name of the product family in large type on the front of the bottle, it may be difficult to distinguish exactly what product is in the bottle, particularly if there are user annotations covering part of the label. For example, a certain label may identify the contents as a certain media, such as a basal media, but it may not be as clear that the content is basal media+glucose. Extra time and extra steps are needed, therefore, to determine exactly which product is being used, and to find a catalog number for re-ordering. Although a particular instance of wasted time might be small, they can collectively consume excessive amounts of time when one considers that within a single laboratory these actions may take place tens or even hundreds of times within a day.

In addition to difficulty in identifying the contents of a bottle, conventional bottles typically do not offer both storage efficiency and versatility. As all storage devices, refrigerators, incubators, freezers, shakers, stirrers, hoods, culture rooms, etc., do not have the same layout and dimensions, adaptability and versatility in the storage capabilities of bottles can be a significant problem. One type of conventional bottle is the round bottle shown in FIG. 1. This bottle shape results in inefficient use of space when stored, due to dead space between bottles and the inability to stably stack bottles on top of each other. Another type of conventional media bottle is a square bottle as shown in FIG. 2. Although these bottles can more efficiently abut other bottles both from the side and the front, they cannot be stored on a side and stacked on top of one another without the contents of the bottle coming in contact with the lid. Content contact with the lid can potentially cause leakage or contamination resulting in increased costs, lost research time, and a lack of supplies. Another disadvantage is that when the bottles are stored side by side in rows, only the labels of the front row can be seen without lifting the bottles to reveal a label. Furthermore, the caps are not easily accessible and the tops of the caps cannot be seen without lifting the bottle or looking directly down from above, which is not possible in many storage situations such as in a refrigerator. As all storage devices, refrigerators, incubators, freezers, shakers, stirrers, hoods, culture rooms, etc., do not have the same layout and dimensions, adaptability and versatility in the storage capabilities of bottles can be a major source of inefficiency.

Prior to this disclosure, there have been few or no attempts to solve these problems, especially in the fields of microbiology and cellular biology where conventional round and square media bottles are almost universally used. A mixing station for chemicals used in cleaning and maintenance supplies using a color coded system has been disclosed in U.S. Pat. No. 6,322,242. This patent discloses the use of various color coded elements, including caps, labels, valve members, and liquid outlet lines, to identify how the components should be assembled with respect to one another. This does not teach, however, a system of providing solid or liquid products that are appropriate or useful for microbiological or other research media, particularly to be used with sterile technique, and utilizing color coded covers or caps, corresponding color coded labels, or specially designed bottles to facilitate ease of identification of the contents of a bottle during storage, use, and re-supplying.

SUMMARY

The present disclosure is directed, in part, to compositions and methods related to labels and/or containers. These labels and/or containers may be used in a variety of manners, such as for identifying and containing materials. Further uses include various methods such as methods for storing and/or dispensing materials. Additional methods include those related to business (e.g., methods related to (1) simplification of ordering or re-ordering materials, (2) inducing, persuading or enticing potential customer or customers to order or re-order particular products, etc.).

In particular embodiments, containers of the invention may be composed of six or more (e.g., six, seven, eight, nine, ten, etc.) panels or sides. An exemplary container of the invention which contains seven panels is shown in FIGS. 8 and 9. Thus, in particular embodiments, the invention includes container with seven panels. The panels of such container may comprise:

(i) a front panel and back panel, each of which is square or rectangular in shape (e.g., a front panel and back panel having a height to width ratio of between about 1.0 to about 1.0 and about 5.0 to about 1.0, between about 1.0 to about 1.0 and about 4.0 to about 1.0, between about 1.0 to about 1.0 and about 3.5 to about 1.0, between about 1.0 to about 1.0 and about 3.0 to about 1.0, between about 1.0 to about 1.0 and about 2.5 to about 1.0, between about 1.0 to about 1.0 and about 2.0 to about 1.0, between about 1.0 to about 1.0 and about 1.5 to about 1.0, between about 1.5 to about 1.0 and about 5.0 to about 1.0, between about 2.0 to about 1.0 and about 5.0 to about 1.0, between about 2.5 to about 1.0 and about 5.0 to about 1.0, between about 3.0 to about 1.0 and about 5.0 to about 1.0, between about 3.5 to about 1.0 and about 5.0 to about 1.0, between about 4.0 to about 1.0 and about 5.0 to about 1.0, etc.);

(ii) two side panels (see, e.g., FIGS. 26A-26C) each having five edges, wherein two of the edges are vertical edges which are parallel to each other, wherein one of the edges is a horizontal edge that is located at the bottom of the panel, and two of the edges are angled, upper edges which each extend upward from different vertical edges and meet to form an upside down V;

(iii) a base panel which is square or rectangular in shape; and (iv) two angled, upper panels which are square or rectangular in shape;

wherein the above panels are referred to/identified with reference to the container resting on the base panel.

The total inner volume of containers described herein, such as a seven sided container as described above, will to a large extent be determined by the length, width, and height dimensions of the panels which form the container. Again using a container of the type shown in FIGS. 8 and 9 as an example, in many instances where the individual members within the two sets of parallel panels (e.g., (1) the side panels and (2) the front and back panels) are of the same overall dimensions, the total inner volume of the container will be determined, to a large extent by the lengths A, B, C, D, E, and/or I shown in FIGS. 26A-26C and FIG. 27. The length H being the height of the rectangular portion of the side panels. The length C being the width of the container. The length I being the depth of the container as defined by the width of an angled upper panel.

Shapes of containers described herein may be at least partially defined with reference to lengths A, C, and I shown in FIGS. 26A-26C and FIG. 27. The ratio of A:C:I may vary greatly. The ratio of A:C, A:I, and/or C:I, for example, can each independently be in the range of from about 0.25:1.0 to about 5.0:1.0, from about 0.5:1.0 to about 5.0:1.0, from about 0.75:1.0 to about 5.0:1.0, from about 1.0:1.0 to about 5.0:1.0, from about 1.5:1.0 to about 5.0:1.0, from about 2.0:1.0 to about 5.0:1.0, from about 2.5:1.0 to about 5.0:1.0, from about 3.0:1.0 to about 5.0:1.0, from about 3.5:1.0 to about 5.0:1.0, from about 4.0:1.0 to about 5.0:1.0, from about 1.0:1.0 to about 4.0:1.0, from about 1.0:1.0 to about 3.0:1.0, from about 1.0:1.0 to about 2.5:1.0, from about 1.0:1.0 to about 2.0:1.0, from about 1.5:1.0 to about 5.0:1.0, from about 1.5:1.0 to about 4.0:1.0, from about 1.5:1.0 to about 3.0:1.0, from about 1.5:1.0 to about 2.5:1.0, from about 2.0:1.0 to about 5.0:1.0, from about 2.0:1.0 to about 4.0:1.0, from about 2.0:1.0 to about 3.5:1.0, from about 2.0:1.0 to about 3.0:1.0, from about 2.5:1.0 to about 5.0:1.0, from about 3.0:1.0 to about 5.0:1.0, etc.

As one skilled in the art would recognize, if any one of lengths A, C, or I is small, with respect to one or both of the other lengths, the container may be unstable when placed on one or more panel. Thus, in many instances, consideration will be given to designing containers described herein which can be rested on a surface in a manner which minimizes the chance that the container will tip over after being contacted with a relatively small amount of kinetic energy (e.g., is bumped at low velocity, such as a velocity less than 0.5 inch/second, by a mass less than one half that of the container when empty).

As an example, when the ratio of A:C:I is 2.0:2.0:1.0, exemplary dimensions for A:C:I include 2 inches:2 inches; 1 inch and 6 inches:6 inches:3 inches. In such an instance, the A:C ratio may be referred to as 1.0:1.0, the A:I and C:I ratios may be referred to as 1.0:0.5.

Containers described above and elsewhere herein may further contain an opening in at least one of the angled, upper panels. Further, this opening may be designed to accept a cover, such as a cap or lid. Thus, the opening may contain a raised portion (see, e.g., FIGS. 27A and 27B, lengths F and G) which may be threaded.

Further, containers described herein may have an inner volume which varies considerably but include the ranges of from about 25 milliliters to about 1000 milliliters; from about 75 milliliters to about 500 milliliters; from about 125 milliliters to about 500 milliliters; from about 250 milliliters to about 1000 milliliters; from about 250 milliliters to about 500 milliliters; from about 5 milliliters to about 1000 milliliters; from about 5 milliliters to about 5000 milliliters; from about 25 milliliters to about 5000 milliliters; and from about 125 milliliters to about 5000 milliliters.

The present disclosure is directed, in part, to systems and methods of packaging, storing, using, and/or marketing of products. Such products include, for example, products for use in the biological sciences such as molecular biology and cellular biology, including but not limited to cell culture, stem cell culture, protein, nucleic acid and ribonucleic acid utilization and research, pharmaceuticals, and other industrial and academic laboratory research and production, as well as various compositions of matter. The disclosure and the invention are directed, in part, to labels and containers described herein and/or used in such methods. The invention provides, in part, improved and efficient packaging, labeling, storage, marketing and methods of use of such systems that provide benefits to the users and to the providers of such products and services. Certain advantages are provided by the individual components of the systems and methods disclosed herein and by the combination of any of these elements. As such, disclosed inventions herein include both the individual components and the combined components of the disclosure.

Although aspects of the invention are described herein as relating, for example, to various embodiments that include cell culture reagents including media and sera, other aspects of the invention are directed to other products, both solid and liquid that may be included in the described systems. For example, buffers, salts, salt solutions, nutrients, carbohydrates, carbohydrate solutions, proteins, protein solutions, amino acids, amino acid solutions, nucleic or ribonucleic acid solutions, vitamins, lipids, reagents, enzymes, growth factors, attachment factors, cytokines, antibiotics, mammalian cells, insect cells, dyes, acid solutions, base solutions, solvents, and other products known in the art as well as combinations of any of these can also be packaged and marketed within the scope of the present disclosure.

The disclosure may also be characterized in certain embodiments as storage and/or containment systems for solid or liquid material products, including scientific products or products for use in the biological arts, wherein the material products are marketed to a plurality of users, either through a catalog, for example, or through custom ordering. The disclosed systems can include containers for a plurality of materials, wherein a container includes a color code associated with a family of products or group of products and/or a number, alphabetic, alphanumeric, other character or a combination of these associated with a product within that family or group. In particular embodiments, products can be identified by a color and a short identifier; and further the color code and identifier can be prominently displayed on a container and/or any packaging material for ease of identification by a user. It is understood that the system can also include a number or an alphanumeric identifier or other indicator of four or more digits or characters, but it is an essence of the disclosure that the identifier has as few numbers and letters as is practical. The systems may thus be optimized by determining the number of characters that are easily retained by workers in biological laboratories on an empirical basis.

In certain embodiments, the disclosed systems can include containers having labels attached to one or more sides of the container and optionally wherein the container further includes a cover, or cap, and wherein the color and/or the identification code are prominently displayed on the labels on one or more sides of the container and also optionally prominently displayed on the cover, as well as on systems that include such containers. It is understood that common practice in the art is to produce labels separately from the containers and covers and then to affix labels to a container or cover with an adhesive, but the present disclosure is not so limited, and labels as described and disclosed herein may be partially or completely printed, painted, sprayed, dyed, or screened onto the surface, or embossed, extruded, mixed, or molded into the material of the container or cover itself. For example, the material of a cover or container may also be produced in a certain color in harmony with the color coding embodiments disclosed herein. The labels can also include color coded materials including but not limited to stickers, shrink wrap, tags, or tabs that are removable from a container or cover. It is a further aspect of the disclosure that in certain embodiments the removable items may be separately supplied to a user from a supplier such that certain aspects of the labels or covers may be provided separately and applied to a container by a user.

While the disclosure is described herein in terms of particular embodiments, it is evident to those of skill in the art that other configurations of containers may offer some or all of the same or like advantages and that all such containers usable in the described system fall within the spirit and scope of the present disclosure. For example, as described herein a container may be a bottle, jar, bag, drum, box, bucket or secondary packaging product or like container. The containers may be composed of any suitable material, depending on the contents to be contained and may comprise materials including, but not limited to glass, plastics, silicone, polymers such as high density polyethylene (HDPE), low density polyethylene (LDPE), polyethylene terephthalate (PET), glycol modified polyethylene terephthalate (PETG), polycarbonate (PC), polypropylene copolymer (PPCO), polypropylene (PP), fluorinated ethylene-propylene resin (FEP), perfluoralkoxy, (PFA), fluorinated high density polyethylene (FLPE), ethylene vinyl acetate (EVA), polyvinyl chloride (PVC), or stainless steel. Any of the containers can comprise multiple layers or coatings for a product contact layer, for example, wherein the coating or layer may comprise a silicone, silane or silicone or silane derivative, a gas impermeable layer or a tetrafluorethylene (Teflon®).

As such the disclosure can include containers of various shapes, sizes and capacities, and could include, but is not limited to a wedge type bottle having a generally triangular shape with rounded edges; a book-like bottle with a hinged, vertically opening cover, an angled access opening, and large flat surfaces for easy user labeling and annotation; a two chamber squeezable bottle with a large access opening and a screw-off upper chamber, such as one that transfers liquid from the bottom chamber into the top chamber through a central tube when squeezed; a cone shaped bottle designed to accept slip-on conical user labels, a two layer bottle with a soft, collapsible inner layer and a harder outer shell and comprising a prominent flap for user labeling; a wide-mouthed bottle with an angled body to allow for easy handling and label viewing; a slide-top bottle with a large top permitting a dual opening lid for pipetting and pouring; a flat, stackable bottle with large areas for user labeling or annotation and a low angled access opening for easy pipetting; a flexible top bottle, or a toggle top bottle with a slot in the handle that accepts an identification tag, and wherein the container comprises a label with a removable identification tag that is compatible with the slot in the handle; and the like.

In certain embodiments of the disclosure, particularly for containers for sterile liquids, the container may include flat surfaces on the front, rear, bottom, left and right sides, and a top providing an angled opening, such that the opening is visible and accessible when the container is standing on the bottom surface, lying on the front surface, or lying on the front surface with another container stacked on top of the container and lying on the rear surface thereof. Another aspect of the disclosure includes a container wherein the opening is covered by a cover, and wherein the top of the cover is accessible and viewable from a 45° angle above and in front of the container when the container is standing on the bottom surface, lying on the front surface, or lying on the front surface with another container of the same shape stacked on top of the container and lying on the rear surface thereof.

The invention also includes containers having one or more surface which "interplay" with one or more other surface (e.g., one or more surface of another container, a shelf, a counter top, etc.) In many instances, the interplay will be designed such that when the two surfaces are brought into close proximity or contact with each other, a container with one of the surfaces will exhibit an affinity for the item or items with the other surface. By "close proximity" is meant that two objects (e.g., protrusions) are within 0.1, 0.2, 0.4, 0.5, 0.7. 1.0, 2.0, 3.0, 4.0, or 5.0 millimeters of each other. While the interplay may be mediated by any number of means, the affinity may be, for example, physical (e.g., adhesive, interlocking, etc.) or electrical (e.g., magnetic, etc.). For example, in certain embodiments, the disclosed containers may include features which improve the stability or stacking stability of containers. In some instances, these features may improve a user's grip in laboratory conditions (e.g., under the hood or when a container has condensation or moisture on it), or provide ergonomic advantage. In certain embodiments, the features may be one or more textured regions, one or more coatings, or one or more indentation or protrusion on the front, rear, bottom, left, right sides, or top.

When indentations and/or protrusions are present, these features may be structured and/or positioned in any numbers of ways. Further, the number of indentations and/or protrusions, as well as other features of surfaces for interplay, may vary greatly. In particular, a surface of a container of the invention may contain one, two, three, four, five, six, seven, eight, nine, ten, twelve, fifteen, twenty, twenty-five, thirty, forty, fifty, sixty, seventy, eighty, ninety, etc. (e.g., from about 10 to about 100, from about 10 to about 20, from about 1 to about 4, from about 1 to about 6, from about 1 to about 10, from about 10 to about 30, from about 4 to about 10, from about 4 to about 15, from about 20 to about 100, from about 20 to about 30, from about 20 to about 40, from about 30 to about 60, etc.) indentations and/or protrusions. Some examples of indentations and protrusions are shown in FIGS. 29A-29C.

FIGS. 29A and 29B show protrusions 602 and 604 which, when present on opposing surfaces 601 and 603, will inhibit movement between the surfaces. This is so because the "squares" are positioned such that they will bump into each other if one surfaces moves in relation to the other surface. Numerous variations of these features may be employed, including those which comprise other geometric patterns, hooks, etc. Further, these features may be structures to function in a two dimensional manner (as exemplified in part by the features shown in FIGS. 29A and 29B and FIG. 29C, explained below) or three dimensionally as in the case of, for example hooks. Two dimensional interplay is advantageous, for example, in instances where sliding of the surfaces is sought to be prevented. In many instances, three dimensional interplay will be advantageous when it is desired, for example, to lock the surfaces together. This locking will often allow for the two surfaces to be moved as a single unit. Thus, the invention includes compositions and methods for locking two surfaces together and allowing for items (e.g., containers, etc.) with locked surfaces to be moved simultaneously without separating.

FIG. 29C shows indentations and protrusions 606 which when present on opposing surfaces 605 will contribute to stability of the surfaces with respect to inhibiting motion between the surfaces. Typically, one surface will contain indentations and the opposing surface will contain corresponding protrusions designed so that the protrusions settle into the indentations. Indentations and protrusions such as these, as well as others used in the practice of the invention, may be of any number, size and shape. Further, the total area of the surface on which they reside may vary greatly. As an example, the indentation and/or protrusion features shown in FIG. 29C may take up less than 5% of the total area of the surface on which they reside. However, such features may take up more than 5%, 10%, 20%, 30%, 40%, 50%, 60%, 70%, 80%, 90%, or 95% (e.g., from about 5% to about 20%, from about 10% to about 20%, from about 10% to about 30%, from about 10% to about 40%, from about 20% to about 50%, from about 50% to about 100%, etc.) of the surface on which they reside.

The indentations or protrusions may include, but are not limited to, complementary or interlocking surfaces (i.e., one or more indentation on a container to correspond with one or more protrusion on another container); one or more protrusion or "feet" on one or more sides of a container; a protruding rim along one or more outer edge of one or more sides of a container; indentations or protrusions to allow an area for attachment of anti-slip tabs or "feet" by a user; or one or more indentation or protrusion to create one or more textured region. The indentation(s), coating(s), or protrusion(s) may be printed, painted, sprayed, dyed, screened, or glued onto the surface of a container itself or embossed, extruded, mixed, or molded into a container, but are not so limited. For example, the material of the indentation(s) or protrusion(s) may be of the same material as a container or may comprise materials including, but not limited to plastics, silicone, epoxies, glues, foams, cork, rubbers, neoprene, or polymers. In addition to being embossed, extruded, mixed, or molded into a container or applied to a container by the manufacturer or supplier, the protrusion(s) or coating(s) may be supplied along with a container or as a separate item in the form of one or more glues, stickers, or tabs (such as hook and loop fasteners, rubber "feet," silicone "feet," cork tabs, or foam tabs), which may comprise materials including, but not limited to plastics, silicone, epoxies, glues, foams, cork, rubbers, neoprene, or polymers, for attachment by someone other than the manufacturer.

In certain embodiments the disclosed systems can include a package, such as a package for commercial sale, for example, wherein the package contains liquid cell culture media or sera. Such packages can include a container containing the liquid cell culture media or sera; the container can include a top, wherein the top can include an opening for access to the interior of the container, and wherein the opening can be disposed at an acute angle with respect to the front end. The acute angle may be from 10° to 80°, from 20° to 70°, from 20° to 60°, from 30° to 60°, from 40° to 50°, and in certain embodiments, approximately a 45° angle. The disclosed package may further comprise a cover, optionally configured to provide a sterile seal of the container, wherein the cover may be reversibly turned from a sealed configuration to an open configuration by a rotational movement of less than 360° (e.g., between from about 30° to about 360°, between from about 75° to about 360° between from about 90° to about 360° between from about 30° to about 270° between from about 90° to about 270°, between from about 30° to about 180°, between from about 90° to about 180°, etc.), less than 180° or even of approximately 90°. In certain embodiments, the container and cover alone or in combination provide a visual indication of the open or closed state of the cover. The disclosed containers may further include a labeling system wherein the cover includes a coded visual indicator of the contents of the container including a color and a code or indicator; and a label on the container in which the indicator and color are repeated, and in which the color and indicator are indicative of the contents of the container, and further can be indicative of a particular product.

The present disclosure also provides in part, a package for liquid cell culture media or sera including a container containing the liquid cell culture media or sera, the container including a cover, configured to provide a sterile seal of the container; a labeling system wherein the cover includes a coded visual indicator of the contents of the container including a color and a code or indicator; and a label on the container in which the code or indicator and color are repeated, and in which the color and code or indicator are indicative of the contents of the container.

As stated above, any of a number of solid or liquid products may be included as part of the present system and methods, and in certain embodiments the disclosed packages contain animal serum, or more specifically a package may contain bovine serum, heat inactivated bovine serum, donor bovine serum, donor bovine serum with iron, fetal bovine serum, US certified fetal bovine serum, US certified heat inactivated fetal bovine serum, dialyzed fetal bovine serum, ES cell qualified fetal bovine serum, Australia qualified fetal bovine serum, Canada qualified fetal bovine serum, New Zealand qualified fetal bovine serum, US qualified fetal bovine serum, non-US qualified fetal bovine serum, Australia qualified heat inactivated fetal bovine serum, Canada qualified heat inactivated fetal bovine serum, New Zealand qualified heat inactivated fetal bovine serum, US qualified heat inactivated fetal bovine serum, non-US qualified heat inactivated fetal bovine serum, ultra-low Ig fetal bovine serum, horse serum, heat inactivated horse serum, newborn bovine calf serum, heat inactivated newborn bovine calf serum, chicken serum, goat serum, lamb serum, porcine serum, rabbit serum, or other types of standard or custom serum known and used in the art.

In certain embodiments a package as disclosed may contain cell culture media, or it may contain base medium eagle (BME), BGJb medium, Brinster's BMOC-3 Medium, CMRL Medium, $CO_2$-Independent Medium, Cryopreservation Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM Zn++ Option (Richter's Modification), IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® Reduced Serum Media, RPMI Media 1640, Schneider's *Drosophila* Medium, Waymouth's MB 752/1 Media, Williams Media E, media formulated for amniotic fluid cells, media formulated for chorionic villus samples, media formulated for peripheral blood lymphocytes, media formulated for bone marrow cells or other types of standard or custom media known and used in the art.

In certain embodiments the disclosure is directed to packages or containers for and/or containing solid products. Such solid products may be powder or crystalline products for example, and may include dry powders, such as dry cell culture media products, or they may comprise a dry form of cell culture media in a granular format.

The present disclosure may be described therefore, in certain embodiments as a package for liquid products, such as products for use in the biological sciences and in certain embodiments, products such as cell culture media or sera. One exemplary embodiment of the disclosure includes a container that includes sides, such as a left side and a right side that are substantially planar and are disposed essentially parallel to each other; a front end surface and a rear end surface, wherein the two end surfaces are substantially planar and are disposed essentially parallel to each other; a planar bottom, adjoining and essentially perpendicular to the two sides and the two ends; a top, wherein the top includes an opening for access to the interior of the container, and wherein the opening is disposed at approximately a 45° angle with respect to the front end; and a cover, configured to provide a sterile seal of the container, wherein the cover may be reversibly turned from a sealed configuration to an open configuration by a rotational movement of less than 360°, less than 180° or even of approximately 90° and wherein the container and cover provide a visual indication of the open or closed state of the cover; a labeling system wherein the cover includes a coded visual indicator of the contents of the container where the coded indicator includes a color and a number; and a label on the container in which the number and color from the cover are repeated, and in which the color and number are indicative of the original contents of the container.

The disclosure may also be described in certain aspects as a method for marketing of solid or liquid material products, the method including providing to customers or potential customers information regarding the products wherein the products are listed in categories; and providing the products in containers, wherein each container includes a color code associated with a family of products and/or a number, code or other short identifier associated with a product within that family, wherein each individual product can be identified by a color followed by a one to three character designation in certain embodiments; and further wherein the color code and number or indicator may be prominently displayed on some or all of the containers for ease of identification by a user. In certain embodiments, a product group or family may be identified by a short identification code such as a number, letter, alphanumeric code or such a code that contains other characters, and members of the product family or group may be identified by individual colors.

In certain embodiments the disclosure may include methods for improving efficiency in a laboratory setting in which sterile materials including sterile liquids are transferred into and out of containers while maintaining the sterility of the transferred materials and of the materials remaining in the containers. These methods include providing sterile materials in containers that provide openings and covers to provide access and to seal the opening. Disclosed methods can include any of the following: providing openings in the containers that are oriented at an ergonomically advantageous angle for insertion of a pipette device. By ergonomically advantageous angle, Applicants intend the terms to have their standard meanings as used in the art, and the phrase is meant to convey that the containers provide an opening that allows for increased ease of use or efficiency of movement of a user accessing the container opening, such that the user can use fewer movements or movements over a decreased distance, or movements that are more comfortable and require less energy, or any combination of these when accessing the opening and withdrawing or adding contents from or to the container.

Another aspect of methods of increasing efficiency can be providing a cover that is openable with one hand, providing a cover that moves from an open to a closed position with a rotational movement of less than 360°, providing a cover that includes a visual indication that the cover is in the open or closed position, or any combination of these.

An additional aspect of methods of increasing efficiency can be providing optional protrusions or indentations that allow for increased stability of containers when stacked. The increased stability increases storage efficiency through encouraging stacking of containers in storage and in laboratory settings such as under the hood. Container stability also decreases the likelihood of spilling contents and increases efficient movements in laboratory settings such as repeated pipetting where containers are less likely to shift or slide. Thus, the invention further includes methods for decreasing spills and other errors. In some instances, these methods include those where such errors are decreased by at least 5%, 10%, 15%, 20%, 30%, 40%, 50%, 60%, 75%, 100%, 120%, 150%, etc. (e.g., from about 2% to about 20%, from about 5% to about 20%, from about 10% to about 20%, from about 2% to about 30%, from about 5% to about 30%, from about 30% to about 100%, from about 40% to about 150%, from about 50% to about 200%, etc.).

Yet another aspect of methods of increasing efficiency is providing one or more labels on a container that includes a prominent color code that identifies the type of product in the container and/or a one to three character designator in prominent type and optionally in the color of the color code. The aspect of the label that contains the color code and/or identifier may be on the container, on the cover, or both. The combination of the color and/or identifier is sufficient to identify the individual product within the product type so the product is easily identified. The efficiency may be further increased by providing a matching label on the cover that prominently displays the color code and/or the colored numerals or other identifier that match those on the container label.

In certain embodiments, the present disclosure is directed to methods of increasing efficiency by providing improved methods and components for material transfer, including transfer of liquid materials, and/or sterile liquids. An example of such an embodiment is shown in FIGS. 24A and 24B. Shown in FIGS. 24A&B is a container similar to containers shown in FIGS. 8-10. In the container shown, the cap has been removed and replaced with a dispenser or dispenser cap. A dispenser cap may be designed to be inserted into, or mate with any of the various openings of the containers or bottles disclosed herein. The dispenser may further be designed to contain a specific volume of liquid, and it may include graduated volume markings on one or more sides to aid in filling the dispenser to a desired volume, or to dispense a desired volume from the dispenser. In certain embodiments a dispenser is provided in a sterile package, such as a sterile plastic bag that may be opened just prior to use. In certain embodiments, a dispenser may be disposable and designed for a single use, or a dispenser may be autoclavable for multiple sterile uses.

In use, as shown in FIG. 24B, a desired amount of the contents of a bottle are transferred from the bottle into the dispenser. Transfer of the liquid may be active, by providing a bottle with flexible sides so that liquid can be squeezed into the dispenser, or liquid may be transferred from the container into the dispenser by gravity flow. In certain embodiments, a bottle or dispenser includes a trigger mechanism, such that a user activates a trigger in order to induce flow of liquid into the dispenser, and releases the trigger to stop the flow. In certain embodiments, the dispenser includes a valve, or a one-way valve effective to prevent backflow of liquid from the dispenser into the bottle, and to prevent additional flow of liquid from the container into the dispenser after the desired level is reached.

The bottle with attached dispenser may then be used to dispense a desired, measured amount of liquid media or other product. In certain embodiments, the dispenser may be used for a repeated process such that a desired amount of liquid can be dispensed multiple times as in feeding liquid media to a plurality of cultures. A dispenser may thus replace the need for pipetting in certain embodiments.

Examples of certain embodiments of dispensers are shown in FIGS. 25A and 25B. The embodiments shown include a work station or media station that may be used in conjunction with a dispenser as described herein. A media station as shown may include one or more bottle holders and a platform for tissue culture plates, for example, or other receptacles. In certain embodiments a user aligns a culture plate under a selected bottle, fills a dispenser attached to the bottle with a selected amount of fluid and then dispenses the fluid into a well in a culture plate. A station may contain an alignment device to align a cell culture plate or other receptacle under one or more bottle holders for dispensing a plurality of liquids. In certain embodiments, plates may be placed under a bottle manually, or either the bottle holders or the platform may move relative to each other to align a series of plates under one or more bottles for dispensing of one or more liquids to multiple cultures.

Increases in efficiency as disclosed herein can be determined by any form of measurement known in the art. Such measures include, but are not limited to a measure of error rate in ordering supplies, or a measure of error rate in adding supplies to a cell culture or other process. Increases in efficiency may also include numbers of cultures or other processes that are accomplished, or the amount of completed projects or experiments produced by a particular worker or by a group of workers, or any other indications of productivity within a particular setting.

Increase in efficiency can also be measured by survey of a representative group of workers within a particular setting. In certain embodiments the present disclosure includes, methods of increasing efficiency of laboratory workers, or laboratory output to levels between 1% and 10%, 1% and 20%, 1% and 30%, 1% and 40%, 1% and 60%, 1% and 80%, 1% and 100%, 10% and 20%, 10% and 40%, 10% and 50%, 10% and 70%, 10% and 85%, 10% and 100%, 30% and 60%, 30% and 80%, 30% and 100%, 40% and 60%, 40% and 80%, 40% and 100%, 50% and 70%, 50% and 90%, 50% and 100%, etc.

The disclosure may also be described in certain aspects as an improved method of providing products for use in a biological laboratory. In certain embodiments the method includes providing to users a description of products and services, either an electronic or paper and ink catalog of solid or liquid material products, for example, wherein the products are provided to users in storage containers or packages. In certain embodiments, containers include a color code associated with a family of products and an indicator as described herein associated with a product within that family, wherein each product can be identified by a color followed by an indicator. The color code and indicator can be prominently displayed on each container for ease of identification by a user. In practice, the improved method may include maintaining an electronic catalog on a computer system that is accessible by customers and in which at least some products are identifiable and searchable by the color code and numbers or other indicator.

As such, a customer may access the electronic catalog over an internet connection, for example, and search for a product by entering a color and number or indicator that appears on the label of a container that the customer is ordering. In certain embodiments a company or supplier maintains a web page in a web server. The opening or home web page can include information and/or links to information such as general company information, products, services, investor information, etc. and also can contain a link to one or more catalogs of products. In certain embodiments a catalog is accessible by any member of the public who has a computer connection to the internet. The host web page may also provide type boxes to allow a user to enter a user account name and password. Entry of an approved account name and password would link the approved user to a secure area of the server where ordering information can be entered.

In the secure area, a user can access account information such as purchase history, special pricing, or various subaccount information, etc. The user may also access one or more product or service descriptions such as catalogs, that can be searchable. A space can be provided for user input of search terms or an indicator for a product to be ordered. For example, a user may enter "Blue 29" if that color and number are an indicator for a desired product. The order for the product associated with Blue 29 would then be stored in a temporary memory, often referred to as a "shopping cart" while further orders are entered. A customer may also browse the product descriptions by keyword, or by product family. For example, a user may enter the term "Blue" into a search engine and would receive a page with all products in the family designated as "Blue." Each product listing can include product description, volume, and price, and would provide a tickbox for ordering a particular product, or a box for entering a number of pieces of that product to be added to the shopping cart.

Upon completion of the order, the user can be directed to checkout where billing information is entered or confirmed, including shipping address, purchase order number, or other information to complete the order. The website provides a button to submit the order that is selected and confirmed by the user. The order is then electronically forwarded to a database that is accessible by the shipping and billing departments for completion. One or more departments can also be notified by email or other means that an order has been received. The ordered materials are then pulled from inventory, packaged and shipped to the user, either with an invoice included in the package, or an invoice can be sent by separate cover. The described system is exemplary only, and the disclosed embodiments are not limited to electronic ordering. The ordering process can also be accomplished by telephone to an order department in which the customers relay the color code and identifier to a customer service representative who then relays the order within the supplier organization, or the customer may submit an order by mail or facsimile. Orders may also be made over a telephone line or wireless connection such as a satellite connection, or wireless telephone connection in which a user can exchange visual or text information with a company representative or a company computer.

In certain embodiments the present disclosure can include a system for online marketing of solid or liquid reagents or products to a plurality of users. The disclosed system can include a server computer configured to provide the electronic interface with users' computers. Such computers optionally include a central processing unit, software storage media and software effective to provide a user-interactive graphical user interface (GUI). It is understood that the server computer may be a single computer or a network of one or more computers that serve various functions. The computer also may include an electronic connection to a source of pricing information for various items offered for sale to users. This connection may be over a telephone line, a wireless satellite receiver, through an internet or intranet connection or by any other means known in the art. The computer also optionally includes a storage medium for storing a user preference database, a firewall to limit access to certain areas of the server to only authorized users, and an electronic connection to a network accessible to user computers.

In certain embodiments, the server is a web server and the users connect to the server through the world wide web, or internet, including wireless connections. It is also understood that other network connections may also be used including those known in the art and those to be developed. As such, the user's computer may be a desk top or portable computer, such as a laptop computer, a personal digital assistant, a telephone device or any other device that allows the user to interactively connect to the electronic interface.

An example of a computerized system is shown in diagram form in FIG. 21. The system includes a server computer 400 connected to a database storage medium 420. The server also includes a firewall 430 to prevent access by unauthorized users. The server is connected to a network 440 to which a plurality of user computers 450 may connect.

As used herein, a catalog is an ordered list of items, often with a description of each or of some items, that may be a printed paper listing or an electronic listing stored on a disc or other electronic media and accessed by computer, either locally or remotely. The items in a catalog are often grouped by family or subject matter, and each item is often associated with an individual product number or alphanumeric designation so that the catalog number identifies a specific item from the catalog and can be used to order that specific item. Some catalogs, such as those for suppliers of chemical and biological products have a large number of items, and catalog numbers may include 6-8 digits or even more and might include alphabetic designation, dashes, and other indicators. Such numbers are difficult to remember, are often displayed on a product in small type that may be difficult to read, and also increase the likelihood that an error may occur in using such a number to order or re-order product from a catalog.

As used herein, the term "prominent" as applied to prominent displays of information or color code is meant to indicate that the prominent display is in high contrast with the background, that it is conspicuous, pronounced, or noticeable, and that in the case of type, that the size of the type or the color would be readable and the color recognizable from a distance of three feet or more by a person with normal vision.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1 is a perspective view of a prior art rounded bottle.

FIG. 2 is a perspective view of a prior art rectangular bottle.

FIG. 8 is a front perspective view of a stackable rectangular container.

FIG. 9 is a rear perspective view of the container of FIG. 8.

FIG. 13A is a perspective view of a hard container with a soft, collapsible inner container.

FIG. 13B is a perspective view of the cover of the container of FIG. 13A.

FIGS. 29A and 29B show front views of raised features which, when on surfaces which are brought together, inhibit motion between the surfaces.

FIGS. 33A, 33B, and 33C show three views (i.e., two side and one bottom, respectively) of an exemplary container of the invention. 1029 indicates the location of a recycle symbol on the container.

DETAILED DESCRIPTION

The present disclosure is directed, in part, to compositions and methods related to labels and/or containers. In one aspect, the invention includes labels (e.g., labels for containers). These labels may be designed, for example, with one or more of the following features: (a) one or more rapidly identifiable visual cue which distinguishes the label from other labels; (b) one or more color code and/or one or more designation (e.g., a symbol, a number, a letter, etc.) or collection of designations which allow for identification of the label; (c) one or more spaces (e.g., spaces which alone or collectively take up greater than 25%, 35%, 45%, 55%, 65%, 75%, 80%, etc. of the total label) which are suitable for marking using, for example, a writing implement such as a magic marker (e.g., a felt tipped marker, etc.), a pen, a pencil, etc.; (d) one or more adhesive coated side which may be used, for example, to attach the label to a container or other item; (e) composed in a manner and/or of materials which allow the label to be durable under usage conditions (e.g., may be autoclaved, is resistant to organic solvent such as benzene and alcohols, like methanol and ethanol, isopropanol, etc.); (f) contains a feature which allows for visual identification of the history of the label (e.g., contains an indicator that changes when the label has been autoclaved); (g) suitable for application to flat surfaces; (h) suitable for application to a rounded and/or curved surface; and (i) allows for "brand recognition" (e.g., contains trademark such as "Invitrogen", "GIBCO", etc.). Thus, the invention includes labels, containers which contain labels, and methods employing such labels and containers. Additional features of labels of the invention and methods employing such labels are set out elsewhere herein.

Figure 10:
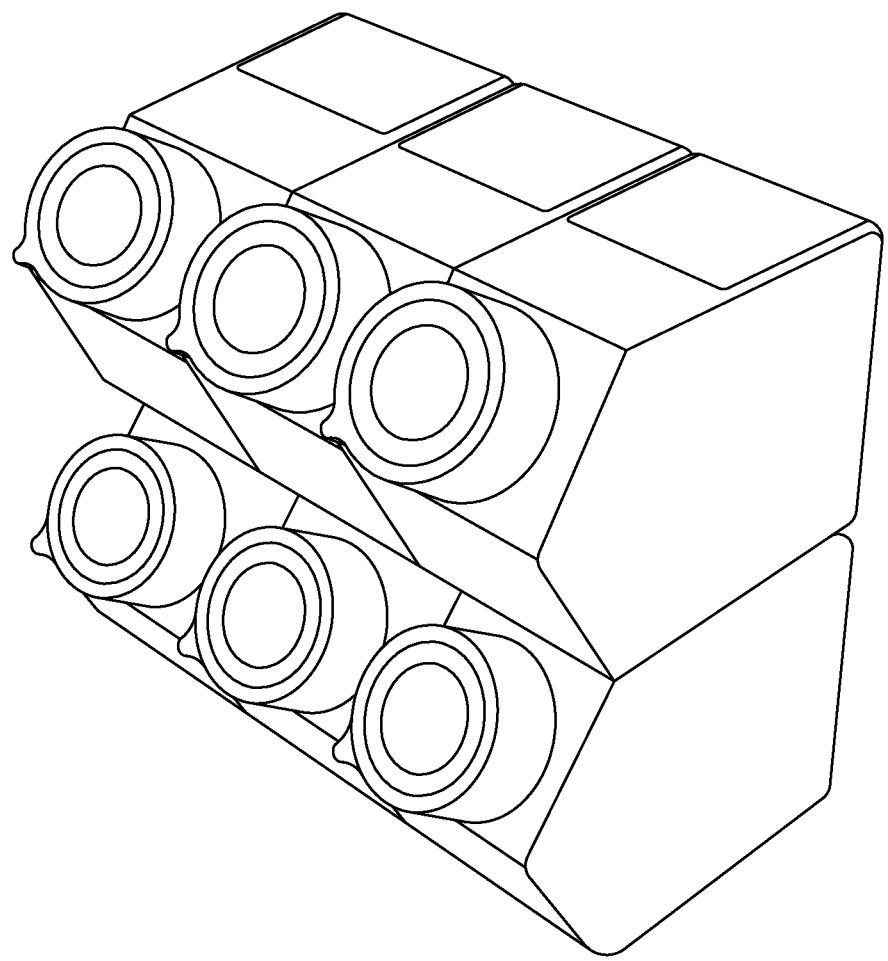
FIG. 10 is a perspective view of a stack of containers as shown in FIG. 8.

The disclosure further includes containers (e.g., containers designed to contain reagents). These containers may be designed, for example, with one or more of the following features: (a) a shape which allows for the container to be stored in a variety of positions without the contents either (i) spilling or falling out of an orifice (e.g., an opening for adding and removing container contents) or (ii) contacting a cover on the orifice of (i) (e.g., a "cap," "cover" or a "lid"), when and if the cover is present; (b) a shape which allows for container to be stored with other containers in a manner which allows for efficient usage of space (e.g., a shape which allows for stacking and/or placement of multiple containers with little or no space between them); (c) a label (e.g., a label of the invention as described elsewhere herein); (d) an orifice; and (e) a cover (e.g., a cap or a lid) over orifice. Specific aspects of the disclosure are shown in FIGS. 8-10. Thus, as noted above, the disclosure includes containers (e.g., containers with labels), and methods employing such containers. Additional features of containers and methods employing labels are set out elsewhere herein.

The disclosure also relates, in part, to systems and methods for improving laboratory efficiency, and systems and methods for marketing and supplying liquid or other materials such as cell growth media and sera to the microbiological and cellular biology industries and research facilities. In certain embodiments the disclosure includes systems for storage, transport, marketing, use and ordering of solid or liquid reagents and products that include, but are not limited to improved containers or bottles that may include instantly readable and recognizable labels and covers designed to increase efficiency through ease of identification, ease and adaptability of storage, ease of reordering, and greater bottle stability. In certain embodiments the disclosed systems are designed to decrease error rates and contamination through ease of identification and the concomitant decrease in handling of sterile bottles and generally to facilitate identification of the contents of the bottles. In certain embodiments the systems employ a series of improved bottles and labeling of the bottles and covers that provide an instant recognition of the contents of the bottle and the information necessary to identify the contents and to order, reorder or re-supply when necessary.

The Labels

One aspect of the disclosure is embodied in labels disclosed herein. The labels may be designed to increase efficiency and/or decrease error rates by simplifying the reordering process and enhancing product recognition. Labels can contain several different types of informative features, and these features can be arranged on the labels in a variety of ways. In certain embodiments, the user is able to quickly and easily identify the contents of a bottle by looking at the label, add personalized notations to the bottle or cover, reorder products using product information encoded on the labels, and/or read critical product information from the label. Color coding of the labels allows, for example, identification of the contents of the bottle without requiring the user to handle the bottle. Similarly, product number or other designation for reordering and critical product information may be readily ascertainable from the label at arm's length for a person with normal vision. Some examples of labels and features described herein are shown in the drawings of the containers in FIGS. 3-18.

Labels may be partially or completely printed on a separate media and attached or affixed to the bottles and or covers by adhesives or other means, or they may be painted, printed or dyed directly on the container and/or cover or the container may be produced with a portion of the label embossed on the surface, or included in the material of the container. It is a further aspect of the disclosure that labels for the containers and for the covers may be provided independently of the containers and may be affixed to containers by a user, or used independently of the containers. Labels may also be provided in conjunction with labeled containers and covers. For example, small labels containing various information may be attached to a package or packed with a container to use to designate storage space to a particular type of product or to stick in a catalog or lab notebook as a reminder of the color and number code for a particular product.

Various embodiments of labels that may be used within the system include, but are not limited to: embodiments in which two label sections of an opaque, translucent, or transparent material, or any combination thereof are used, one section for the front of the bottle and one section for the back of the bottle, leaving the bottom, top, and some portion of the sides of the bottle uncovered; embodiments having one continuous section of an opaque, translucent, or transparent material, or any combination thereof, that wraps around the entire circumference of a bottle, leaving some portion of the bottle above, and/or below the label uncovered; embodiments having one continuous section of an opaque, translucent, or transparent material, or any combination thereof, that wraps around the entire bottle leaving only some portion of the bottom and the cover and bottle interaction region uncovered; embodiments having one continuous section of an opaque, translucent, or transparent material, or any combination thereof, which wraps around the entire bottle and leaves only the cover and bottle interaction region uncovered; embodiments in which the entire bottle and cover are covered with perforation between the bottle and cover to allow opening of the bottle without substantially altering or removing the label; and embodiments having one or more sections on the bottle of an opaque, translucent, or transparent material, or any combination thereof, with uncovered regions for content viewing in any orientation.

Figure 3B:
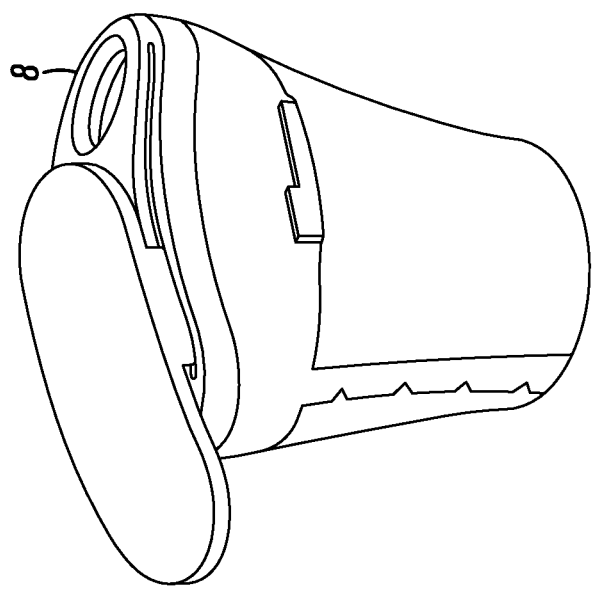
FIG. 3B is a perspective view of a slide top container with the top open in a different orientation.
Figure 3A:
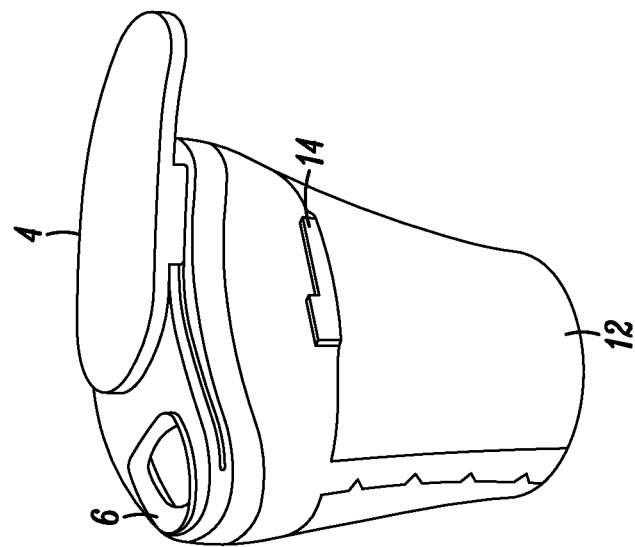
FIG. 3A is a perspective view of a slide top container with the top open.
Figure 5:
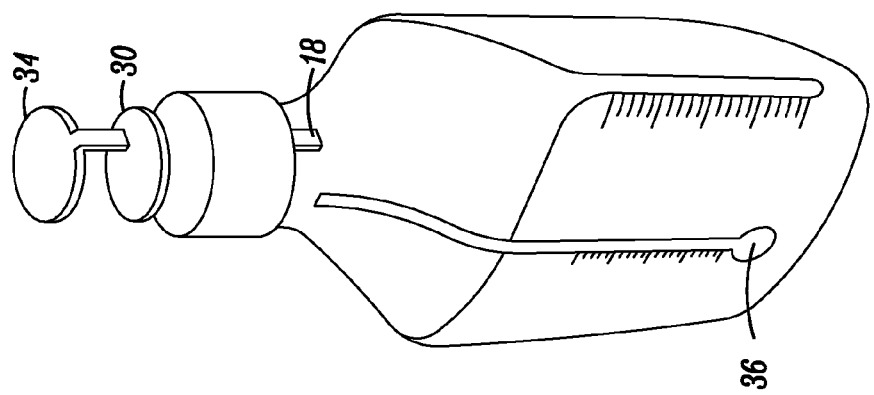
FIG. 5 is a perspective view of a wedge shaped container.
Figure 4:
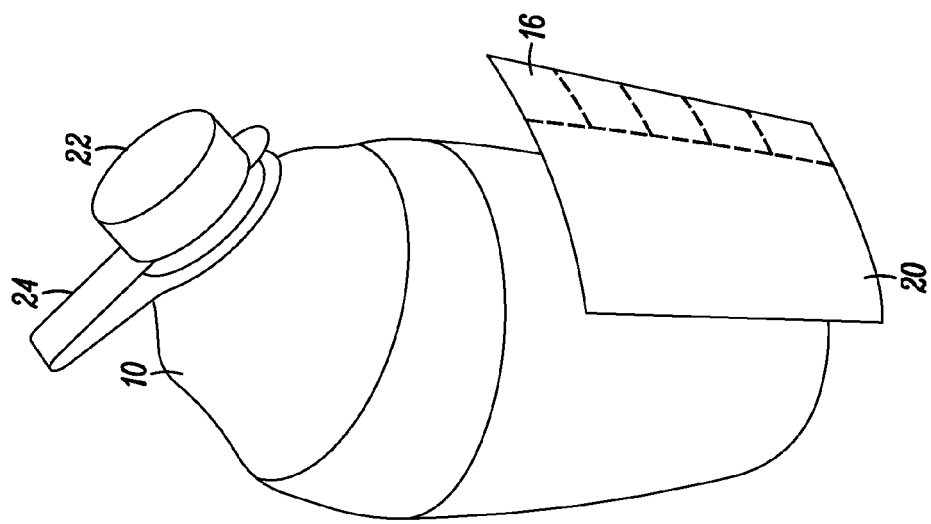
FIG. 4 is a perspective view of a flexible top container.
Figure 6:
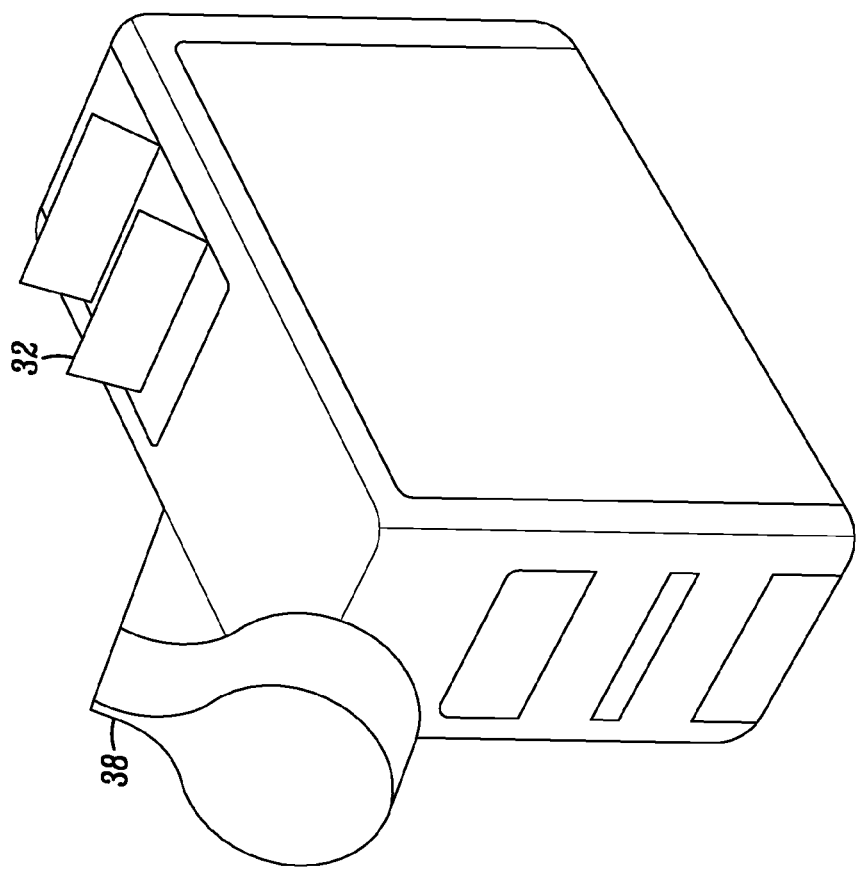
FIG. 6 is a perspective view of a box shaped container.
Figure 7:
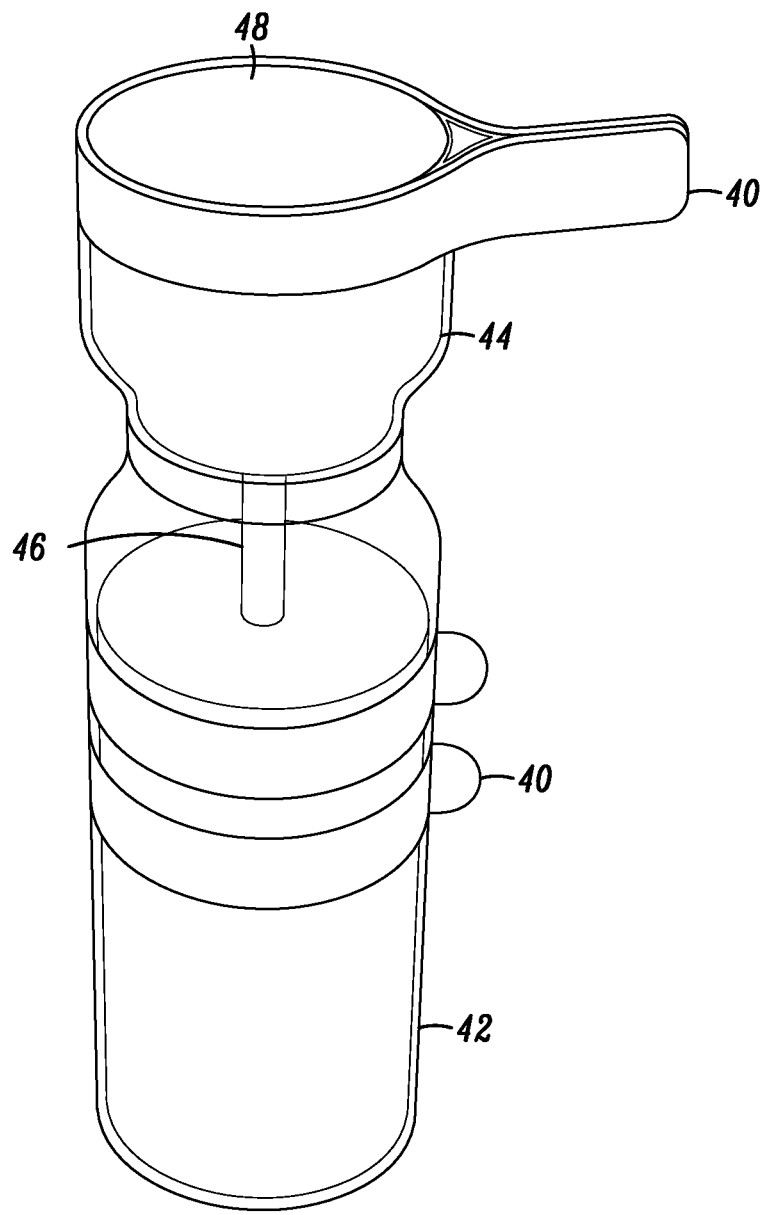
FIG. 7 is a perspective view of a two chambered container.
Figure 15:
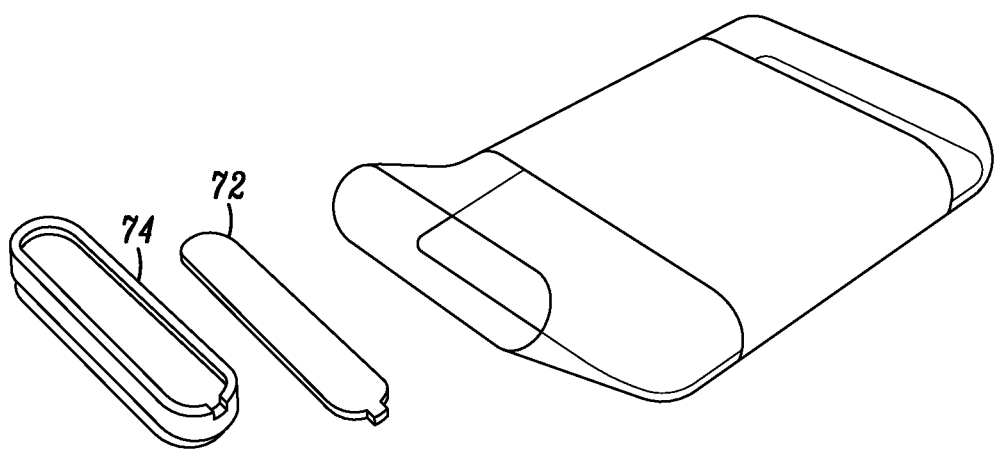
FIG. 15 is a perspective view of a flat container.

Any of the described embodiments of label may additionally include on either the front or the back of the bottle or both, any, all, or none of the following features: one or more color coded regions that match the color coding of the cover, cap or lid; printed information appearing horizontally or vertically, or in combination, on the label; a visible product identifier, that may use any combination of letters, numbers, symbols, and pictures, that indicates the contents of the bottle, such as a one to three digit (e.g., one to eight, one to five, two, to ten, etc.) number or alphanumeric characters in the color coded color; a large multi-layered, detachable and transferable, or permanently affixed, blank color coded section that matches the color coding of the cover, used for annotating and personalizing the bottle and facilitating information transfer to other bottles if detachable, which may or may not have one or more user information prompts printed on it, which may include but are not limited to "Name", "Date Opened", and "Additions"; a large multi-layered, detachable and transferable, or permanently affixed, partially or wholly lined color coded section that co-ordinates with the color coding of the cover, used for annotating and personalizing the bottle and facilitating information transfer to other bottles, which may or may not have one or more user information prompts printed on it, which may include but are not limited to "Name", "Date Opened", and "Additions"; a large multi-layered, detachable and transferable, or permanently affixed, blank white or light colored section used for annotating and personalizing the bottle and facilitating information transfer to other bottles if detachable, which may or may not have one or more user information prompts printed on it, which may include but are not limited to "Name", "Date Opened", and "Additions"; a large multi-layered, detachable and transferable, or permanently affixed, partially or wholly lined white or light colored section used for annotating and personalizing the bottle and facilitating information transfer to other bottles, which may or may not have one or more user information prompts printed on it, which may include but are not limited to "Name", "Date Opened", and "Additions"; a region listing specific product details in a contrasting color with respect to the region, which may include, but are not limited to, glucose content, protein content, various salt contents, buffer content, nutrient mixture, degree of filtration, lot number, catalog number, and case reorder number; one or more regions which may contain the product identifier, critical product information, which may include but is not limited to temperature range, light sensitivity, expiration date, and volume and may be expressed using letters, numbers, symbols, or pictures, and a descriptive product name displayed in a contrasting color with respect to the surrounding region; one or more color coded regions that match the color coding of the cover which may contain any, all, or none of the above features and information; a region listing specific product details in a contrasting color with respect to the region, which may include but are not limited to glucose content, protein content, various salt and buffer content, nutrient mixture, degree of filtration, lot number, catalog number, case reorder number; detailed product warnings; an expandable pocket 12 in which paper 14 may be placed, see FIG. 3A; a scannable bar code; detachable sections 16 with barcode, product reorder, and a lot-numbers printed on them, see FIG. 4; removable, adhesive sections, which can be used as seals or tamper indicators, see FIG. 5; removable sections which reveal additional information underneath 20; fold out sections 16 containing additional annotation space and specific product details, see FIG. 4; attached pull-up or removable identification, annotation, and indicator tags 32, see FIG. 6; removable identification and information transfer sections 30, 40, 72, for example see FIGS. 5, 7, & 15; decorative elements; and one or more trademarks, company names, or logos.

It is an aspect of the present disclosure that labels provide required information in an easily accessible format so that a symbol that is easy to recognize and to remember is used to identify a particular product. As such, in certain embodiments the label on a container contains an area or stripe that is color coded. This area may be a stripe or area that is clearly visible from the front, rear, either or both sides, or front and rear and/or either or both sides of the container. The color coded area may also include a more major portion or all of a label affixed to one or more sides of a container, or it may be a shrink wrap that covers all or part of the container or the cover. As such, a color coded area of a label may include up to 1%, 5%, 10%, 20%, 30%, 40% 50%, 60%, 70%, 80%, 90%, or even 100% (e.g., from about 5% to about 100%, from about 10% to about 100%, from about 20% to about 100%, from about 30% to about 100%, from about 40% to about 100%, from about 50% to about 100%, from about 60% to about 100%, from about 70% to about 100%, from about 80% to about 100%, from about 5% to about 80%, from about 10% to about 80%, from about 20% to about 80%, from about 30% to about 80%, from about 40% to about 80%, from about 50% to about 80%, from about 60% to about 80%, etc.) of one or more labels on one or more surfaces of a container. In particular embodiments labels also contain an identifier of either one digit, two digits, or three characters, of any combination of letters, numbers or other characters to designate a particular product when used in conjunction with a color. The indicator is optionally printed in the color coded region of a label or in another region of the label, either white or in contrast to the coded color, in which the number or alphanumeric designator is printed in the coded color. Labels as described may be affixed to or printed on the containers or on the cover, (cap or lid, for example).

It is a further aspect of the present disclosure that the labels on various containers of the disclosure provide space for user annotation without obscuring the color code and product identifier. As such, one or more labels of a container and/or a cover may provide blank space for user annotation. A label that is affixed to one or more faces of a container may, therefore provide equal, greater than or up to 5%, 10%, 20%, 30%, 40% 50%, 60%, 70%, 80%, 90%, or even 100% (e.g., from about 5% to about 100%, from about 10% to about 100%, from about 20% to about 100%, from about 300% to about 100%, from about 40% to about 100%, from about 50% to about 100%, from about 60% to about 100%, from about 70% to about 100%, from about 80% to about 100%, from about 5% to about 80%, from about 10% to about 80%, from about 20% to about 80%, from about 30% to about 80%, from about 40% to about 80%, from about 50% to about 80%, from about 60% to about 80%, etc.) blank or unused space for use annotation. The blank space is optionally white, but may be of any color that provides contrast for writing added by a user. It is a further aspect that the top of the cover may also provide the color code and number to identify a particular product and may further provide blank space for user annotation. As such, the covers can be composed of white material, or any other color that provides contrast for writing added by a user, that is easily annotated by a SHARPIE® or other felt tipped marker.

Figure 28:
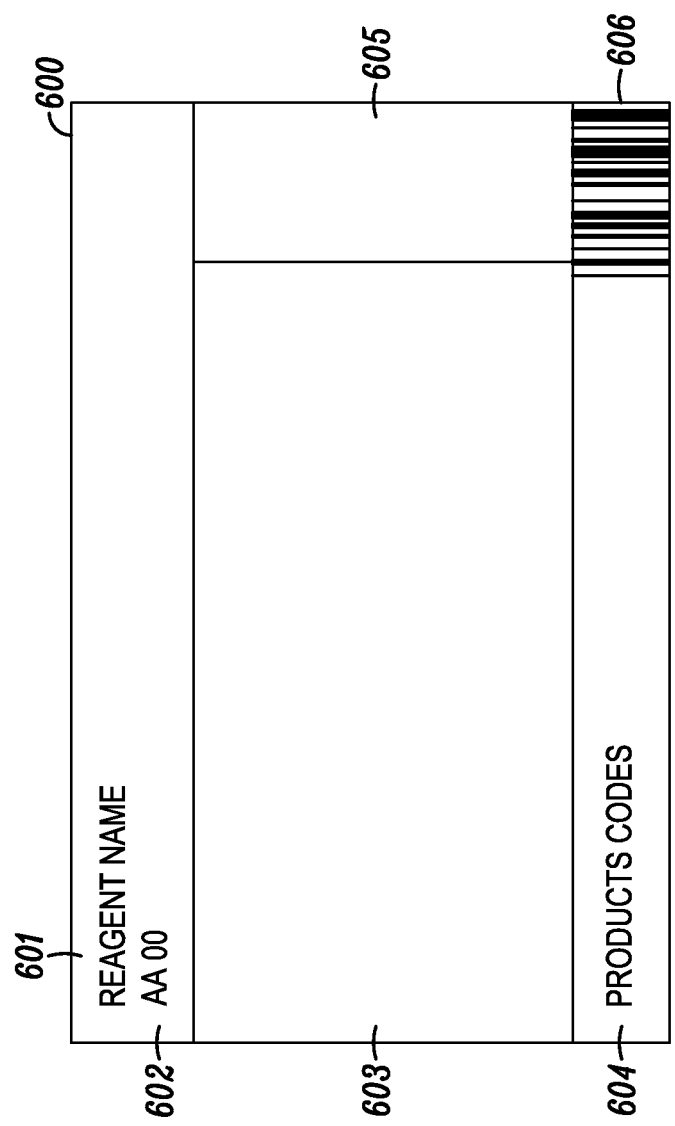
FIG. 28 shows an exemplary label of the invention.
Figure 29A:
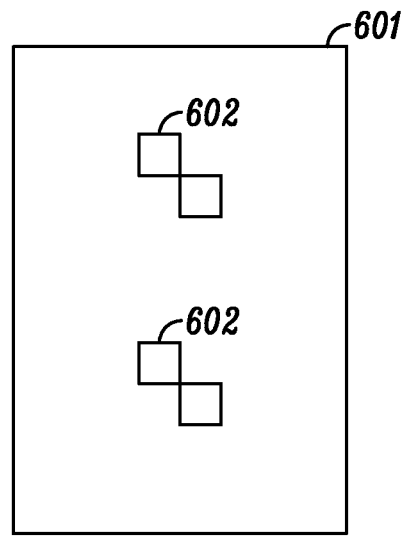
FIGS. 29A, 29B, and 29C show various aspects of features which allow for interplay between surfaces.
Figure 29B:
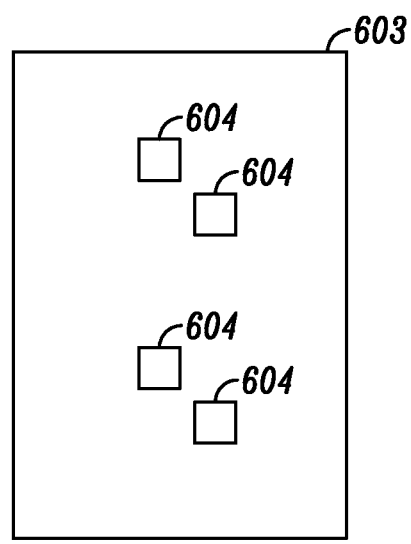
Figure 29C:
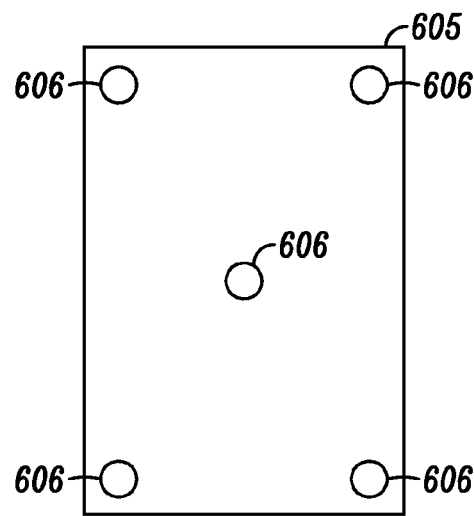

One exemplary label of the invention is shown in FIG. 28. This label contains a field 600 which contain the name of the reagent 601, and a reagent designation 602. One or more or all of the ingredients of the compound contained in a container labeled with this label may also be present in field 600 or one or more other fields shown in FIG. 28. The reagent designation may be any combination of characters such as letters, numbers and/or symbols. Further, the reagent designation may vary with an item's size. For example, "AA 00" may represent a 250 milliliter D-MEM product and "AA 01" may represent a 500 milliliter D-MEM product.

Field 600 in FIG. 28 is of a color which corresponds to the product (e.g., the contents of the container). Other fields may also be of a color which identifies the product and/or contents of the container.

Field 603 is space for marking on the label. This space will typically be of a color or visual density which allows markings (e.g., written information made with a black marker) to be readily visualized. In many instances, field 603 will be white.

Field 605 in FIG. 28 may contain various information and/or symbols which indicate information such as boiling point, freezing point, storage conditions, vapor pressure, hazard information (e.g., tetragenic activity), volatility, solubility, clean up or remediation conditions, photosensitivity, etc.

Field 604 may contain product codes such as catalog number or other product identifier, lot number and/or a re-order designation.

Field 606 contains a bar code for rapid identification of the product.

The field locations, sizes and contents shown in FIG. 28 are merely exemplary. Thus, the invention include labels, for example, in which these fields are located in different places on the labels.

Labels described herein, such as labels containing one or more feature shown in FIG. 28 may be used in various aspects of the invention.

Collars and Sleeves

A further aspect of the invention includes "collars" or "sleeves" which may be designed to attach to or around one or more of the following: cap, neck, shoulder, or body of a container, as well as containers which contain such collars and/or sleeves. In certain embodiments, the disclosed systems can include (a) containers having one or more collar attached to, provided with, or offered separately from a container, (b) containers having one or more sleeve attached to, provided with, or offered separately from a container; or (c) containers having one or more collar and one or more sleeve attached to, provided with, or offered separately from a container. The collars or sleeves may be designed, for example, with one or more of the following features: (a) one or more shape (e.g., open conical, open cylindrical, open pyramidal, etc.) that allows for ease of recognition, identification of contents, or attachment to or fitted attachment around a container; (b) sizes, colors, designs, layouts, or styles that allow for attachment to or around a container (i.e., allowing for application from the top, side, and/or bottom), ease of recognition and identification of contents, or conveyance of information; (c) one or more adhesive side or area which allows for reuse, removal, transferability and/or attachment to containers, lab notebooks, or storage areas; (d) one or more materials (including but not limited to plastics, corrugated plastic, cellulose, plasticized cards, foams, rubbers, latex, and laminated paper) which allow for reuse, removal, transferability, attachment to or around a container, utility in or out of water, and/or utility at different storage temperatures (including but not limited to 37° C., 25° C., 4° C., −20° C., and −80° C.) (i.e., to insulate a user from temperature extremes, such as removing a container from temperatures such as −20° C. or −80° C.), and/or replaceable writing surfaces (i.e., one or more transparent area that allows for viewing writing below and one or more opaque area allowing for user annotation); or (e) means of attaching to or around a container (including but not limited to plastic, glue, string, or wire).

Collars and sleeves are not limited to those which are readily applied to containers described herein. As can be seen with respect to the collar shown in FIG. 30, collars and sleeves of the invention may be applied to any type of container, including containers used in biological laboratories such as those described in U.S. Pat. Nos. Des. 379,521, 4,534,483, 5,783,440, 5,924,583, 6,210,959, and 6,818,438, the entire disclosures of which are incorporated herein by reference.

Collars and sleeves may be designed to serve practical applications such as advertising (e.g., product promotion, etc.) or user utility. Examples of user utilities include (a) provision of writing space, (b) marking of container contents with information such as safety data lot identification and other information described herein.

Collars and sleeves may also be transparent, opaque, or have some regions which are transparent and other regions which are opaque. In some instances, the positioning of transparent and opaque areas may be such that, when the collar or sleeve is applied to a container, the transparent area or areas will be located over information on a label and the opaque area or areas will be located over one or both of an unlabelled area or areas or a labeled area or areas. Advantages of using a sleeve on a container include (a) provision additional space for writing and (b) replacing space for writing (e.g., covering spaces that have been written on with unwritten space).

Collars or sleeves of the invention may be designed, for example, with one or more of the following features: (a) one or more rapidly identifiable visual cue which distinguishes the collar or sleeve from other collars or sleeves; (b) one or more color code and/or one or more designation (e.g., a symbol, a number, a letter, etc.) or collection of designations which allow for identification of the collar or sleeve; (c) one or more spaces (e.g., spaces which alone or collectively take up greater than 25%, 35%, 45%, 55%, 65%, 75%, 80%, etc. of the total collar or sleeve) which are suitable for marking using, for example, a writing implement such as a magic marker, a pen, a pencil, etc.; (d) one or more adhesive coated side which may be used, for example, to attach the collar or sleeve to a container or other item; (e) composed in a manner and/or of materials which allow the collar or sleeve to be durable under usage conditions (e.g., may be autoclaved, is resistant to organic solvent such as benzene and alcohols, like methanol and ethanol, isopropanol, etc.); (f) contains a feature which allows for visual identification of the history of the collar or sleeve (e.g., contains an indicator that changes when the collar or sleeve had been autoclaved); (g) suitable for application to flat surfaces; (h) suitable for application to a rounded and/or curved surface; and (i) allows for "brand recognition" (e.g., contains trademark such as "Invitrogen", "GIBCO", etc.).

Collars and/or sleeves of the invention may be attached or applied to a container on or before sales of the container (e.g., may be attached by the manufacturer) or may be offered separately for a user to attach to various containers, and may be attached in a temporary, semi-permanent, or permanent manner. In certain embodiments, one or more (e.g., one, two, three, four, five, etc.) collar or sleeve which may be attached in a temporary or semi-permanent manner may be offered separately, provided with, or attached to a container as product packaging by the provider (e.g., to convey advertising, promotion material or other information to users; allow for user personalization or annotation; allow for ease of removal or transferability of the information; or allow for ease of reordering).

Collars and sleeves may be applied to containers in any number of ways. As examples, these items may be applied from the top, side or bottom. Further, collars and sleeves may be in their final shape before application or may form their final shape after application. As an example of the later, a collar or sleeve may be designed to wrap around a container. In a specific embodiment, a sleeve, for example, may contain an adhesive area which, when wrapped a round a container, adheres to itself and/or the container.

Additionally, one or more collar or sleeve that may be attached in a permanent manner may be offered separately, provided with, or attached to a container as product packaging by the provider (e.g., the distributor or manufacturer). The provider may convey advertising or other information to users or provide blank or formatted areas for user personalization or annotation on the collars or sleeves. For example, the provider may incorporate one or more color in a collar or sleeve to aid in recognition of the contents of a container that is not in the front row of a storage area or that is a distance of one, two, three, four, etc. feet away or more by a person with normal vision. The visibility, of course, will vary with a number of aspects such as the size of the collar or sleeve, the color or colors of the collar or sleeve, the area of the collar or sleeve which contains the color or colors, the amount of the collar or sleeve visible under the particular conditions, the amount of light present in the particular situation.

In many instances, containers of the invention will be viewed from the top. Collars and/or sleeves may thus be designed so that they are visible when the upper portion of the container is visible (e.g., at least the top 5%, 10%, 15%, 20%, 25% can be seen). The invention thus includes, in part, collars and sleeves which are designed to attach to the upper portion of containers, as well as containers which have such collars and sleeves, method for applying such collars and sleeves to containers, and methods for providing containers which contain such collars and sleeves, as well as methods for providing the collars and sleeves themselves.

A portion of the collar or sleeve may contain a pre-formatted area (which may include, but is not limited to, "Name", "Date Opened", and "Additions") or a blank or lined area to allow for user annotation. Additionally, all or a portion of the collar or sleeve (e.g., portions which alone or collectively take up greater than 25%, 35%, 45%, 55%, 65%, 75%, 80%, etc. of the total collar or sleeve) may have adhesive side(s) to allow use as a sticker in other situations, such as transferal to another container, transferal to a laboratory notebook, or designation of storage space. For example, one or more portion of the collar or sleeve may be a transparent material that allows for viewing of writing underneath the collar or sleeve while other portions of the collar or sleeve may be an opaque area that obscures writing underneath and allows for user annotation when necessary (e.g., simply when additional writing space is needed or when new writing space is needed due to prior annotations being illegible, incorrect, or outdated).

Figure 30:
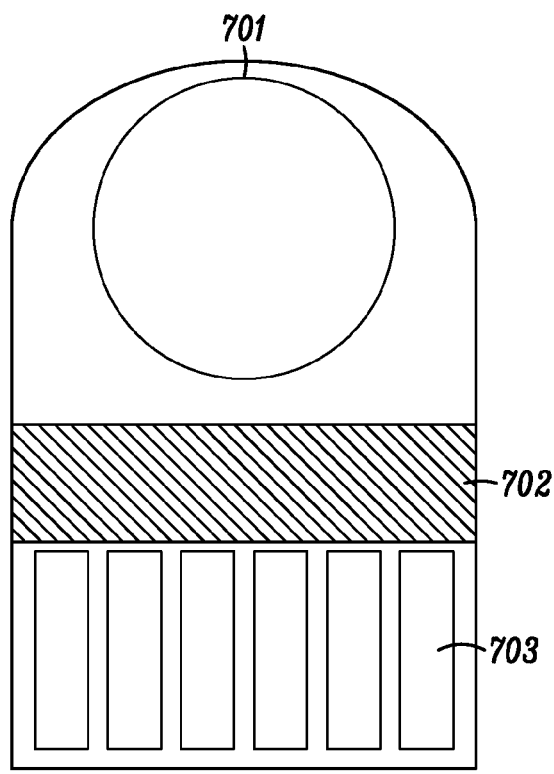
FIG. 30 shows an exemplary collar of the invention.

An example of a collar of the invention is shown in FIG. 30. FIG. 30 shows an embodiment of the invention with an opening 701 designed to fit over a round cap, an adhesive area 702 designed to adhere to a portion of the container upon which it is placed, and six removable tabs 703. The adhesive area 702 will typically be located on the back side of the collar. Further, the front portion of this area 702 will often be available for writing on or may contain identifying information of the collar and for the container to which it is applied.

Removable tabs, may be designed such that they will also adhere to other items to which they are applied (e.g., a laboratory notebook, etc.). Further, the removable tabs 703 may contain preprinted information and/or may be suitable for writing upon. Of course, similar features may be present in sleeves or labels of the invention. Also, features described herein for collars, labels and sleeves may be used in each of these items as appropriate. In other words, as an example, a feature described herein for a label may also be a feature of a sleeve.

Figure 31A:
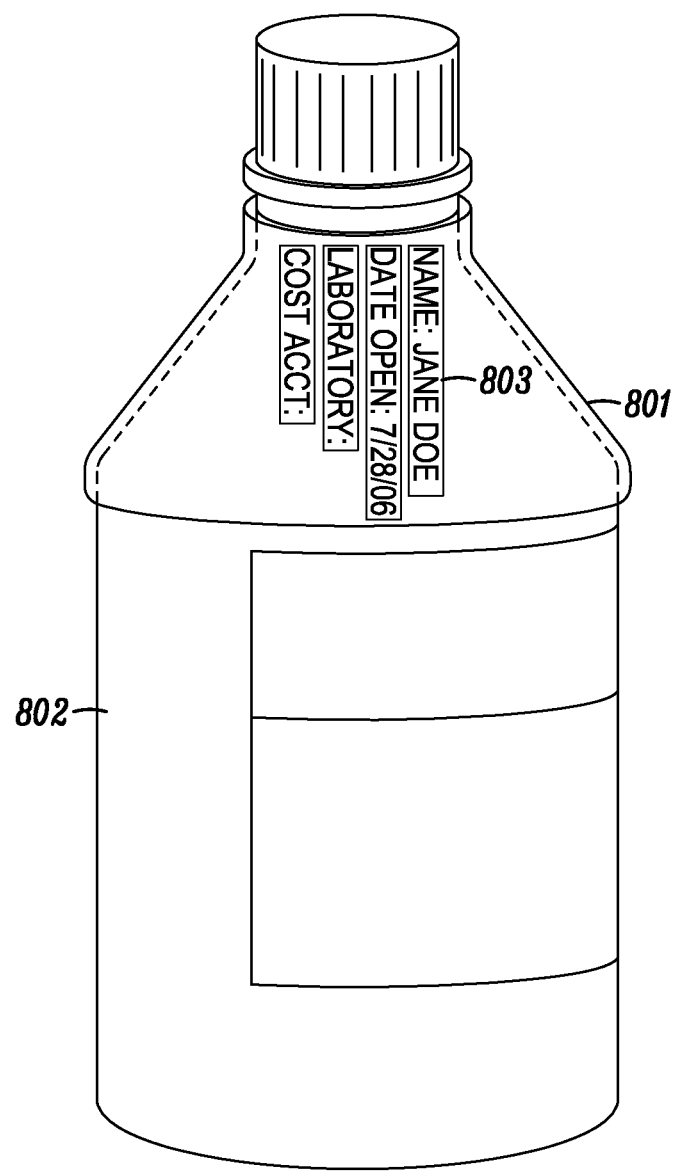
FIGS. 31A, 31B, and 33C shows an exemplary embodiment of a sleeve of the invention which is designed to wrap around a bottle or other container, as well as a bottle around which the sleeve has been wrapped around.
Figure 31B:
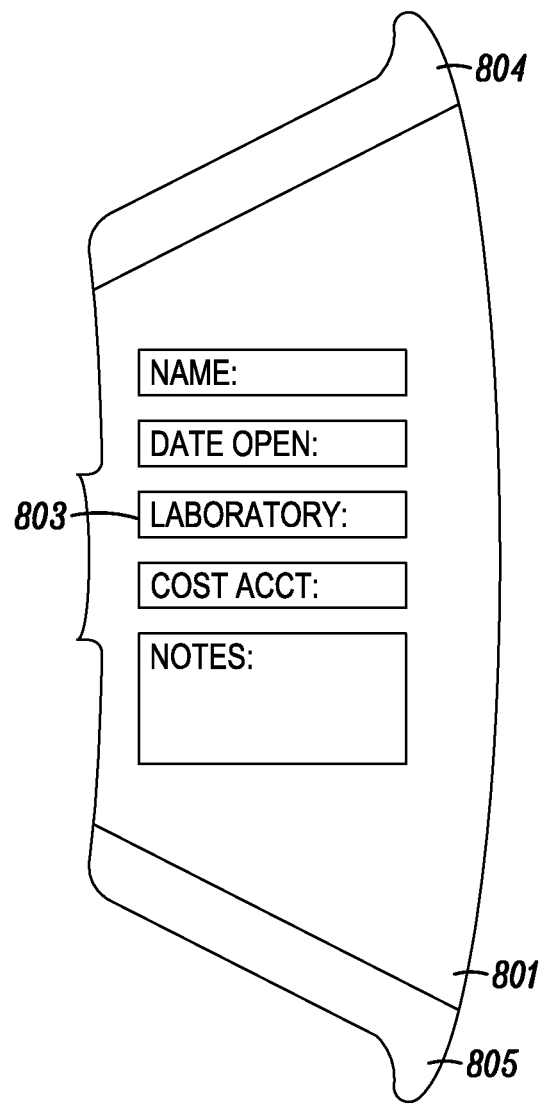
Figure 31C:
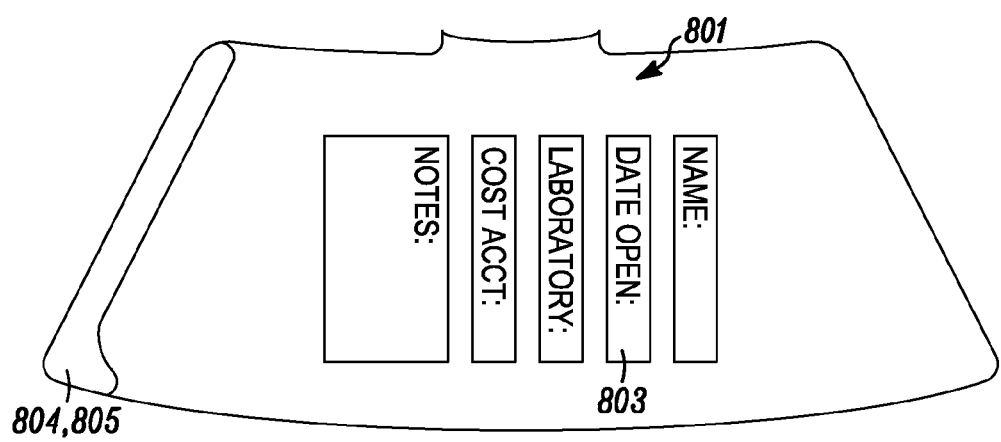

An example of a sleeve of the invention is shown in FIGS. 31A-31C. In FIG. 31A, this embodiment of a sleeve 801 has been placed over a the upper portion of a bottle 802. The sleeve 801 has an area 803 which may be used for entry of particular information by the user. Of course, other areas of the sleeve may also container such information (e.g., can be written upon). Further, the sleeve may contain additional information and may be color coded consistent with a particular product or category of particular products.

FIGS. 31B and 31C show the sleeve of FIG. 31A in open and closed circular formats, respectively. In FIG. 31B, the sleeve 801 is shown as containing an adhesive area 804 designed to be affixed to area 805, thereby forming the closed, circular sleeve shown in FIG. 31C.

Figure 36:
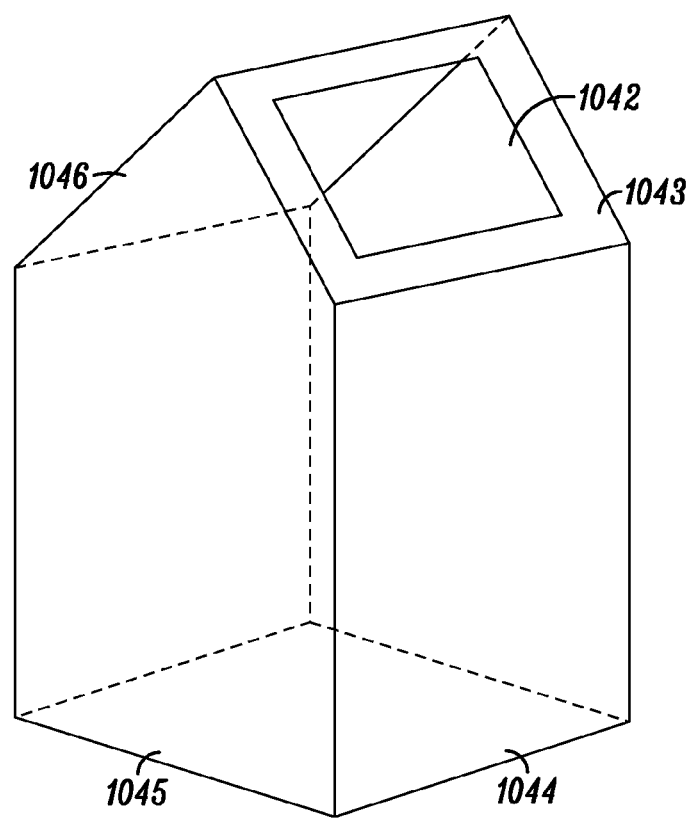
FIG. 36 shows an exemplary embodiment of a sleeve which is designed to be placed over a container from the top (i.e., when the container is positioned such the opening in pointed upwards).

Another embodiment of a sleeve of the invention 1046 is shown in FIG. 36. In this instance, the sleeve is designed to fit over a container such as that shown in FIG. 8. One of the sides of the sleeve 1043 which corresponds to one of the two upper angled panels of the container is left mostly open. The open area 1042 is designed such that the sleeve can pass over the container with minimal steric hindrance from the opening. The "lip" of this side 1043 is designed to contact the panel of the container on which it sits. Sides 1044 and 1045, as well as other surfaces may contain information pertaining to the containers contents and/or may be available for writing upon. Also, one or more back areas of the sleeve 1046 may contain adhesive for affixing the sleeve to containers.

In many instances, sleeves of the invention will be designed such that they may pass over a bottle in which the cover has not been removed. In some instances, it may be necessary to bend the sleeve to fit it over the cover but, in most instances, the stress of fitting the sleeve over the cover area will not be sufficient to tear the sleeve. Thus, in many instances, sleeves of the invention will be made of flexible materials.

The Bottles

A further aspect of the disclosure is shown in various embodiments of containers or bottles disclosed herein. Some of these disclosed embodiments are designed to increase efficiency and/or decrease the likelihood of spills and contamination. Specific embodiments include containers (e.g., bottles) that utilize shapes and/or overall designs that promote accuracy and/or efficiency of movement for the user. In many instances, various embodiments described herein provide user friendly labeling surfaces. This in turn may translate into greater user efficiency and/or fewer spills, thereby decreasing costs. The system also can utilize sealing mechanisms which offer one handed opening and closing and minimal handling of the bottle, thereby decreasing contamination and further increasing user efficiency. Depending on the particular use, containers disclosed herein may be constructed of material tested to meet requirements of applicable state and/or federal regulations, such as those promulgated by the Food and Drug Administration when required.

Various embodiments of container designs are described below. It is understood however, that these designs are exemplary only, and are not intended to describe the entire scope of any invention disclosed herein. FIGS. 3A & 3B are perspective views of a slide top container. The top 4 of this container is a sliding mechanism that can be operated with one hand, or a thumb by a user. The sliding top has three possible positions. A first position, shown in FIG. 3A reveals a first opening 6 into the container. This opening has a lip to channel liquid flow during pouring of liquid out of the container. In a second position shown in FIG. 3B, the slide top is moved in the other direction to reveal a large circular opening 8 that is more suitably shaped for drawing fluid out of the container as with a pipetting device. A third position, not shown, is the closed position in which the slide top is centered on the device, closing and sealing both openings.

The container shown in FIG. 4 is a flexible top container. The container is molded of a deformable material in the neck area 10 so the opening can be pointed toward a user for easier pipette access to the ingredients. The label shown in this drawing has been discussed above. Because of the shape of the bottle, in certain embodiments of this container a label containing information that is needed only occasionally is affixed to the bottom surface of the container. This embodiment also includes a non-removable cover 22. The cover 22 and sliver 24 are molding together and the cover is designed to snap closed on the bottle, again with one-handed operation.

Another embodiment of a container is shown in FIG. 5, and is described herein as a wedge shaped container. This shape offers some advantage in storage, in that bottles may be stored side by side with more efficient use of space than conventional round bottles. The wedge or triangular shape also is easier to handle or grip and allows for maximal label exposure. The embodiment shown in the figure includes a clear cover 34 over the cover that is removable so colored stickers 30 or other identifying information can be placed under the cover and protected. The container is FIG. 5 also includes an indicator strip 18 that aligns with the projection on the cover 34 to indicate that the cover is in the closed and sealed position. Also shown is a temperature indicator 36 that can be added to any of the embodiments described herein.

The embodiment of a container shown in FIG. 6 is a box shaped or boxy container. This container is designed for efficient storage and includes pull up tabs 32 that can be seen for containers that are not placed in the front row. The cover as shown includes a projection 38 to facilitate one-handed opening and closing of the bottle, and can be aligned with a marker on the container to indicate whether the cover is in the open or closed position. An embodiment of a container that includes two chambers is shown in FIG. 7. The bottle includes a lower chamber that holds the original volume of liquid and an upper chamber 44 connected to the lower chamber by a tube 46. When liquid is to be withdrawn, the lower chamber is squeezed, forcing a portion of the liquid up the tube and into the upper chamber where it can be contacted with a pipette without disturbing the lower chamber. Individually removable labels 40 can be used to transfer information between bottles, or between the bottle and a lab notebook or elsewhere as needed, and can also be personalized and affixed to the cover 48.

Figure 11:
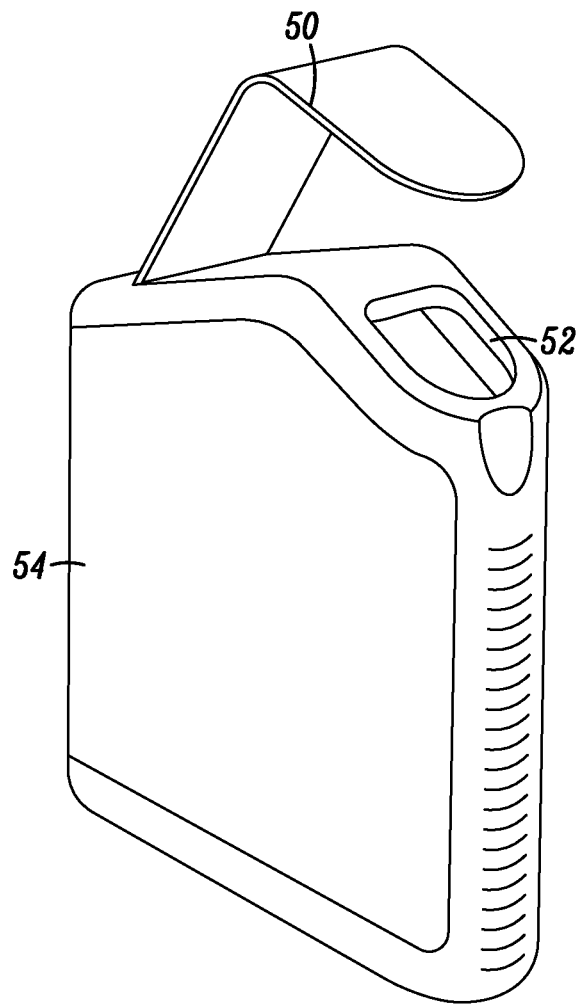
FIG. 11 is a perspective view of a book shaped container.

Another aspect of the disclosure is embodied in the container shown in FIG. 11. This container is book shaped and is designed again for easy one handed opening and closing and easy withdrawal of liquid. The top 50 flips open with the thumb to reveal an easily accessible opening 52 that is angled toward the front so a user does not have to reach above the container to insert a pipette device. The shape also lends itself to a label 54 that wraps around three sides of the container for abundant space for user labeling and manufacturer coding of the contents, and leaves the front face transparent so the volume and color of the contents is easily viewed.

Figure 12:
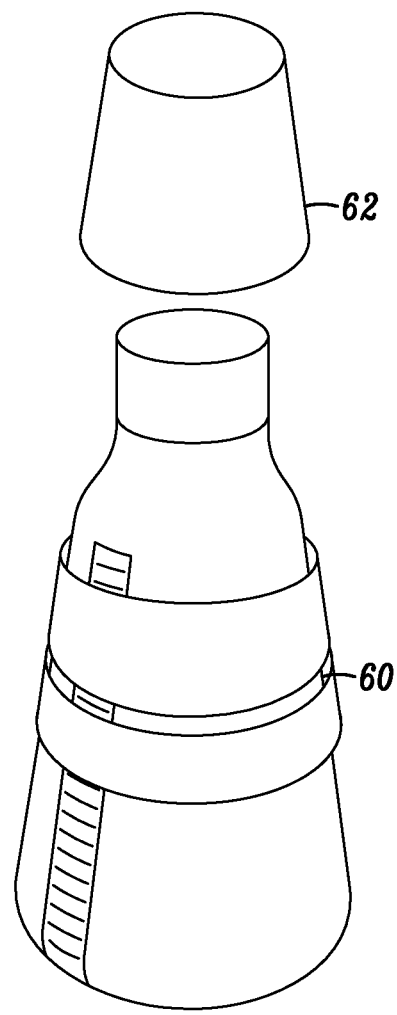
FIG. 12 is a perspective view of a cone shaped container.

A conical container is shown in FIG. 12. Although this container does not provide flat surfaces for user annotations, it is provided with rings 60 that fit over the container at various circumferences to provide user labeling. The container is also provided with a mating conical cover 62. When delivered, the cover may be sealed with an adhesive strip (not shown) that contains a computer readable bar code that is useful for re-ordering purposes.

Figure 14:
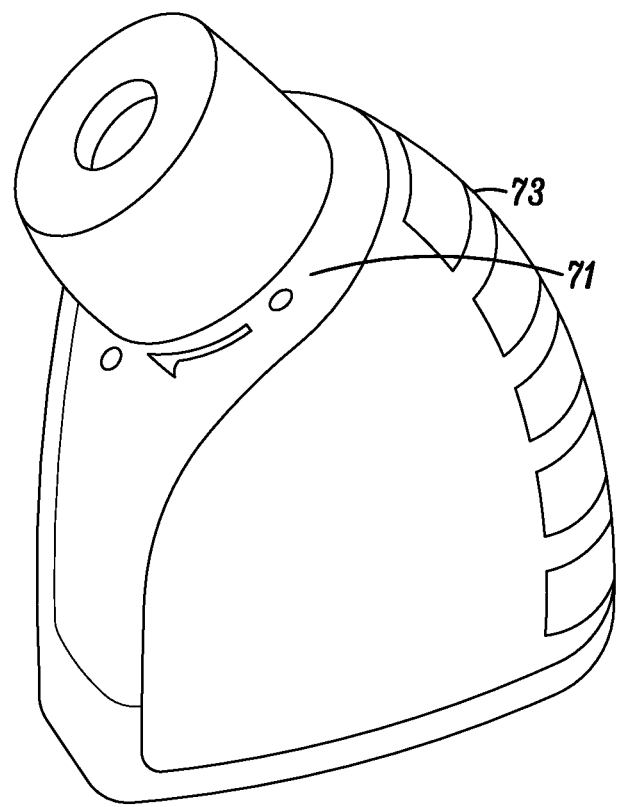
FIG. 14 is a perspective view of a wide mouth container.

A further container design is shown in FIGS. 13A & B. This embodiment includes a harder outer cover 64 and a soft, collapsible inner bag 66 that contains the liquid contents. The hard cover may be made of cardboard or rigid plastic and may incorporate a label that wraps around three sides of the container. The outer cover may also incorporate a tab 68 for user annotation, and a removable marker 65 for personalization of the containers by users. The cover 63 is shown with a ridge to facilitate turning of the cover and to indicate the open or closed state of the cover. As shown in FIG. 13B, a colored strip 67, which may be part of the color code as disclosed herein is disposed under the cover and is exposed when the cover is in the open position. In certain embodiments a removable strip 61 is provided to transfer information from the bottle to other bottles, lab notebooks, etc. or to use for re-ordering. A wide mouthed container is shown in FIG. 14. This bottle has an angled opening to facilitate pipetting and the bottle and cover include an indicator 71 to inform the user if the cover is open or closed. As shown, the cover is opened or closed with only a quarter turn of the cover. The label as shown in the Figure includes the color coding and number information 73 prominently displayed from the rear so it is easily identified by a user. The embodiment as shown may also include a weighted bottom to provide extra stability and a bottom that slopes to the rear to facilitate removing all the liquid from the bottle without causing contamination.

Figure 16:
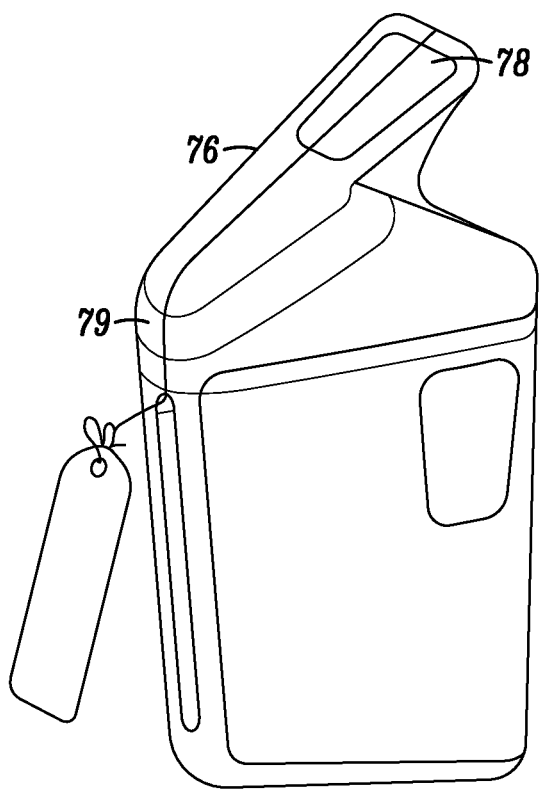
FIG. 16 is a perspective view of a toggle container.
Figure 17:
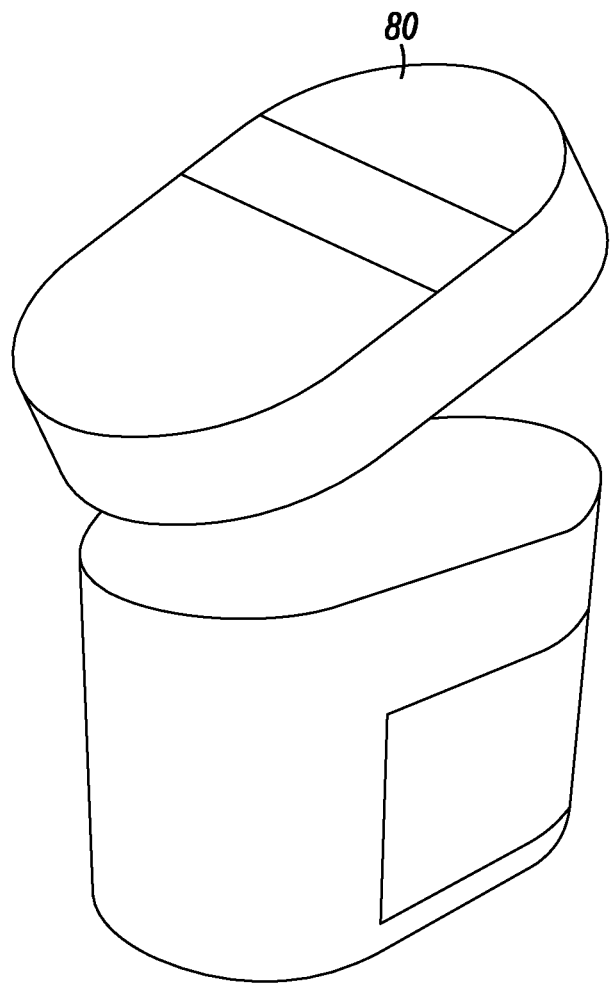
FIG. 17 is a front perspective view of a flip top container.
Figure 18:
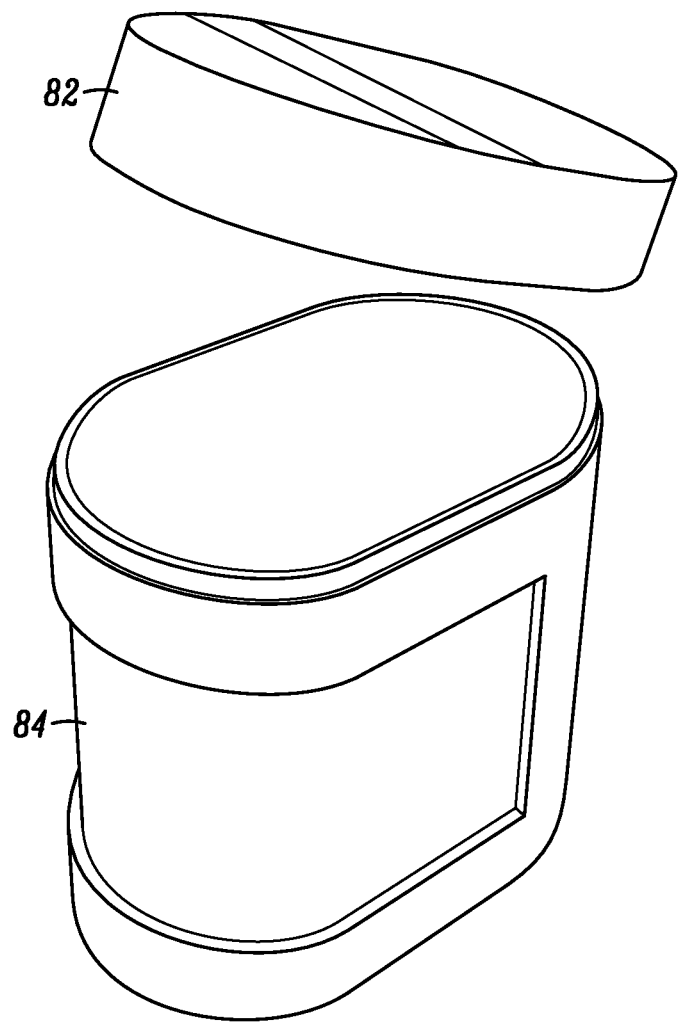
FIG. 18 is a rear perspective view of a flip top container.

A flat container is shown in FIG. 15. This container is efficiently stacked and can provide color and number coded information from the front by use of a color and number coded insert 72 under the cover 74. FIG. 16 shows a container embodiment which includes a toggle opening. The top 76 is easily opened with one hand by flipping up to reveal an angled opening (not shown). The top also provides an angled surface 78 for color and number coding of the contents that is visible from the front during storage in rows. In certain embodiments, the package is delivered with the top covered with a shrinkwrap seal or a celon and a string 79 is provided to facilitate opening of the bottle. Another aspect of the disclosure is an oval shaped container with a slanted top as shown in FIGS. 17 & 18. This top again provides an angled front surface 80 for easy reading of labels during use and storage. The rear of the top includes a recess 82 to depress the flip top and reveal the angled pipette opening (not shown). This allows the user to open the top without having a hand near the opening, thus decreasing probability of contamination. A wrap-around label 84 provides ample space for manufacturer coding and user annotations.

Each of the embodiments described above may also contain any, all, or none of the following features: a wide bottle opening to allow easy pipette access; an external temperature indicator which passively reveals the temperature of the bottle, closure indicators that display with reference to the cover whether the cover is in the closed and sealed position or in the open and unsealed position, a color indicator on the cover and bottle interaction region which is visible when the bottle is open but not when it is sealed, a cover and bottle interaction region which permits removal of the cover with less than three hundred and sixty degrees of rotation; a thickened or otherwise weighted base to add weight to prevent the bottle from toppling over during use or storage; an angled bottom to facilitate the removal of all the contents of a bottle; an angled bottle neck to facilitate smooth content access and removal and a volume gradation on a portion of the bottle through which the volume of liquid in the container can be determined or estimated. Any of the embodiments disclosed may also include a shrink wrap around all or a portion of the container for tamper evidence and that also may incorporate the color coding, or color and number coding as described herein.

The Covers

The covers disclosed herein maybe designed to be compatible with the various container embodiments, and in certain embodiments to maintain sterility while remaining easy to open, particularly with one hand. The covers can be of a variety of shapes and sizes and can be engineered to utilize any acceptable method of attaching to the bottle, such as snap closure, threaded closure, stopper, slide closure, lever closure, or a threaded luer, that in certain embodiments, permits removal with less than 360 degrees of rotation. The covers may also be delivered with a celon, a protective wrapper that surrounds the bottle and cover interaction region prior to first use, which indicates to the user that the bottle has not been opened. This celon can be made of any suitable material such as thin plastic, optionally with a pre-scored section designed to fail upon the application of only minimal pressure to facilitate celon removal. The celon may have a string or other pull instead of or in addition to a pre-scored section, the pulling of which cuts the celon and eases removal. Additionally, some section of the celon may be adhesive and once removed from the bottle, be capable of reattachment by adhesion to be used as a label for the bottle. The celon may also incorporate the color and number coding described herein.

The covers may vary to be compatible with various embodiments of the bottles, and may include, but are not limited to: a rounded white bottle cover, made of an opaque, translucent, or transparent material, or any combination thereof, which may or may not have one or more (e.g., one, two, three, four, five, ten, twenty, thirty, one to fifty, ten to seventy, twenty to eighty, twenty-five to forty, etc.) vertical ridges on it to facilitate opening, that has either or both a colored region and colored product identifier on the top; a rounded colored bottle cover, made of an opaque, translucent, or transparent material, or any combination thereof, which may or may not have vertical ridges or other textured areas on it, that may or may not have a product identifier on it; a mostly rounded bottle cover, made of an opaque, translucent, or transparent material, or any combination thereof, which may or may not have ridges on it, that has an indicator or flap on it that facilitates one handed opening and indicates the status of the bottle as open or closed based on the indicator's position; a hinged, dual angled cover, which has large surfaces for labeling, that does not expose the inside of the cover to contamination when opened; a bi-directional slide top cover with one or more openings for content access; and a see-saw type, toggle cover; or a flip-top cover. In certain embodiments, a cover as disclosed herein can also include a safety feature to prevent inadvertent opening of the cover, or for containers that include volatile materials, a safety vent system can be employed.

Figure 32A:
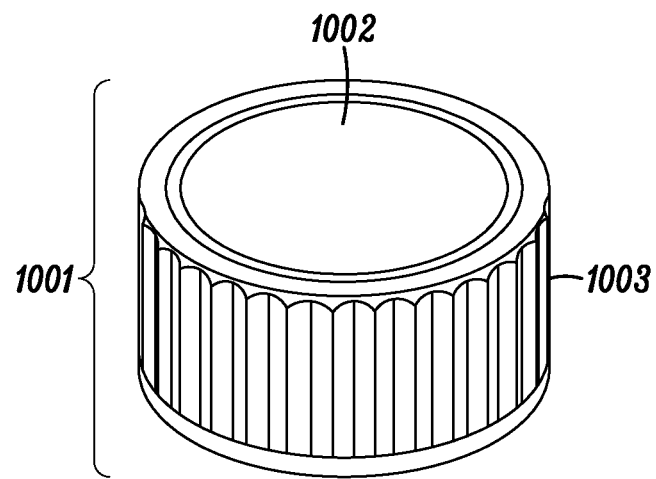
FIGS. 32A, 32B, 32C, 32D, 32E, and 32F show six views (i.e., angled top, angled underside, cutaway side, detailed cutaway side, top, and side, respectively) of an exemplary cover of the invention.
Figure 32B:
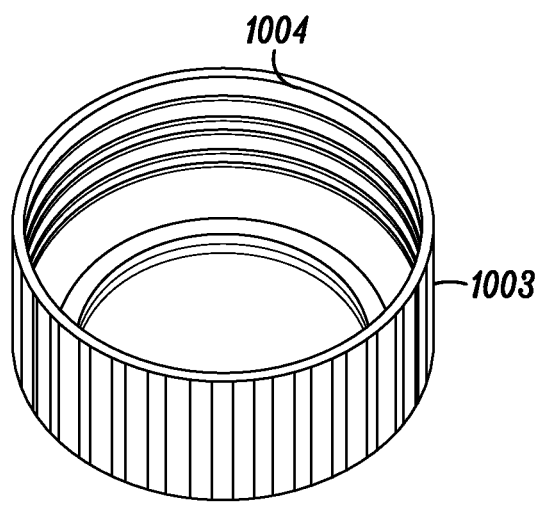
Figure 32D:
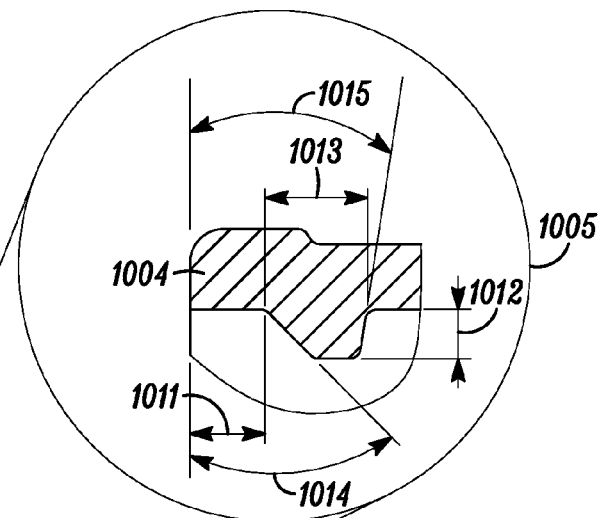
Figure 32C:
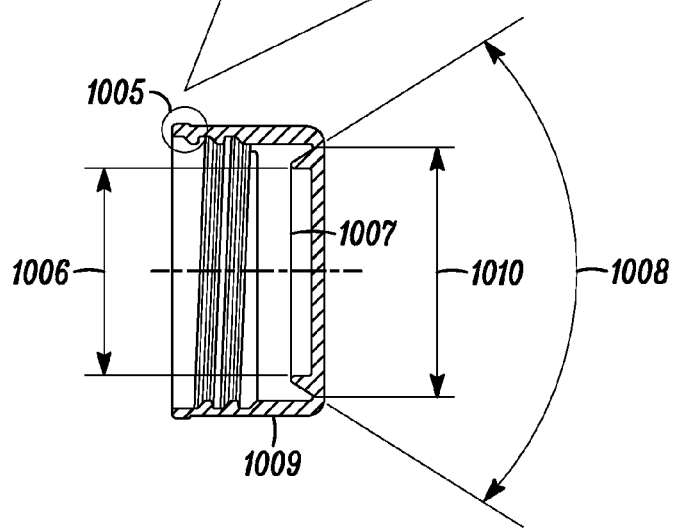
Figure 32E:
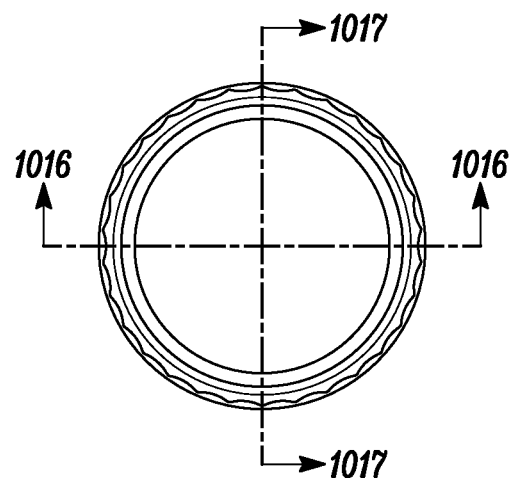
Figure 32F:
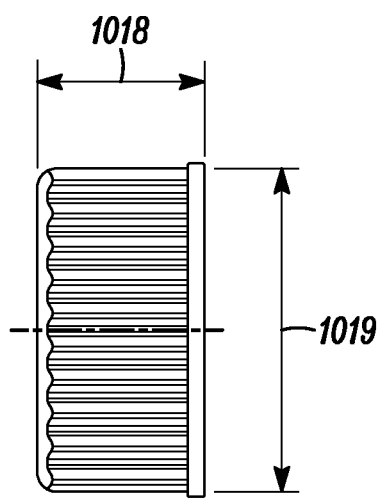

An exemplary cover of the invention 1001 is shown in FIGS. 32A-32F. The cover 1001, as shown, is designed to fit containers of FIGS. 33A-33E, 34A-34E, and 35A-35E. The cover 1001 includes an area 1002 for affixing a color coded label as discussed above, ridges 1003 to provide increased grip or ergonomic advantage to the user, and threading 1004 that allows for easy opening of the bottle. FIG. 32C shows a cutaway side view of the cover 1001 where the width 1006 of the inner plug 1007 is 33.37 mm, and its angle 1008 from the cover sides 1009 is 60 degrees. The effective width 1010 of the inner plug 1007 is 38.87 mm. A more detailed view of the threading 1004 is shown in FIG. 32D. The base height of the cover before the first thread 1011 is 2 mm. The total width of the cover's first thread 1012 is 1.19 mm and the overall height of the cover's first thread 1013 is 2.386 mm, with the lower end of the thread angle 1014 at 45 degrees and the upper end of the thread angle 1015 at 10 degrees. FIG. 32E illustrates opening and closing mechanisms as discussed herein. The overall height of the cover 1018 is 24.5 mm and the overall width of the cover 1019 is 48.09 mm, as shown in FIG. 32F.

Each of the described cover embodiments may also contain any, all, or none of the following features: a recessed top; a removable transparent or translucent cover that locks into place on the cover allowing color coding or personalization of the cover; a removable opaque marker that locks into place on the cover, which can be user annotated and used for information transfer, an indicator that displays the closed or open status of a bottle based on the alignment of some feature on the cover with a part of the bottle, for example lining a groove in the cover with a grove in the bottle, or lining up a protrusion from the cover with indented or elevated circles on the bottle; a non-threaded flare that extends beyond the cover and bottle interaction region and covers part of the top of the bottle that prevents the threaded section of the cover from making contact with non-sterile surfaces, add-on markers that lock onto the cover and allow users to mark or personalize bottles; a ridge or protrusion on the cover with a hole in it to allow users to add additional tags or to help manipulate the bottle, a leash made of an acceptable material that prevents the cover from being separated from the bottle, and a rigid leash that when opened prevents the cover from making contact with the sides of the bottle. Any of the covers disclosed may also be composed of material that is colored to match the color code of the product, or any of the covers may incorporate significant white or lightly colored space for user annotation.

Figure 33A:
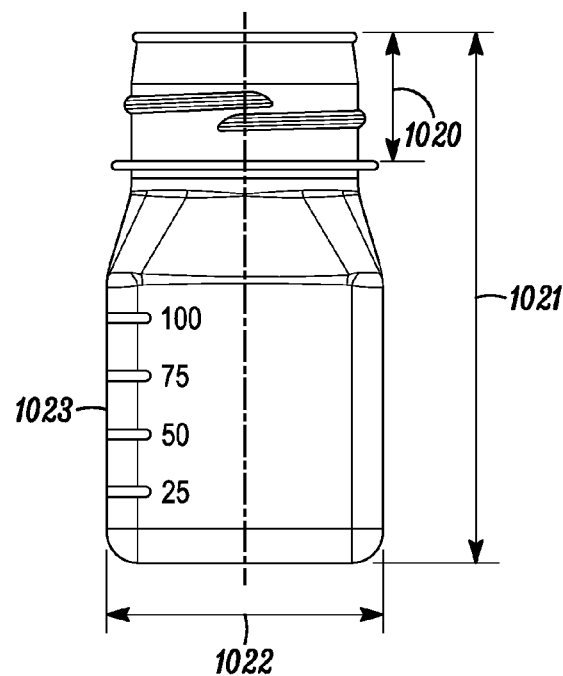
Figure 33B:
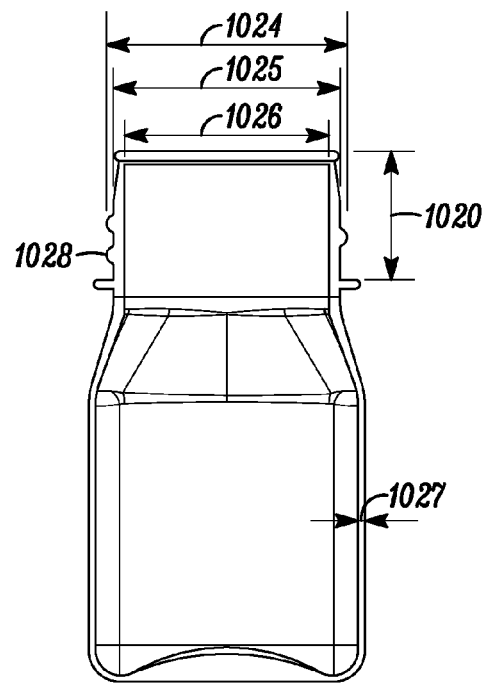
Figure 33C:
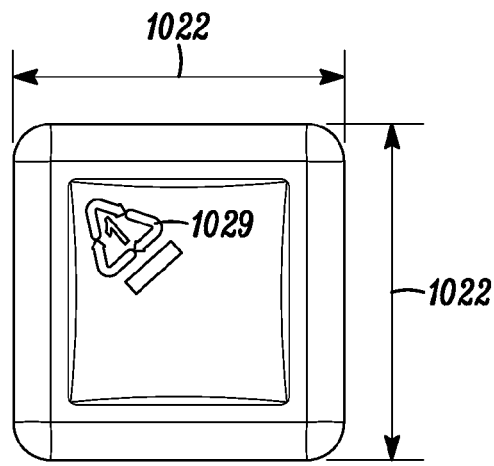
Figure 34A:
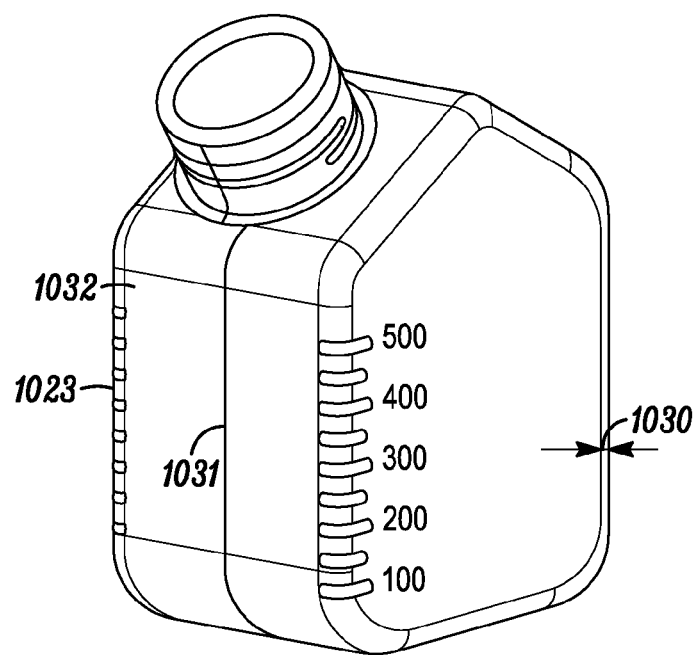
FIGS. 34A, 34B, 34C, 34D, and 34E show five views (i.e., side, side, frontal, top, and bottom) of an exemplary container of the invention. 1023 indicates volume graduation markings on both front right and left sides of the container. 1031 indicates the parting line of the container.
Figure 34B:
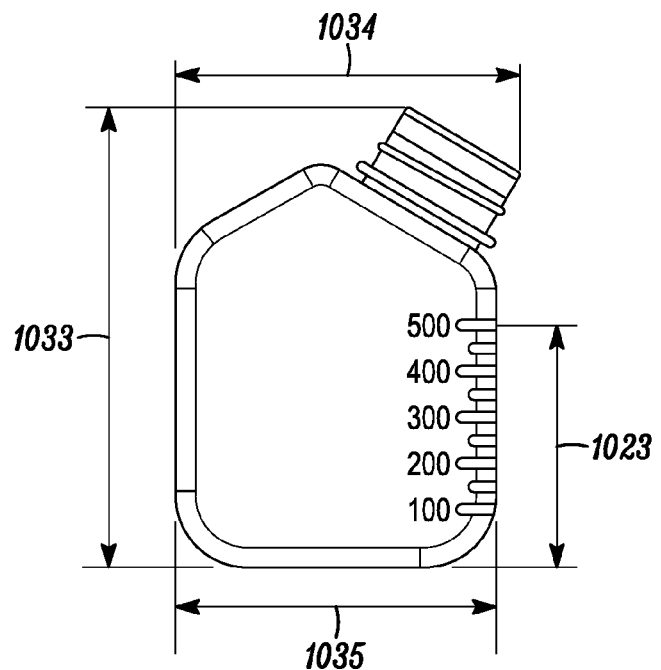
Figure 34C:
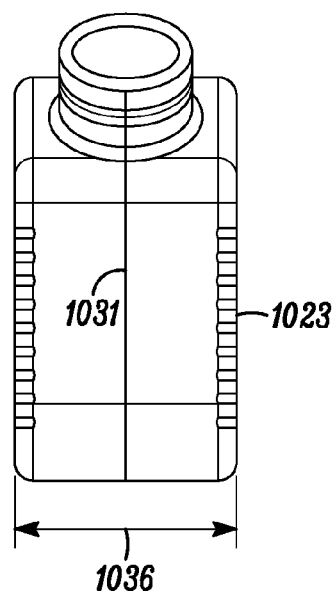
Figure 34D:
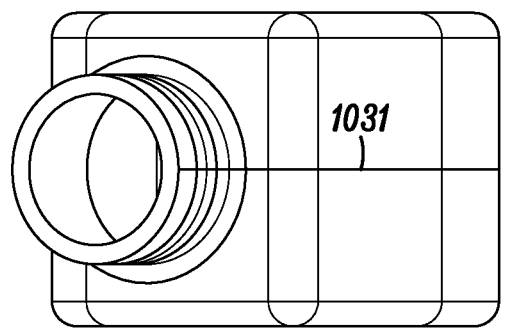
Figure 34E:
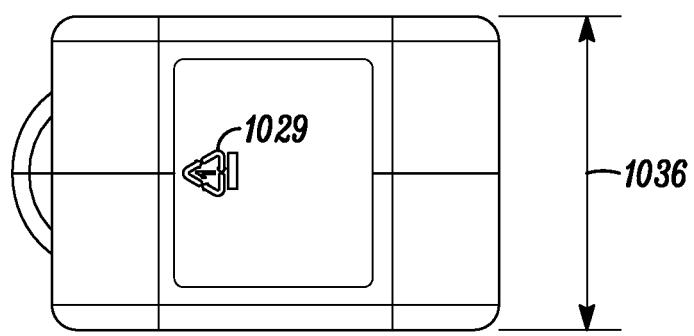
Figure 35A:
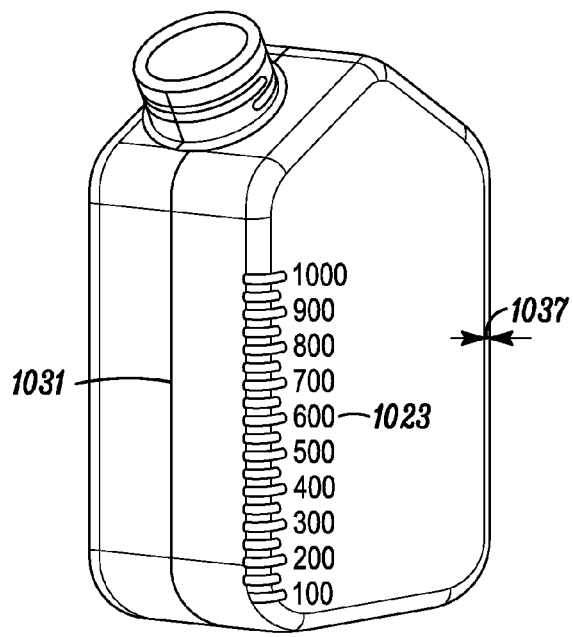
FIGS. 35A, 35B, 35C, 35D, and 35E show five views (i.e., two side, one frontal, one top, and one bottom) of an exemplary container of the invention.
Figure 35B:
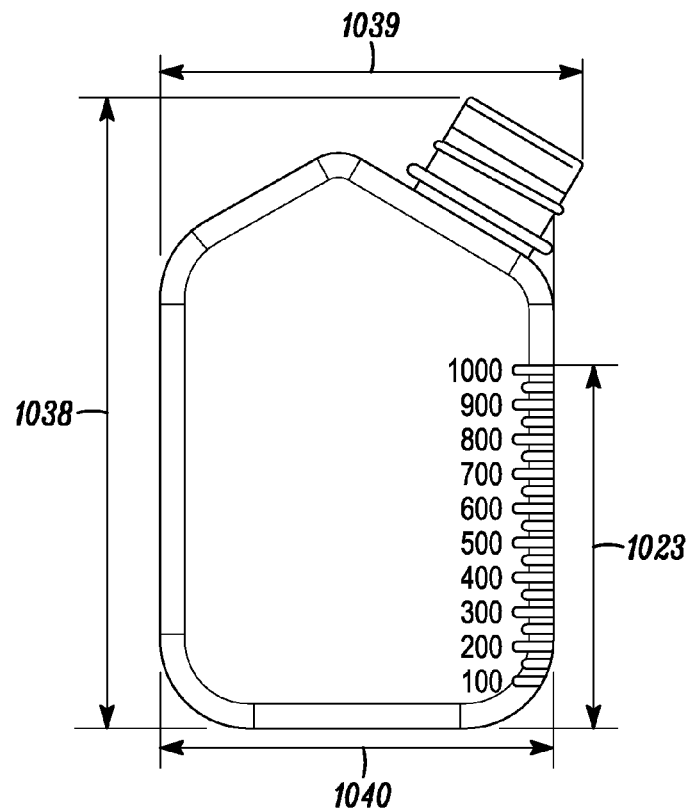
Figure 35C:
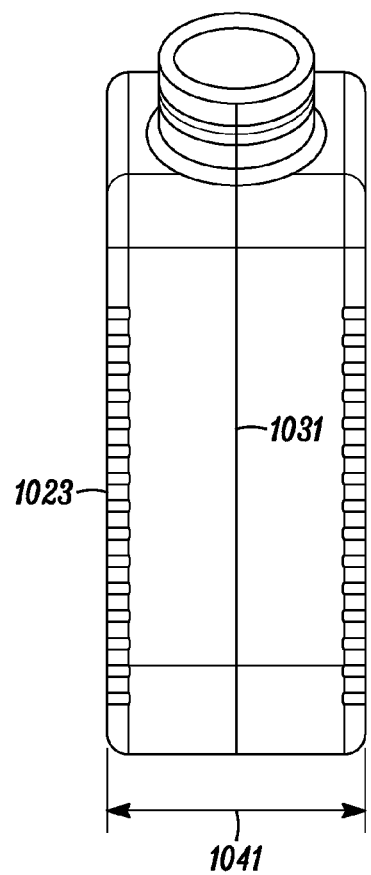
Figure 35D:
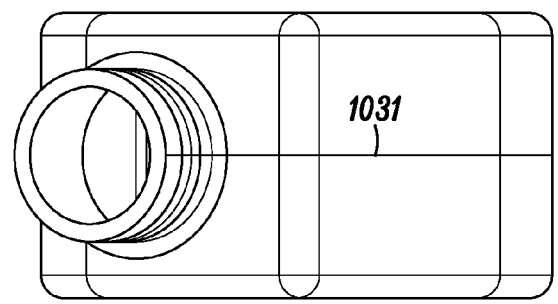
Figure 35E:
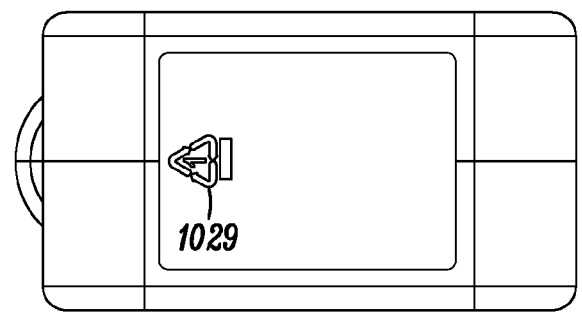

An exemplary container of the invention is shown in FIGS. 33A-33C. The bottle has a square footprint, essentially planar sides to facilitate easier label affixation or annotation, a wide opening to facilitate ease of pipetting, and graduation marks 1023 to aid in quickly identifying an approximate amount of material contained in the bottle. The overall height of the bottle 1021 is 96.21 mm while the width and depth of the bottle 1022 is 51 mm. The height of the threaded area of the bottle 1020 is 23 mm. The average wall thickness 1027 of this bottle is 0.86 mm. The inner diameter of the opening 1026 is 36.6 mm, the outer diameter of the opening 1025 is 41.43 mm, and the outer diameter of the opening before the thread start 1024 is 43.81 mm. In the bottle as shown, the ratio of the depth 1022 to width 1022 to overall height 1021 is about 1:1:1.89. The depth:width:height ratio calculated here is based upon a total container height, including the height of the spout. The ratios of the lengths of sides (see, for examples, the description for FIGS. 26A-26C and the A:B or A:C ratio) may also be used to define the container of FIGS. 33A-33C, or other containers of the invention. In many instances, volume of containers such as those shown in FIGS. 33A-33C will be 10, 15, 20, 25, 30, 35, 55, 65, 75, 100, 157, 173, 196, 200, 250, 350, 400, etc. (e.g., between about 10 and 400; between about 50 and 400; between about 100 and 400; between about 10 and 300; between about 10 and 200; between about 50 and 300; between about 50 and 200; etc.)).

An additional exemplary container of the invention is shown in FIGS. 34A-34E. As in Example 3, the bottle has a rectangular footprint, an angled opening, and rounded corners to aid in easy emptying of the bottle with a pipette; the other advantages discussed above are incorporated herein. Additionally, the bottle has graduation markings 1023 on both right and left front sides of the bottle to aid in quickly identifying an approximate amount of material contained in the bottle. The drawings also show the parting line 1031 of the bottle as well as an area 1032 for affixing a label. The parting line is formed when two sections, which are made separately, are brought together to form the container. The average wall thickness 1030 of this bottle is 0.95 mm. The following dimensions of the bottle are to the theoretical sharp corners past the rounded corners. The overall height of the container 1033 is 145.3 mm and the overall depth of the container 1034 is 108.32 mm, including the angled-entry opening. The effective depth of the container 1035 (corresponding to side C of FIGS. 26A-26C) is 101 mm. The width of the container 1036 (corresponding to the Z plane of FIG. 26A-26C or I of FIG. 27A) is 72 mm. In the bottle as shown, the ratio of the depth 1035 to width 1036 to overall height 1033 is about 1:1.40:2.02. In many instances, volume of containers such as those shown in FIGS. 34A-34E will be 200, 250, 350, 400, 447, 500, 554, 600, 650, 776, 802, 900, 1,000, 1,250, etc. (e.g., between about 200 and 1,250; between about 300 and 1,250; between about 400 and 1,250; between about 500 and 1,250; between about 600 and 1,250; between about 200 and 1,000; between about 200 and 800; etc.)).

Another exemplary container of the invention is shown in FIGS. 35A-35E. As in the exemplary container above, the bottle has a rectangular footprint, an angled opening, and graduation markings 1023, the advantages of which are incorporated herein. The average wall thickness 1037 of this bottle is 0.94 mm. The following dimensions of the bottle are to the theoretical sharp corners past the rounded corners. The overall height of this container 1038 is 199.47 mm and the overall depth of the container 1039 is 132.599 mm, including the angled-entry opening. The effective depth of the container 1040 (corresponding to side C of FIGS. 26A-26C) is 128.15 mm. The width of the container 1041 (corresponding to the Z plane of FIG. 26A-26C or I of FIG. 27A) is 72 mm. In the bottle as shown, the ratio of the depth 1040 to width 1041 to overall height 1038 is about 1:1.78:2.77. In many instances, volume of containers such as those shown in FIGS. 35A-35E will be 900, 1,000, 1,250, 1,375, 1,454, 1,500, 1,700, 1,763, 1,800, 1,900, 2,000 etc. (e.g., between about 900 and 2,000; between about 1,000 and 2,000; between about 1,400 and 2,000; between about 1,500 and 2,000; between about 900 and 1,500; between about 900 and 1,400; between about 1,200 and 1,500; etc.)).

Wall thicknesses of containers of the invention will vary greatly based upon many factors, including the materials the containers are made of, the contents (e.g., pressurized or non-pressurized contents), and the size of the container. Some wall thickness will be 0.2 mm, 0.25 mm, 0.5 mm, 0.75 mm, 0.85 mm, 0.95 mm, 1.0 mm, 1.1 mm, 1.2 mm, 1.5 mm, 2.0 mm, 2.5 mm, etc. (e.g., between from about 0.2 mm and about 2.5 mm; between from about 0.5 mm and about 2.5 mm; between from about 0.5 mm and about 2.0 mm; between from about 0.5 mm and about 1.5 mm; between from about 0.5 mm and about 1.0 mm; etc.). By "wall thickness" will typically be meant an average thickness with a variation equal to or less than 1%, 2%, 3%, 4%, 5%, 6%, 7%, 8%, 9%, 10%, 11%, 12%, 13%, 14%, 15%, 16%, 17%, 18%, 19%, or 20%. In most instances, wall thickness will be measured in flat areas and away for corners or curves. In some instances, wall thickness will be measured only near the central portion of flat sides. By central portion is meant the center 50% of a side. Thus, if a side is 100 mm in height and 80 mm in width, measurements would be taken between 25 mm from the bottom to 25 mm from the top and 20 mm from the left side to 20 mm from the right side. In many instances, thickness measurements will be taken at numerous (e.g., at least ten, fifteen, twenty, thirty, forty, fifty, etc.) locations to arrive at an average. Further, these thickness measurements will often be spaced at least 0.2 mm, 0.4 mm, 0.5 mm, 0.7 mm, 0.8 mm, 0.9, 1.0 mm, etc. apart from each other.

Business Methods

Figure 19:
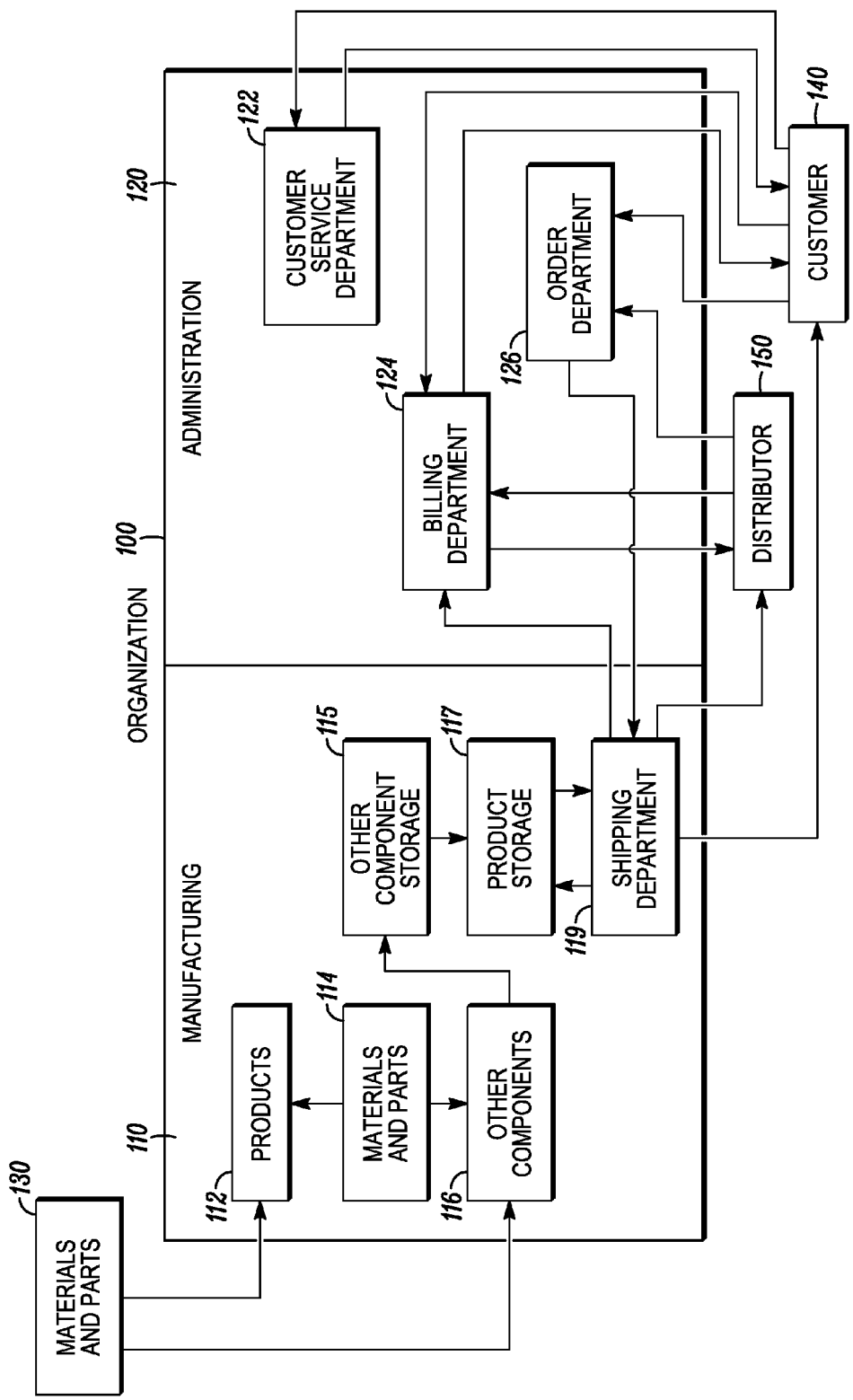
FIG. 19 is a flow diagram of a business system.

The present disclosure also provides systems and methods of providing company products to an acquirer of the products, for example, systems and methods for providing a customer or a product distributor a product such as a reagent or culture media identified by a labeled container and/or cover and/or contained within a bottle described herein. FIG. 19 provides a schematic diagram of a product management system. In practice, the blocks in FIG. 19 can represent any organization which can be one legal entity or a combination of entities that provides products or systems as disclosed herein. This organization can include departments in a single building or in different buildings, a computer program or suite of programs maintained by one or more computers, a group of employees or contractors, a computer I/O device such as a printer or fax machine, a third party entity or company that is otherwise unaffiliated with the company, or the like.

The product management system as shown in FIG. 19 is exemplified by organization 100, which receives input in the form of an order from a product or system acquirer, e.g., distributor 150 or customer 140 or the like, to order department 126, or in the form of materials and parts 130 from an acquirer; and provides output in the form of a product delivered from shipping department 119 to distributor 150 or customer 140. Organization 100 system is organized to optimize receipt of orders and delivery of products to a party outside of the company in a cost efficient manner, particularly a reagent identified by a labeled container and/or cover and/or contained within a container described herein, and to obtain payment either directly or indirectly, for such product.

With respect to methods of the present disclosure, the term "materials and parts" refers to items that are used to make and package a product or other component that organization 100 sells to an acquirer. As such, materials and parts include, for example, culture media, buffers, paper, ink, reaction vessels, plastic, glass, filters, glucose, etc. In comparison, the terms "other components" and "products" refer to items sold or otherwise supplied by the organization. Other components are exemplified by labels, covers, bottles, collars, and sleeves. As such, it will be recognized that an item useful as materials and parts as defined herein further can be considered an "other component", which can be provided by the organization. Thus, the term "products" refers to materials and parts as well as other components that are sold or desired to be sold or otherwise provided by an organization to one or more acquirers or users. Products exemplified herein include, but are not limited to culture media such as cell culture media and sera packaged in color coded labeled bottles, in which color coded packaging or labeling in combination with a simple, one, two, or three digit number or alphanumeric indicator is used to indicate the exact product from a plurality of available products.

Referring to FIG. 19, organization 100 includes manufacturing 110 and administration 120. Products 112 and other components 116 are produced in manufacturing 110, and can be stored separately therein such as in product storage 117 and other component storage 115, respectively. Materials and parts 130 can be provided to organization 100 from an outside source and/or materials and parts 114 can be prepared by organization, and used to produce products 112 and other components 116, which, in turn, can be assembled and sold or otherwise supplied as a product. Manufacturing 110 also includes shipping department 119, which, upon receiving input as to an order, can obtain products to be shipped from product storage 117 and forward the product to a party outside the company.

For purposes of the disclosure, product storage 117 can store empty bottles and empty labeled bottles as well as labeled and covered bottles containing culture medium or other products. For example, upon receiving input from order department 126 that a customer 140 has ordered a 500 milliliter bottle of DMEM (low glucose) for example, shipping department 119 can obtain from product storage 117 this product and ship the product to customer 140 (and providing input to billing department 124 that the product was shipped).

As further exemplified in FIG. 19, administration 120 includes order department 126, which receives input in the form of an order for a product from customer 140 or distributor 150. Order department 126 then provides output in the form of instructions to shipping department 119 to fill the order (i.e., to forward products as requested to customer 140 or distributor 150). Shipping department 119, in addition to filling the order, further provides input to billing department 124 in the form of a confirmation that the products have been shipped. Billing department 124 then can provide output in the form of a bill to customer 140 or distributor 150 or other acquirer as appropriate, and can in certain embodiments further receive input that the bill has been paid, or, if no such input is received, can further provide output to customer 140 or distributor 150 that such payment may be delinquent.

An additional optional component of organization 100 includes a customer service department 122, which can receive input from customer 140 and can provide output in the form of feedback or information to customer 140. Furthermore, although not shown in FIG. 19, customer service 122 can receive input or provide output to any other component of organization. For example, customer service department 122 can receive input from customer 140 indicating that an ordered product was not received, wherein customer service department 122 can provide output to shipping department 119 and/or order department 126 and/or billing department 124 regarding the missing product, thus providing a means to assure customer 140 satisfaction. Customer service department 122 also can receive input from customer 140 in the form of requested technical information, for example, for confirming that instructions of the disclosure can be applied to the particular need of customer 140, and can provide output to customer 140 in the form of a response to the requested technical information.

As such, the components of organization 100 are suitably configured to communicate with each other to facilitate the transfer of materials and parts, other components, products, and information within organization 100, and organization 100 is further suitably configured to receive input from or provide output to an outside party. For example, a physical path can be utilized to transfer products from product storage 117 to shipping department 119 upon receiving suitable input from order department 126. Order department 126, in comparison, can be linked electronically with other components within organization 100, for example, by a communication network such as an intranet, and can be further configured to receive input, for example, from customer 140 by a telephone network, by mail or other carrier service, or via the internet. For electronic input and/or output, a direct electronic link, such as a T1 line or a direct wireless connection, can be established, particularly within organization 100 and, if desired, with distributor 150 or materials or parts provider 130, or the like.

Although not illustrated, organization 100 has one or more data collection systems, including, for example, a customer data collection system, which can be realized as a personal computer, a computer network, a personal digital assistant (PDA), an audio recording medium, a document in which written entries are made, any suitable device capable of receiving data, or any combination of the foregoing. Data collection systems can be used to gather data associated with a customer 140 or distributor 150, including, for example, a customer's shipping address and billing address, as well as more specific information such as a customer's or other acquirer's ordering history and payment history, such data being useful, for example, to determine that the acquirer has made sufficient purchases to qualify for a discount on one or more future purchases.

Organization 100 can utilize a number of software applications to provide components of organization 100 with information or to provide a product or system acquirer access to one or more components of organization 100, for example, access to order department 126 or customer service department 122. Such software applications can comprise a communication network such as the Internet, a local area network, or an intranet. For example, in an internet-based application, a customer 140 can access a suitable web site and/or a web server that cooperates with order department 126 such that customer 140 can provide input in the form of an order to order department 126. In response, order department 126 can communicate with customer 140 to confirm that the order has been received, and can further communicate with shipping department 119, providing input that products should be shipped to customer 140. In this manner, the business of organization 100 can proceed in an efficient manner.

In a networked arrangement, billing department 124 and shipping department 119, for example, can communicate with one another by way of respective computer systems. As used herein, the term "computer system" refers to general purpose computer systems such as network servers, laptop systems, desktop systems, handheld systems, personal digital assistants, computing kiosks, and the like. Similarly, in accordance with known techniques, distributor 150 can access a web site maintained by organization 100 after establishing an online connection to the network, particularly to order department 126, and can provide input in the form of an order. If desired, a hard copy of an order placed with order department 126 can be printed from the web browser application resident at distributor 150.

The various software modules associated with the implementation of the present disclosure can be suitably loaded into the computer systems resident at organization 100 and any acquirer as desired, or the software code can be stored on a computer-readable medium such as a floppy disk, magnetic tape, or an optical disk. In an online implementation, a server and web site maintained by organization 100 can be configured to provide software downloads to remote users such as distributor 150, materials and parts 130, and the like. When implemented in software, the techniques of the present disclosure are carried out by code segments and instructions associated with the various process tasks described herein.

Thus, methods for selling or supplying products to such parties are provided, as are methods related to sales or supplies, including customer support, billing, product inventory management within the organization, etc. Examples of such methods are shown in FIG. 19, including, for example, wherein materials and parts 130 can be acquired from a source outside of organization 100 (e.g., a supplier) and used to prepare products, such as color coded labeled and capped bottles of DMEM 120, for example, which can be maintained as an inventory in product storage 117. The other components 116 can be obtained from a source outside of organization 100 (materials and parts 130) or can be prepared within organization 100 (materials and parts 114). As such, the term "product" is used generally herein to refer an item sent to an acquirer of the product (a customer, a distributor, etc.).

At the appropriate time, the product is removed from product storage 117, for example, by shipping department 119, and sent to a requesting party such as customer 140 or distributor 150. Typically, such shipping occurs in response to the acquirer placing an order, which is then forwarded within the organization as exemplified in FIG. 19, and results in the ordered product being sent to the acquirer. Data regarding shipment of the product to the party is transmitted further within the organization, for example, from shipping department 119 to billing department 124, which, in turn, can transmit a bill to the acquirer, either with the product, or at a time after the product has been sent. Further, a bill can be sent in instances where the acquirer has not paid for the product shipped within a certain period of time (e.g., within 30 days, within 45 days, within 60 days, within 90 days, within 120 days, within from 30 days to 120 days, within from 45 days to 120 days, within from 60 days to 120 days, within from 90 days to 120 days, within from 30 days to 90 days, within from 30 days to 60 days, within from 30 days to 45 days, within from 60 days to 90 days, or during a similar time period). Typically, billing department 124 also is responsible for processing payment(s) made by the acquirer. It will be recognized that variations from the exemplified method can be utilized; for example, customer service department 122 can receive an order from the acquirer, and transmit the order to shipping department 119 (not shown), thus serving the functions exemplified in FIG. 19 by order department 126 and the customer service department 122.

Methods of the disclosure also include providing technical service to those using a product. While such a function can be performed by individuals involved in product research and development, inquiries related to technical service generally are handled, routed, and/or directed by an administrative department of the organization (e.g., customer service department 122). Often communications related to technical service (e.g., solving problems related to use of the product or individual components of the product) require a two way exchange of information, as exemplified by arrows indicating pathways of communication between customer 140 and customer service department 122.

As mentioned above, any number of variations of the process exemplified in FIG. 19 are possible and within the scope of the disclosure. Accordingly, the disclosure includes methods (e.g., business methods) that involve (1) the production of products; (2) receiving orders for these products; (3) sending the products to parties placing such orders; (4) sending bills to parties obliged to pay for products sent to such; and/or (5) receiving payment for products sent to parties. For example, methods are provided that comprise two or more of the following steps: (a) obtaining parts, materials, and/or components from a supplier; (b) preparing one or more first products (e.g., a bottle or a color coded label); (c) storing the one or more first products of step (b); (d) combining the one or more first products of step (b) with one or more other components to form one or more second products (e.g., a color coded labeled and covered bottle of DMEM 120 culture medium, for example); (e) storing the one or more first products of step (b) or one or more second products of step (d); (f) obtaining an order of a first product of step (b) or a second product of step (d); (g) shipping either the first product of step (b) or the second product of step (d) to the party that placed the order of step (f); (h) tracking data regarding the amount of money owed by the party to which the product is shipped in step (g); (i) sending a bill to the party to which the product is shipped in step (g); (j) obtaining payment for the product shipped in step (g) (generally, but not necessarily, the payment is made by the party to which the product was shipped in step (g)); and (k) exchanging technical information between the organization and a party in possession of a product shipped in step (d) (typically, the party to which the product was shipped in step (g)).

The present disclosure also provides systems and methods for providing information as to availability of a product (e.g., a bottle or a color coded labeled and covered bottle containing DMEM 120, for example) to parties having potential interest in the availability of the product. Such a method, which encompasses a method of advertising to the general or a specified public, the availability of the product can be performed, for example, by transmitting product description data to an output source, for example, an advertiser; further transmitting to the output source instructions to publish the product information data in media accessible to the potential interested parties; and detecting publication of the data in the media, thereby providing information as to availability of the product to parties having potential interest in the availability of the product.

Accordingly, the present disclosure provides methods for advertising and/or marketing devices, products, and/or methods of the disclosure, such methods providing the advantage of inducing and/or increasing the sales of such devices, products, and/or methods. For example, advertising and/or marketing methods of the disclosure include those in which technical specifications and/or descriptions of devices and/or products; methods of using the devices and/or products; and/or instructions for practicing the methods and/or using the devices and/or products are presented to potential interested parties, particularly potential purchasers of the product such as customers, distributors, and the like. In particular embodiments, the advertising and/or marketing methods involve presenting such information in a tangible or an intangible form to the potential interested parties. As disclosed herein and well known in the art, the term "intangible form" means a form that cannot be physically handled and includes, for example, electronic media (e.g., e-mail, internet web pages, etc.), broadcasts (e.g., television, radio, etc.), and direct contacts (e.g., telephone calls between individuals, between automated machines and individuals, between machines, etc.); whereas the term "tangible form" means a form that can be physically handled.

The disclosure further provides methods associated with the design of custom products. These methods include, for example, (1) the taking an order from a customer for medium with specific ingredient percentages, (2) preparation of one or more color coded labeled and covered bottles containing the medium, (3) and providing (e.g., shipping) the product to the customer. Additionally, in particular embodiments, the customer may be billed for the medium with the bill either being sent to the customer along with the medium or sent separately.

Figure 20:
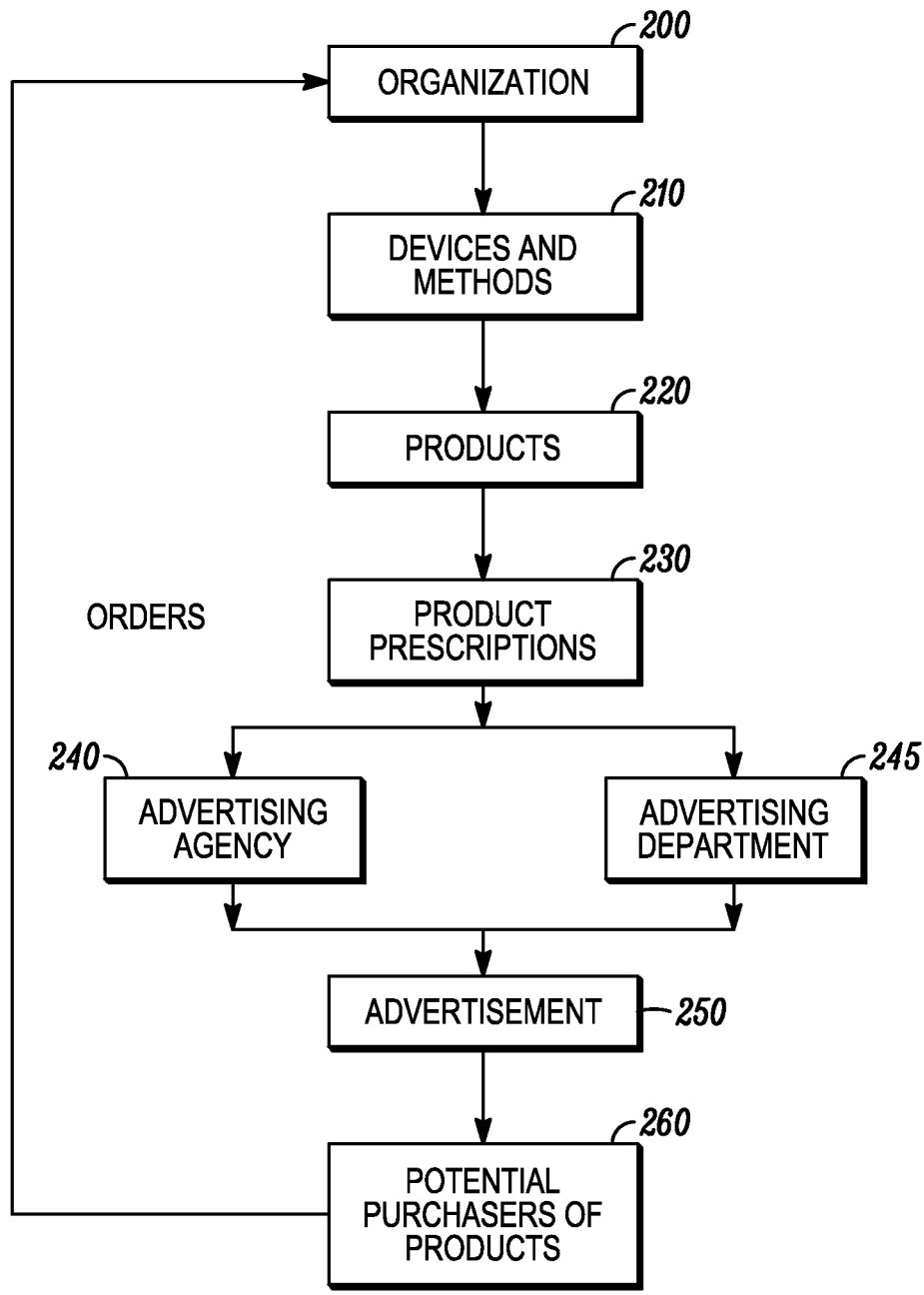
FIG. 20 is a flow diagram of a method for providing products as disclosed herein.
Figure 21:
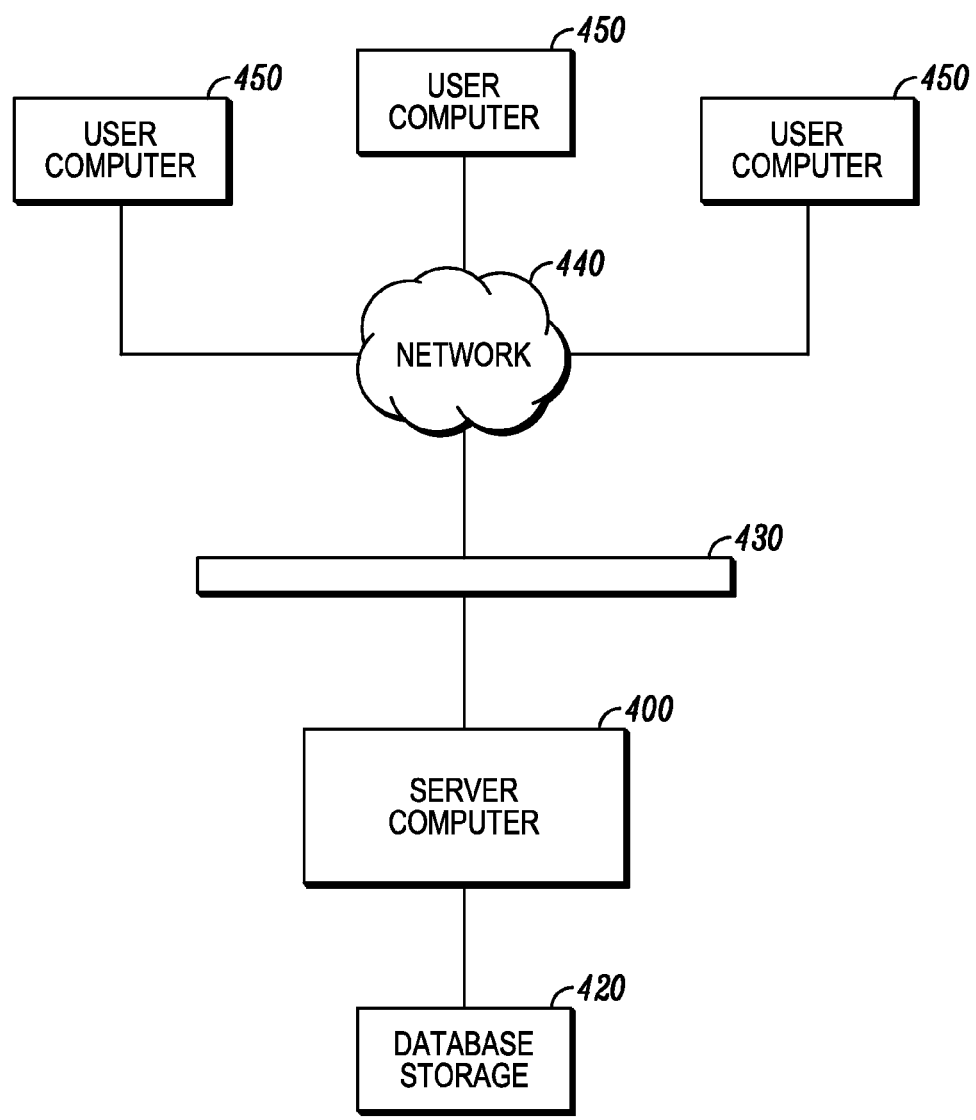
FIG. 21 is a block diagram of system for marketing products as disclosed herein.
Figure 22:
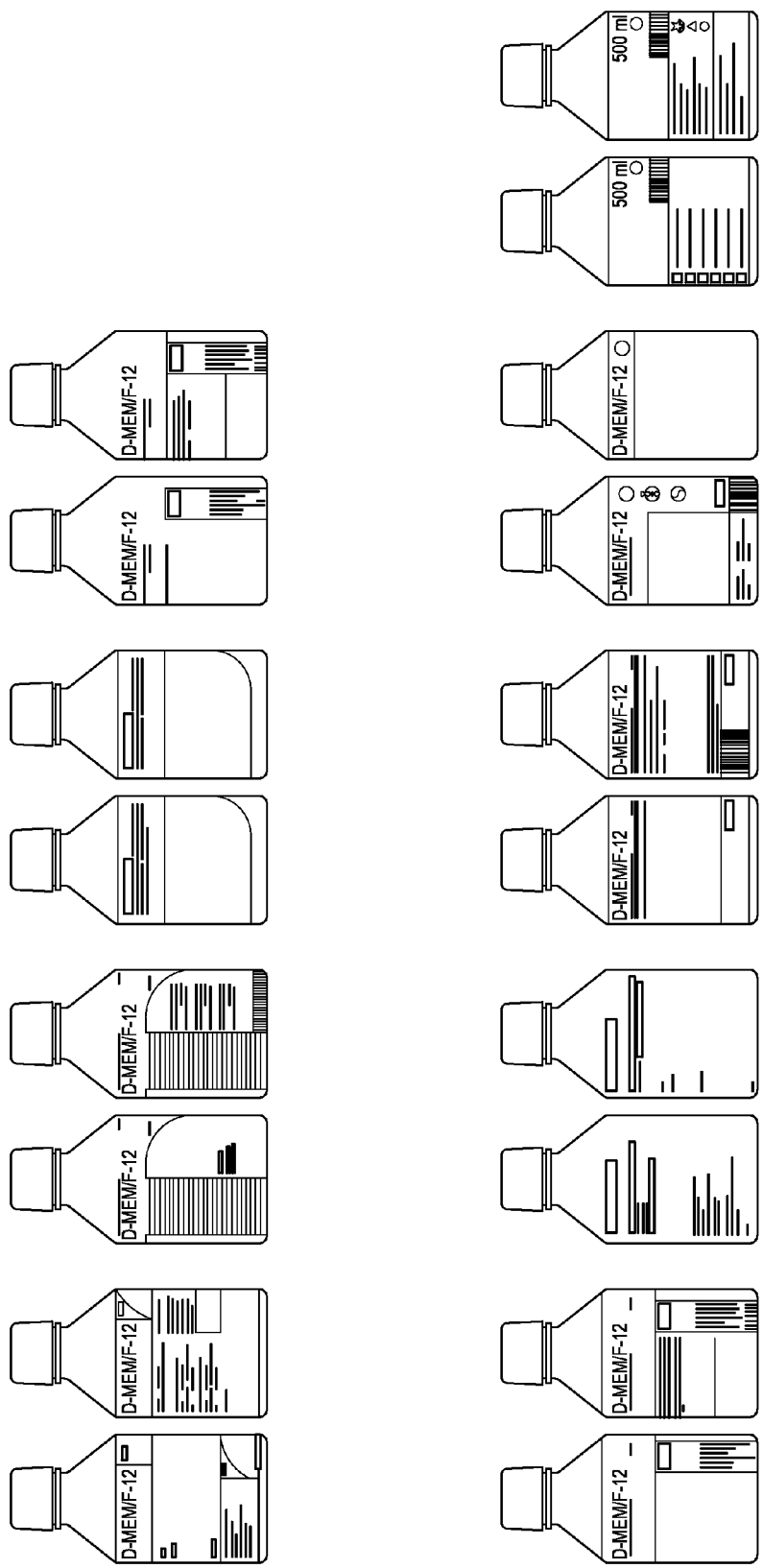
FIG. 22 shows various embodiments of labels as disclosed.
Figure 23:
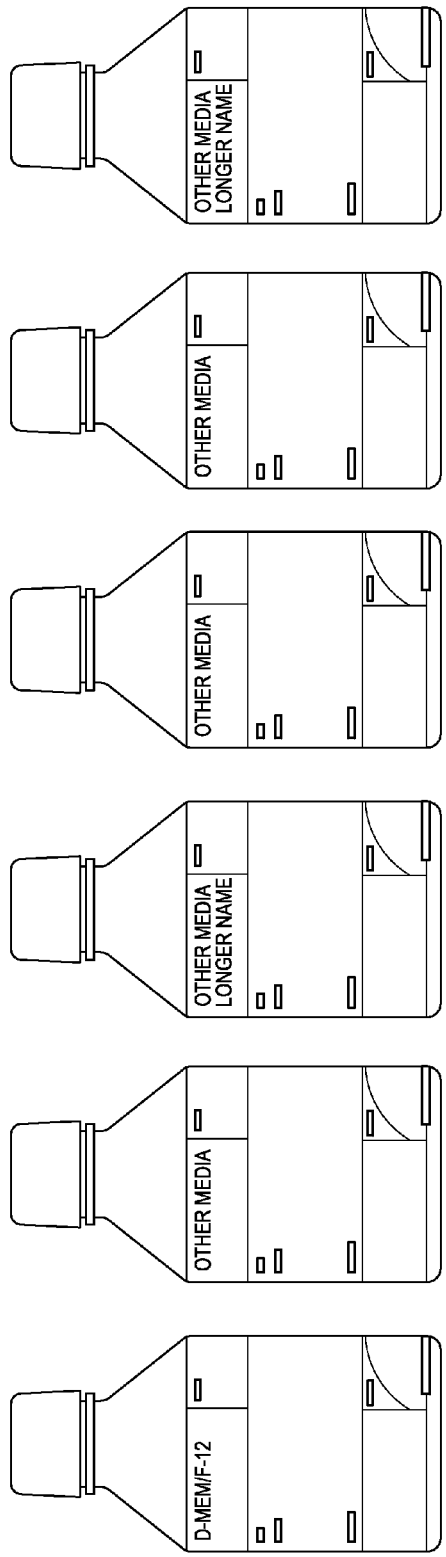
FIG. 23 is a more detailed view of labels as shown in FIG. 22.
Figure 24B:
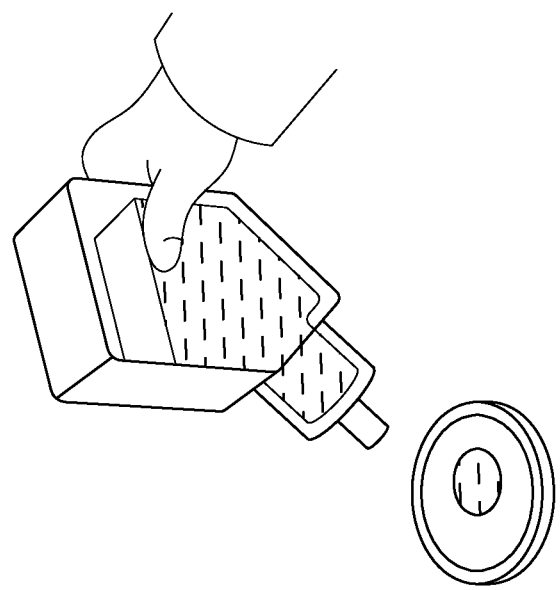
FIG. 24B is a perspective view of the container of FIG. 24A in use.
Figure 24A:
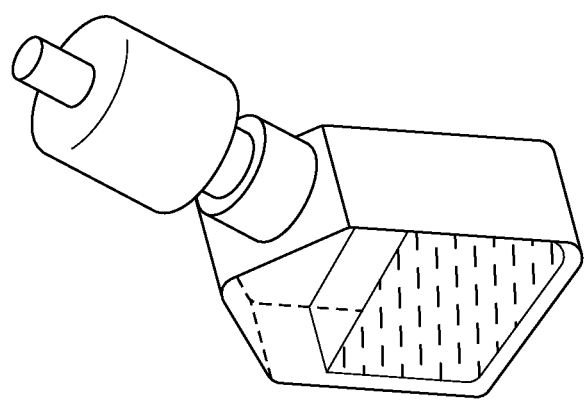
FIG. 24A is a perspective view of a bottle and attached dispenser.
Figure 25B:
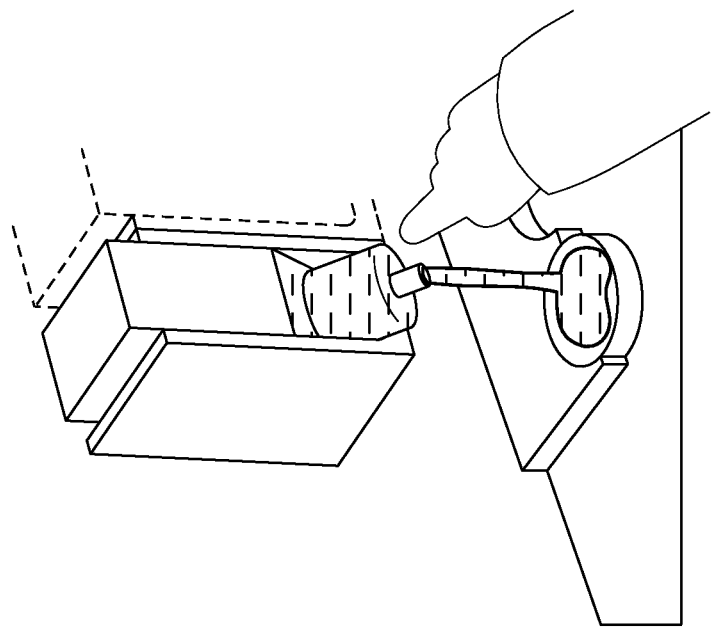
FIG. 25B is a perspective view of the embodiment of FIG. 25A in use.
Figure 25A:
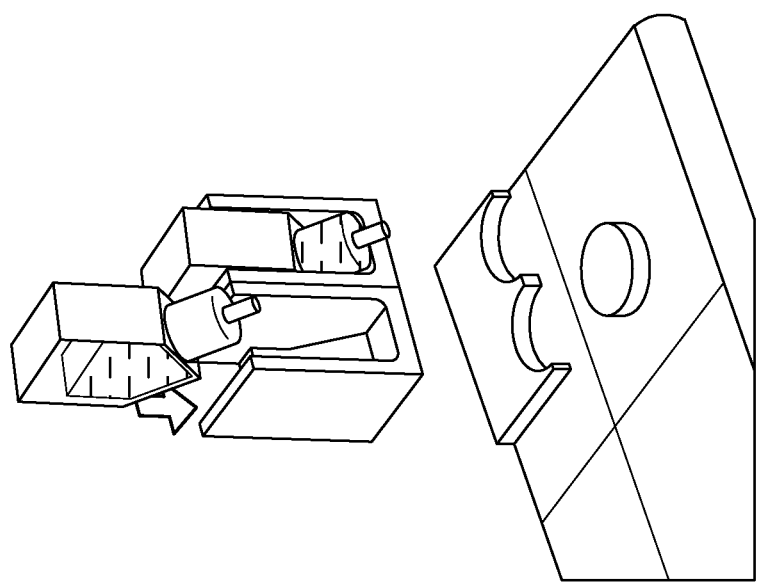
FIG. 25A is a perspective view of an embodiment of a dispensing station.

FIG. 20 provides a schematic diagram of an information-providing management system as encompassed within the present disclosure. In practice, the blocks in FIG. 20 can represent any organization which can be one legal entity or a combination of entities that provides products or systems as disclosed herein, which can include departments in a single building or in different buildings, a computer program or suite of programs maintained by one or more computers, a group of employees or contractors, a computer I/O device such as a printer or fax machine, a third party entity or company that is otherwise unaffiliated with the company, or the like.

The information-providing management system as shown in FIG. 20 is exemplified by organization 200, which makes, purchases, or otherwise makes available that organization 200 wishes to sell to interested parties. To this end, product descriptions 230 are made, providing information that would lead potential users to believe that products 220 can be useful to user or other acquirer. In order to effect transfer of product descriptions 230 to the potential users or other acquirers, product descriptions 230 are provided to advertising agency 240, which can be an entity separate from organization 200, or to advertising department 245, which can be an entity related to organization 200, for example, a subsidiary. Based on the product descriptions 230, advertisement 250 is generated and is provided to media accessible to potential purchasers of products 260, who may then contact organization 200 to purchase products 220.

By way of example, product descriptions 230 can be in a tangible form such as written descriptions, which can be delivered (e.g., mailed, couriered, etc.) to advertising agency 240 and/or advertising department 245, or can be in an intangible form such as entered into and stored in a database (e.g., on a computer, in an electronic media, etc.) and transmitted to advertising agency 240 and/or advertising department 245 over a telephone line, T1 line, wireless network, or the like. Similarly, advertisement 250 can be a tangible or intangible form such that it conveniently and effectively can be provided to potential parties of interest (e.g., potential purchasers of product 260). For example, advertisement 250 can be provided in printed form as flyers (e.g., at a meeting or other congregation of potential interested parties) or as printed pages (or portions thereof) in magazines known to be read by the potential interested parties (e.g., trade magazines, journals, newspapers, etc.). In addition, or alternatively, advertisement 250 can be provided in the form of directed mailing of computer media containing the advertisement (e.g., CDs, DVDs, floppy discs, etc.) or of e-mail (i.e., mail or e-mail that is sent only to selected parties, for example, parties known to members of an organization that includes or is likely to include potential users or other acquirers of products 220); of web pages (e.g., on a website provided by organization 200, or having links to the organization 200 website); or of pop-up or pop-under ads on web pages known to be visited by potential purchaser of products 260, and the like. Potential purchasers or other acquirers of products 260, upon being apprised of the availability of the products 220, can then contact organization 200 and, if so desired, can order said products 220 for organization 200 (see FIG. 19).

Also provided are methods for advertising which are designed to (1) result in increased sales, (2) to result in increased numbers of customers which use one or more products, and/or (3) to affect choices by potential customers which result in the selection of one product over another by the potential customers. These methods may include, for example, describing features of a product of the disclosure (e.g., a combination of (A) a reagent and (B) a container (1) with a label and/or (2) having features described elsewhere herein). In many instances, advertising methods of the disclosure will be in tangible form, such as flyers (e.g., brochures or cards suitable for mailing, posters presented at trade shows, etc.), newsletters, print advertisement in periodicals (e.g., newspapers, magazines, etc.).

The disclosure further includes advertisements themselves. Thus, the disclosure includes, for example, a composition comprising a full page or partial page advertisement in a magazine (e.g., a trade related magazine such as *Science, Biochemistry, The Journal of Molecular Biology, Virology*, etc.) in which features of products with one or more aspect of the disclosure are presented and/or compared to one or more additional products. These one or more additional products may be available from the same supplier, different suppliers, or the combination of the same supplier and one or more different suppliers. When a supplier of the products with one or more aspect of the disclosure provides a comparison with a product from the same supplier, the advertisement will often be designed to present new features of the products with one or more aspect of the disclosure to educate potential customers. In some instances, comparisons between different products will be in graphic form (e.g., photographs, charts, tables, etc.). One example of a type of table which could be used in advertisements is Table 1.

TABLE 1

| Percentage of Users with a Favorable Opinion | | | |
|---|---|---|---|
| Supplier/Product | Ergonomic Comfort | Label Feature(s) | Overall Product |
| Supplier 1/Product A | X | Y | Z |
| Supplier 1/Product B | X' | Y' | Z' |
| Supplier 1/Product C | X" | Y" | Z" |
| Supplier 2/Product D | X'" | Y'" | Z'" |
| Supplier 3/Product E | X"" | Y"" | Z"" |

The values X, Y, and Z may represent percentages. These data may also be shown as an average opinion of users based upon a scale of, for example, 1 to 10. Data such as standard deviation and user group size may also be included.

The disclosure also includes methods for performing comparative studies between products and/or product format (e.g., two products which each comprise a container with the same reagent but differing in label and/or container design). These comparative studies may include, for example, (1) providing one or more products with one or more aspects of the present disclosure to one or more sets of users (e.g., people who use products of the kind, such as laboratory bench scientists, etc.), (2) use of the provided product(s) by the users, (3) receiving data related to the opinion of users regarding the provided product(s), and optionally (4) assessing the data received to determine the results of the comparison. Comparative studies may or may not include providing and/or use of additional products (e.g., products to which products with one or more aspect of the disclosure are to be compared) by users who are to provide the data referred to above in step (3).

In many instances, it will not be necessary for users to actually use additional products at the same time as one or more products with one or more aspect of the disclosure. This is so because, for example, many users will be familiar with the additional products. Also, in instances where a comparative study is to be done with users who are not familiar with the additional products, a "blind" study can be performed. In other words, comparative studies can be performed by different users who each supply data related to different products. Using data from Table 1 as an example, one set of users may use Supplier 1/Product A. These users may then provide their opinions regarding ergonomic comfort, label feature(s), and the overall product, as well as other items. Similar data may be obtained from other users for other products (e.g., other products as set out in Table 1).

The disclosure also includes methods for increasing market share for particular product items or product categories. Examples of product items or product categories include particular reagents such as buffers (e.g., Tris-EDTA, pH 8.0), culture media, culture media components (e.g., fetal calf serum; concentrated solutions of amino acid, such as a 10× or 100× solution; etc.). In particular, methods of the disclosure include those in which products with one or more aspect of the disclosure (1) are brought to the attention of potential customers and (2) a particular percentage of the potential customers who previously purchased other products (i.e., products lacking some or all aspects of the disclosure) begin purchasing products with one or more aspect of the disclosure instead of the other products. The percentage of potential customers who switch from purchasing other products to purchasing products with one or more aspect of the disclosure may vary greatly but may be between 1% and 10%, 1% and 20%, 1% and 30%, 1% and 40%, 1% and 60%, 1% and 80%, 1% and 100%, 10% and 20%, 10% and 40%, 10% and 50%, 10% and 70%, 10% and 85%, 10% and 100%, 30% and 60%, 30% and 80%, 30% and 100%, 40% and 60%, 40% and 80%, 40% and 100%, 50% and 70%, 50% and 90%, 50% and 100%, etc. In some aspect, the percentage of potential customers who switch from purchasing other products to purchasing products with one or more aspect of the disclosure may be greater than 2%, greater than 5%, greater than 10%, greater than 20%, greater than 30%, greater than 40%, greater than 50%, greater than 65%, greater than 75%, greater than 85%, etc. The percentage of potential customers who switch form purchasing other products to products with one or more aspect of the disclosure may be determined by any means known in the art, and can be determined in certain embodiments by survey. In this method a representative number of users or former users of the products are asked to complete a survey with questions designed to determine the amount of use of the products prior to, and after having seen the advertisement. The number of customers or potential customers who have begun or stopped using any particular product or group of products can then be determined.

Another method for determining product acceptance and/or increase in market share is by, for example, the number of parties which switch from purchasing Product A in Table 1 to Product B. Since Products A and B are sold by the same Supplier, the Supplier will often have all of the information necessary to determine the number and/or percentage of parties who at one time point purchased Product A purchased Product B at another time point (e.g., a later time point).

Kits

In another aspect, the disclosure provides kits which may be used in conjunction with the products and method disclosed herein. The disclosure thus includes kits which contain products of the disclosure. Kits according to this aspect of the disclosure may comprise one or more containers, which may contain one or more reagent contained in one or more containers which contain one or more features of the disclosure.

Kits of the disclosure include kits for performing any number of processes (e.g., PCR, cell culture, molecular cloning, etc.). Depending on the function and/or functional aspects of the particular kit, the kit may contain one or more of the following components: (1) one or more nucleic acid molecule or vector, (2) one or more primer, (3) one or more polymerase, (4) one or more reverse transcriptases, (5) one or more buffers, (6) one or more detergent, (7) one or more transfection reagent, and/or (8) one or more culture medium. Additional items may also be included in the kits. Further, one or more kit components may comprise a container with one or more features described herein (e.g., the container may be a bottle with at least one feature described herein).

As noted above, one or more (e.g., one, two, three, four, five, eight, ten, fifteen, etc.) buffers may be supplied in kits. These buffers may be supplied at a working concentrations or may be supplied in concentrated form and then diluted to the working concentrations. These buffers often contain salt, metal ions, co-factors, metal ion chelating agents, etc. for the enhancement of activities of the stabilization of either the buffer itself or molecules in the buffer. Further, these buffers may be supplied in dried or aqueous forms. When buffers are supplied in a dried form, they are generally dissolved in water prior to use.

Kits may contain virtually any combination of the components set out above or described elsewhere herein. As one skilled in the art would recognize, the components supplied with kits vary with the intended use for the kits. Thus, kits may be designed to perform various functions set out in this application and the components of such kits vary accordingly. As a general rule, however, the components of a kit are enclosed in a container or box in close confinement for shipping and storage in a single container or box. The container may further contain technical information, instructions for use of the kit or any of its components, re-ordering information and/or information regarding related products.

It will be understood by one of ordinary skill in the relevant arts that other suitable modifications and adaptations to the methods and applications described herein are readily apparent from the descriptions contained herein in view of information known to the ordinarily skilled artisan, and may be made without departing from the scope or spirit of any embodiment thereof, or of the appended claims.

The following examples are included to demonstrate specific embodiments of the disclosure. It should be appreciated by those of skill in the art that the techniques disclosed in the examples which follow represent techniques discovered by the inventor to function well in the practice of the disclosure, and thus can be considered to constitute examples of modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

An example of a cellular growth media product that is marketed by catalog is Basal Medium Eagle (BME) (1×). The product, BME, which may be available in a 500 ml volume is in the Basal Media type or group of products and that type of product is indicated in this example by a lime green color. Within the basal media family or type are other media products such as BGJb medium, Brinster's BMOC-3 Medium, CMRL Medium, $CO_2$-Independent Medium, Cryopreservation Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM Zn++ Option (Richter's Modification), IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's Drosophila Medium, Waymouth's MB 752/1 Media, Williams Media E, media formulated for amniotic fluid cells, media formulated for chorionic villus samples, media formulated for peripheral blood lymphocytes, or media formulated for bone marrow cells, for example.

All members of the media type may be packaged in the same color code, lime green in this example. Each member of the family would also be associated with a simple number or numeric code such as a one to three digit number, for example. In the present example then, a product such as BME (1×) in a 500 ml volume may be associated with lime green 58. This product is then packaged in a bottle with a prominent lime green color region on the label, a matching prominent lime green color region on the cover, a prominent product identifier of 58 in lime green on the label, and a prominent product identifier of 58 in lime green on the cover. Thus lime green represents the color coded identifier for the media group or subgroup and 58 refers to BME (1×) in a 500 ml bottle. The label may contain additional information but need not necessarily have such information.

Alternatively, a subgroup of several media types may be grouped together and identified by a single color, and each member product within that group is identified by a number. For example, Minimal Essential Media is a sub-group of basal media that may be identified by a color red, for example. Individual products of Minimum Essential Media, may be identified by numbers. For example, Advanced MEM in a 500 ml bottle may be associated with number 35, and Advanced MEM sold in a package containing ten 500 ml bottles may be associated with number 37. Therefore a user or customer would indicate "red 35" to order the 500 ml bottle of Advanced MEM, rather than having to provide the catalog number, 12492-013, for example. This exemplifies the ease of ordering and recognition provided by the present disclosure.

EXAMPLE 2

In certain embodiments, various media subfamilies such as Dulbecco's Modified Eagle Medium DMEM may be identified by a separate color such as blue. In this case, various formulations and volumes of DMEM would be associated with individual numbers. For example, Dulbecco's Modified Eagle Medium (DMEM) (low glucose) (500 mL) may be packaged in a bottle with a prominent blue color region on the label, a matching prominent blue color region on the cover, a prominent product identifier of 120 in blue on the label, and a prominent product identifier of 120 in blue on the cover. Thus blue represents the color coded identifier for DMEM and 120 is the product identifier that can be used to refer to the specific medium in the DMEM class, here 500 mL bottles of low glucose DMEM. Again, the label may contain additional information but need not necessarily have such information.

EXAMPLE 3

An example of a product and package embodiment of the disclosure may be better understood by referring to FIGS. 8, 9 & 10. The following example is a microbiological liquid product packaged in an ergonomic container that has color coded labels and covers to identify the specific product. This system increases user efficiency and decreases the likelihood of contamination and spillage. In doing so, the system also decreases operating costs and the time required for the completion of research projects.

The bottle or container of this example is shown in front view in FIG. 8. The bottle has a rectangular footprint for efficient storage in rows in a refrigerator, on a shelf, or in a shipping container. The bottle also provides an angled top to provide angled access to the opening and also to provide an angled surface toward the rear for easily readable labeling. The features of the bottle include a cover 302 designed for easy one handed opening by including a ridge 304 for easy gripping. The ridge also serves as an indicator of the open or closed position of the cover, when combined with the embossed circle 306 on the bottle. This feature reduces the need for further contact with the bottle to check the position of the cover, as required with the traditionally round covers, reduces the likelihood that an open bottle will be picked up to be placed in storage, causing a spill, and reduces the likelihood that a bottle will be accidentally left open, thus risking contamination and the waste of product or worse, the loss of valuable cell cultures.

The top plane of the container shown in FIG. 8, that does not contain the opening, may functions as (1) a gripping surface to stabilize the bottle during removal of the cap, (2) a resting surface for the hand, and (3) an affordance to stabilize the bottle during pipetting of the fluid.

In many instances, containers of the invention (e.g., the container shown in FIG. 8) will be designed such that when a pipette is inserted perpendicular to the plane of the opening of the container, it points directly at the opposite corner of the container. The functional benefit of this is to allow retrieval of the last bit of fluid in the container. An additional benefit can be to decrease the amount of vertical motion that the user must employ in order to introduce the pipette into the opening. This imparts a substantial ergonomic benefit to the user, in that the user has a reduced need to raise his arm and the pipette above shoulder level. This may be important when containers of the invention are used under a flow hood.

It is a particularly advantageous aspect of this embodiment that the containers can be stored in one of two positions. The bottles can be placed in close proximity or in abutment in rows standing on the bottom surface thereof for a space saving arrangement. In this configuration the cover, any information on the cover, and the opening are available from the front, even for bottles that are not in the front row. The label information is also available from the rear as provided by the angled rear surface of the top as shown in FIG. 9. The containers can also be stacked on top of each other as shown in FIG. 10, while the cover and its information are still available even for the bottom rows. Another advantage to this design is that the bottles can be in either the vertical or horizontal position without having the liquid contents in contact with the cover, thus decreasing the probability for contamination. This storage versatility maximizes the user's ability to utilize space in incubators, hoods, refrigerators, and other storage chambers thereby increasing efficiency. Additionally, this allows users to store more materials in a smaller space ensuring that adequate supplies for experiments may be retained on-site without incurring prohibitive overhead capital and maintenance costs. The bottles have significantly less dead space when stored, as compared to the conventional media bottles shown in FIGS. 1 & 2.

As disclosed herein, optional protrusions and/or indentations allow for increased stability of containers when stacked. This added stability further decreases the risk of contamination or spilling, allows for increased efficiency through more sure movements under the hood, and encourages the efficient use of space by reducing the risk that containers will fall from stacked positions.

Unlike the conventional rounded bottle shown in FIG. 1, the relatively boxy shape of the example provides flat surfaces for marking and writing. When users attempt to write on rounded bottles the writing can often be messy or less legible thereby increasing the likelihood that a subsequent reading of the annotations will be difficult. This difficulty, in turn, makes it much more likely that mix ups will occur than if a bottle is clearly and legibly marked. The planar surfaces of the bottle also make manipulation of the bottle easier because it can rest on more than one surface, e.g., it doesn't have to sit on the bottom to be stable. The angled opening and neck of the bottle make pipetting easy compared to conventional bottles possessing an opening parallel with the bottom of the bottle, and in which a pipette must be raised straight up over the bottle for use, often requiring laboratory personnel to lean over the bench to reach the bottle, thus increasing the chance of an accidental spill or contamination. The exemplified bottle, in contrast, provides a 45 access so the worker can remain seated and simply reach over to the bottle at a more convenient angle. This bottle design thus reduces the required motion and range of movement for transferring liquids into and out of the bottle, reduces the chances for accidents or spills and increases operating efficiency for the user.

Furthermore, the angled neck of the bottle is also useful to increase efficiency by allowing users to quickly determine the contents of a bottle by providing instant identification of the contents by viewing the color coded cover. Unlike conventional bottles, the angled top bottle allows the user to view the top of the cover when the bottle is standing on the bottom surface or lying on the front surface in a stack of bottles, for example. By angling the neck of the bottle, the cover can always be positioned towards the observer, rather than towards the upper inside surface of the storage unit, and the contents of the bottle do not contact the cover in either configuration.

As shown in FIG. 8, for example, stripe 308 is in the coded color for this product group and printed within this stripe is the number identifier for this particular product. For example, if the product is a 500 mL bottle of low glucose DMEM as described in Example 2, the stripe would be blue and a number "120" would appear in the stripe. This blue stripe is continuous around three sides of the bottle and is easily visible from the rear as shown in FIG. 9. The number is optionally repeated on the side and back surface labels when the colored stripe is present. The label further provides an area 310 for other product information including the name of the product, the supplier's name, etc. This information is again repeated on the label 312 on the angled rear surface of the top for easy visual access. The label also provides further manufacturer or provider information such as lot number, catalog number, storage conditions, etc. on a lower portion 314 of the front label. The lower portion of the rear label 316 is optionally blank white space, convenient for user annotation.

It is a further aspect of the present example as described above, that the cover requires rotation of less than 360° and optionally only 90° to move from the closed, and sealed position to the open position. This feature is very beneficial in the laboratory setting in which often the bottle must be opened with one hand, and that hand often is already holding a pipetter or other liquid transfer mechanism. The interlocking portions of the interior of the cover and the exterior of the bottle neck have been designed in a manner such that a ninety degree rotation moves the cover from the closed and locked position to the open position. An example of such a locking mechanism is the luer fitting that is well know and widely used in the art of medical devices such as syringes and intravenous administrative tubing.

As described in the previous examples, the cover in this example is made of primarily white material so user annotation is easily seen and read. The cover also includes a label that includes a circular stripe 320 in the coded color, in this example blue and the number identifier in large type in the center 330 of the circle. Thus, the cover label would have a large 120 in blue surrounded by a blue circle. This identifies the product as "120 blue", or "blue 120." The color and number code identify a specific product and can be seen from arm's length, or from a distance of at least three feet by a person with normal vision. The user annotation space also allows users to differentiate between bottles of the same content type without sacrificing the ability to easily differentiate one content class from another by viewing the cover only.

The container shown in FIGS. 8 and 9 also contain a front angled, upper panel 340, a rear angled, upper panel 343, a right side panel 342, a left side panel 345, a front panel 341, a rear panel 344, and a base panel upon which the container rests (not numbered in FIGS. 8 and 9). Thus, the container shown in FIGS. 8 and 9 contain seven panels.

The labels in the present example thus are optionally opaque, two section labels, that may be a single label wrapped around the container or one or more separate labels affixed to the front and back surfaces of the container, and possibly to one side. The labels also prominently display the color code by a large colored stripe or colored area of the label and the product number, which allows the user to quickly identify the contents of a bottle by looking at the label. The color coding is present on both the front and back sections as a large region of color. This colored region allows identification of the contents of the bottle without requiring the user to handle the bottle, unlike conventional product labels. In addition, cross contamination between bottles with different classes of contents is reduced based on the common color coding of cover and label. If only the cover is color coded, once the cover is removed, it no longer identifies a particular bottle. As such, a user who removed the cover from two different bottles with different color codes would not know, without relying on memory, which cover belonged to which bottle. The labels in system solve this problem by coordinating the cover with the bottle.

In the embodiment described in this example, the labels can provide a large amount of blank space for user annotation and marking. This space allows the user to individually identify particular bottles with ease, describe additions to the contents, note the date the bottle was opened, and any other information that may be important without obscuring either the color or number code for the original contents. The rear section of the label has a limited amount of information on it to provide the user with the most space for marking. Critical information such as the product identifier, company logo, descriptive product name, and volume may appear on the front label in the colored region. The front label may contain more detailed text in addition to the information found on the back label including the specific product details, catalog reorder number, lot number, expiration date, temperature range, light sensitivity, and product warnings.

Figure 26A:
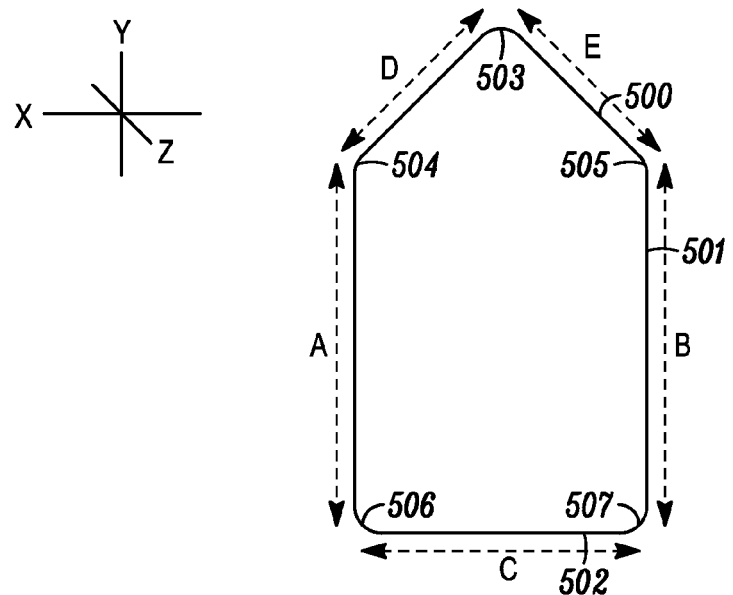
FIGS. 26A, 26B and 26C are various types of side panels (e.g., left and right side panels) which may be employed to form containers of the invention, such as a container as shown in FIGS. 8 and 9.
Figure 26B:
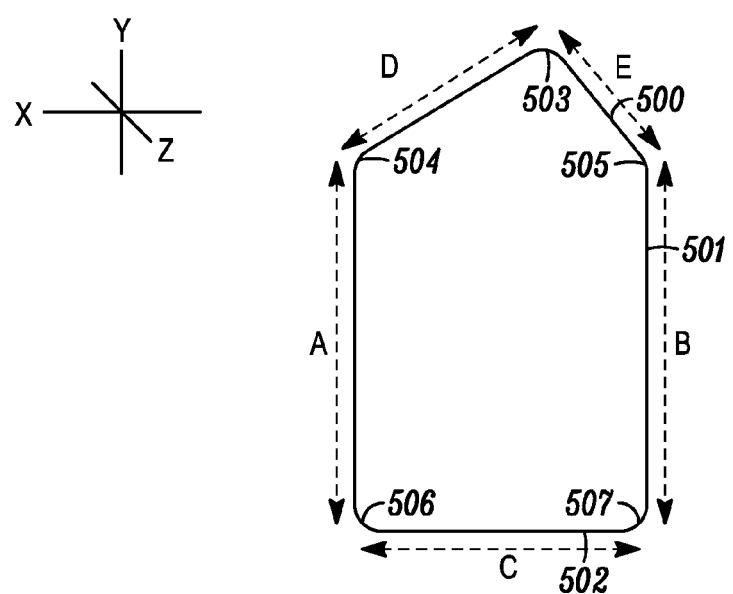
Figure 26C:
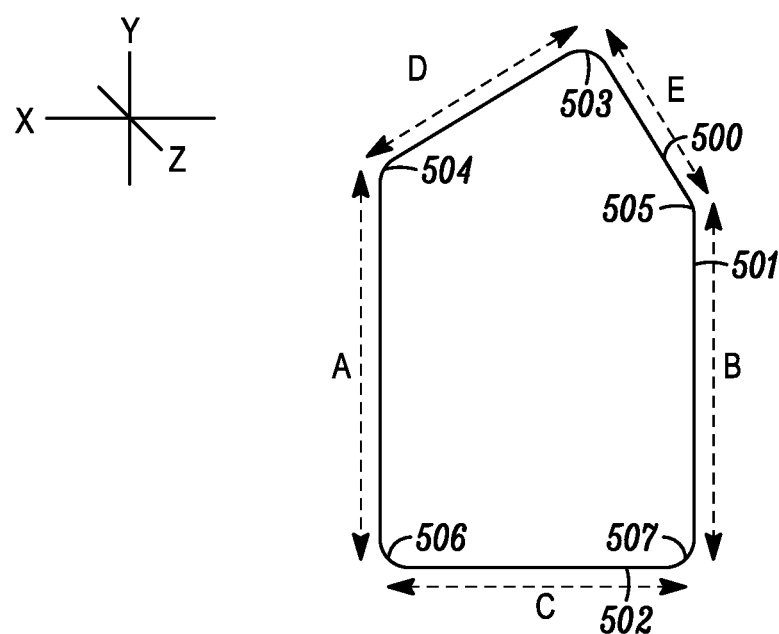

A side panel view of a container similar to that shown in FIGS. 8 and 9 is shown in FIG. 26A. Related embodiments are shown in FIGS. 26B and 26C. In FIGS. 26A, 26B and 26C, A, B, C, D, and E represent lengths and 503, 504, 505, 506, and 507 represent angles.

As one skilled in the art would recognize, container shape will change with changes in lengths A, B, C, D, and E and angles 503, 504, 505, 506, and 507. Lengths A and B, for example, may be the same or different. When lengths A and B are the same and are parallel to each other, then (1) angles 506 and 507 will typically total 180 degrees and (2) angles 503, 504, and 505 will typically total 180 degrees. Further, when 506 and 507 do not total 180 degrees, the total of the sum of angles 503, 504, and 505 will typically not equal 180 degrees. This is so because, as long as the side panel shown in FIG. 26A is flat (i.e., occupies the X and Y planes, with a straight line cross-section in the Z plane), the total of angles 503, 504, 505, 506, and 507 will be 360 degrees.

Often, angles 506 and 507 will total 180 degrees and each of these angles will be 90 degrees. Further, often, angles 503, 504, and 505 will total to 180 degrees and, in many instances, each of these angles will be 60 degrees. However, in some instances, angles 504 and 505 will be equal and these two angles will be different than angle 503. For example, angles 504 and 505 may each be 50 degrees and angle 503 may be 80 degrees. These angles will often influence the lengths D and E. In particular, in many instances, as angles 504 and 505 become larger, lengths D and E will often become longer.

In many instances, containers described herein will have at least one opening. This opening may be used for adding contents to or removing contents from the container. In FIGS. 8 and 9, an opening is shown in a panel which is in the Z plane along length D or E in FIGS. 26A and 26B. An opening, when present, may be present anywhere in the container. Typically, an opening will be present and will be located essentially as shown in FIGS. 8 and 9.

The lengths of A, B, C, D, and E may vary considerably. These variations in lengths will be determined by any number of factors including, for example, the intended use of the container, which will often be determined, at least in part, by the intended contents of the containers. Some factors which may determine the lengths of A, B, C, D, and E include (a) the required or desired stability of the container when positioned on the side having the length A, B, C, D, or E; (b) the interior volume the container; (c) the depth of the container in plane Z; and (d) the angle of an opening, when present.

Exemplary lengths of A, B, C, D, and E independently include from about 0.5 centimeters to about 50 centimeters, from about 1.0 centimeters to about 50 centimeters, from about 3.0 centimeters to about 50 centimeters, from about 5.0 centimeters to about 50 centimeters, from about 7.0 centimeters to about 50 centimeters, from about 10 centimeters to about 50 centimeters, from about 15 centimeters to about 50 centimeters, from about 20 centimeters to about 50 centimeters, from about 25 centimeters to about 50 centimeters, from about 0.5 centimeters to about 35 centimeters, from about 1 centimeters to about 35 centimeters, from about 5.0 centimeters to about 35 centimeters, from about 10 centimeters to about 35 centimeters, from about 15 centimeters to about 35 centimeters, from about 20 centimeters to about 35 centimeters, from about 25 centimeters to about 35 centimeters, from about 0.5 centimeters to about 25 centimeters, from about 1.0 centimeters to about 25 centimeters, from about 5.0 centimeters to about 25 centimeters, from about 7.0 centimeters to about 25 centimeters, from about 10 centimeters to about 25 centimeters, from about 15 centimeters to about 25 centimeters, etc.

While lengths A and B (side 501) in FIGS. 26A, 26B and 26C may be different, in many instances, lengths A and B will be the same or almost the same (e.g., the difference being less than about 2%). In many instances, when lengths A and B are the same, this will allow top containers to be readily stacked, as shown in FIG. 10. Thus, in many instances, the ratio of lengths A:B will be 1.0:1.0. However, the ratio of length A:B may be in the ranges of from about 1.0:0.25 to about 0.25:1.0, from about 1.0:0.5 to about 0.25:1.0, from about 1.0:0.25 to about 0.5:1.0, from about 1.0:1.0 to about 0.25:1.0, from about 1.0:0.25 to about 1.1:1.0, from about 1.0:0.75 to about 0.75:1.0, etc.

While lengths D and E in FIGS. 26A, 26B and 26C may be different, in many instances, lengths D and E will be the same or almost the same (e.g., the difference being less than about 2%). Thus, in many instances, the ratio of lengths D:E will be 1.0:1.0. However, the ratio of length D:E may be in the ranges of from about 1.0:0.25 to about 0.25:1.0, from about 1.0:0.5 to about 0.25:1.0, from about 1.0:0.25 to about 0.5:1.0, from about 1.0:1.0 to about 0.25:1.0, from about 1.0:0.25 to about 1.1:1.0, from about 1.0:0.75 to about 0.75:1.0, etc.

In instances where a container is positioned in manner in which the side having length A is positioned downward on a surface, an opening may be present on the side having length E. When this is the case, the angle of the opening on the side having length E may be adjusted by adjusting the sides having lengths B, D, and/or E (side 500). For example, when a container with a side panel as shown in FIG. 26A is rested on the base panel on a flat surface and angles 503, 504, and 505 are each 60 degrees, the angle of side E (and hence an opening on side E), will typically be about 45 degrees.

The lengths of sides B, D, and/or E and/or angles 503, 504, and/or 505 may be altered to change, for example, the angle of an opening, when present. The angle of an angled, upper panel (e.g., an angled, upper panel with an opening, such as panel 340) may be adjusted, for example, to minimize contact of the contents with this panel. For example, when a container of this type is positioned on a surface and rests upon back panel 344, as shown in FIG. 10, it may be desirable to minimize contact of the container's contents with panel 340. In such an instance, panel 340 may be "angled" away from the contents. This can be done when the opening is located in the panel adjacent to side E by lengthening side D.

Using a container such as that shown in FIGS. 8 and 9 and resting on the base panel for reference, containers of the invention include those in which panel 340 is positioned at an angle other than 45 degrees. Examples of such container are those which contain either one or two side panels as shown in FIGS. 26B and 26C. Exemplary angles for panel 340 are about 25 degrees, about 35 degrees, about 40 degrees, about 50 degrees, about 55 degrees, about 60 degrees, about 70 degrees, etc. Ranges of angles for panel 340 are between from about 25 degrees to about 70 degrees, from about 35 degrees to about 70 degrees, from about 45 degrees to about 70 degrees, from about 25 degrees to about 60 degrees, from about 25 degrees to about 50 degrees, from about 25 degrees to about 45 degrees, from about 25 degrees to about 44 degrees, from about 46 degrees to about 70 degrees, etc.

The length A in FIG. 26A, as well as in other embodiments of the invention, may be longer than, equal to, or shorter than the length C. The ratio of lengths A:C may, for example, be the following: about 0.5:1.0, about 1.0:1.0, about 1.5:1, about 2.0:1, about 2.5:1.0, about 3.0:1, about 3.5:1, etc. The ratio of lengths A:C may also be in the following ranges: from about 0.5:1.0 to about 3.5:1, from about 1.0:1.0 to about 3.5:1, from about 1.5:1.0 to about 3.5:1, from about 2.0:1.0 to about 3.5:1, from about 0.5:1.0 to about 2.5:1, from about 0.5:1.0 to about 2.5:1, from about 0.5:1.0 to about 2.0:1, from about 1.5:1.0 to about 2.5:1, etc. For example, when the length A is 10 centimeters and the length C is 5.0 centimeters, the ratio of A:C is 2.0:1.0.

In many instances, angles 506 and 507 will each be 90 degree angles (as shown in FIGS. 26A and 26B).

The total volume within a container having a side panel such as that shown in FIGS. 26A and 26B or a variation thereof (e.g., a variation described herein), will vary with a number of factors, such as lengths of the side lengths A, B, C (side 502), D, and E and angles 503, 504, 505, 506, and 507 and depth of the container in the Z plane. Exemplary container volumes are 25 milliliters, 75 milliliters, 100 milliliters, 125 milliliters, 150 milliliters, 200 milliliters, 250 milliliters, 300 milliliters, 350 milliliters, 400 milliliters, 450 milliliters, 500 milliliters, 600 milliliters, 700 milliliters, 800 milliliters, 850 milliliters, 900 milliliters, 1000 milliliters, 1500 milliliters, 2000 milliliters, 2500 milliliters, 3000 milliliters, 4000 milliliters, etc. Container of the invention may be designed to contain volumes in the ranges of from about 25 milliliters to about 5000 milliliters, from about 50 milliliters to about 5000 milliliters, from about 100 milliliters to about 5000 milliliters, from about 200 milliliters to about 5000 milliliters, from about 300 milliliters to about 5000 milliliters, from about 400 milliliters to about 5000 milliliters, from about 500 milliliters to about 5000 milliliters, from about 750 milliliters to about 5000 milliliters, from about 100 milliliters to about 5000 milliliters, from about 25 milliliters to about 4000 milliliters, from about 100 milliliters to about 4000 milliliters, from about 200 milliliters to about 4000 milliliters, from about 300 milliliters to about 4000 milliliters, from about 400 milliliters to about 4000 milliliters, from about 500 milliliters to about 4000 milliliters, from about 700 milliliters to about 4000 milliliters, from about 800 milliliters to about 4000 milliliters, from about 900 milliliters to about 4000 milliliters, from about 1000 milliliters to about 4000 milliliters, from about 25 milliliters to about 3000 milliliters, from about 100 milliliters to about 3000 milliliters, from about 200 milliliters to about 3000 milliliters, from about 300 milliliters to about 3000 milliliters, from about 400 milliliters to about 3000 milliliters, from about 500 milliliters to about 3000 milliliters, from about 600 milliliters to about 3000 milliliters, from about 700 milliliters to about 3000 milliliters, from about 800 milliliters to about 3000 milliliters, from about 900 milliliters to about 3000 milliliters, from about 1000 milliliters to about 3000 milliliters, from about 25 milliliters to about 2000 milliliters, from about 100 milliliters to about 2000 milliliters, from about 200 milliliters to about 2000 milliliters, from about 300 milliliters to about 2000 milliliters, from about 400 milliliters to about 2000 milliliters, from about 500 milliliters to about 2000 milliliters, from about 700 milliliters to about 2000 milliliters, from about 800 milliliters to about 2000 milliliters, from about 1000 milliliters to about 2000 milliliters, from about 25 milliliters to about 1500 milliliters, from about 100 milliliters to about 1500 milliliters, from about 200 milliliters to about 1500 milliliters, from about 300 milliliters to about 1500 milliliters, from about 400 milliliters to about 1500 milliliters, from about 500 milliliters to about 1500 milliliters, from about 700 milliliters to about 1500 milliliters, from about 900 milliliters to about 1500 milliliters, from about 100 milliliters to about 1500 milliliters, from about 25 milliliters to about 1000 milliliters, from about 100 milliliters to about 1000 milliliters, from about 200 milliliters to about 1000 milliliters, from about 300 milliliters to about 1000 milliliters, from about 400 milliliters to about 1000 milliliters, from about 500 milliliters to about 1000 milliliters, from about 600 milliliters to about 1000 milliliters, from about 700 milliliters to about 1000 milliliters, from about 25 milliliters to about 750 milliliters, from about 100 milliliters to about 750 milliliters, from about 200 milliliters to about 750 milliliters, etc.

Figure 27B:
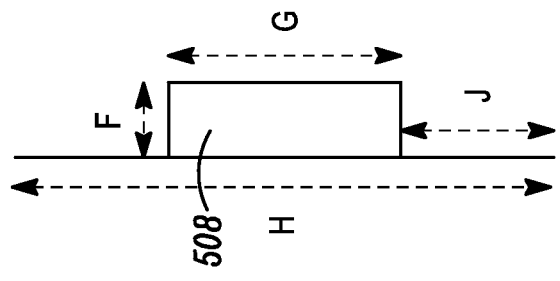
FIGS. 27A and 27B show two views (i.e., a frontal view and a side view, respectively) of an angled, upper panel of a container of the invention with an opening 508. One example of a container that could contain such a panel is shown in FIGS. 8 and 9 (e.g., the panel with cover 302 in FIG. 8).
Figure 27A:
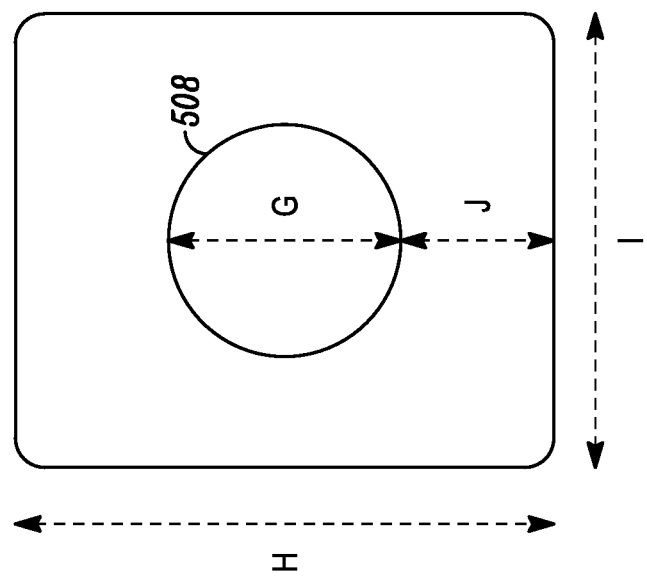

A panel of a container of the invention is shown in FIGS. 27A and 27B. The opening 508 has a size of length G and a depth of length F. Further, this panel may have a height of length H and a width of length I. Length H will often be the same or similar to length D and/or E of FIG. 26A, 26B, or 26C.

Opening 508 may be positioned anywhere on a panel on which it is present. Opening 508 may be centered in the middle of the panel or may be shifted higher than the center, lower than the center, or to the right or left of the center. For example, the H:J ratio (i.e., the ratio of the difference between the lengths H and J) may be about 10:1.0, about 8.0:1.0, about 7.0:1.0, about 5.0:1.0, about 3.5:1.0, about 3.0:1.0, about 2.5:1.0, about 2.0:1.0, about 1.8:1.0, about 1.5:1.0, about 1.3:1.0, about 1.2:1.0, about 1.1:1.0, etc. In many instances, when the length H is relatively small, as compared to the length J (e.g., the H:J ratio is close to 1.0:1.0, such as 1.3:1.0), the opening 508 will be close to the upper edge of the panel. In some instances, this may be advantageous because when, for example, the container is positioned as shown in FIG. 10, the closer opening 508 is to the upper edge of the panel, the less the contents of the container will contact the opening and any cover, when present.

Further, the size of opening 508 in relation to the panel may also vary widely. For example, opening 508 may take up about 25%, about 35%, about 45%, about 55%, about 65%, about 75%, about 85%, about 95%, etc. (e.g., between from about 20% to about 95%, between from about 30% to about 95%, between from about 40% to about 95%, between from about 50% to about 95%, between from about 60% to about 95%, between from about 70% to about 95%, between from about 20% to about 75%, between from about 20% to about 65%, between from about 20% to about 55%, between from about 20% to about 45%, between from about 30% to about 95%, between from about 35% to about 85%, between from about 35% to about 75%, between from about 40% to about 70%, etc.) of the total surface area of the panel.

All of the compositions and methods disclosed and claimed herein can be made and executed without undue experimentation in light of the present disclosure. While the compositions and methods of this disclosure have been described in terms of specific embodiments, it will be apparent to those of skill in the art that variations may be applied to the compositions and/or methods and in the steps or in the sequence of steps of the methods described herein without departing from the concept, spirit and scope of the inventions. More specifically, it will be apparent that related or similar agents or steps may be substituted for the agents or steps described herein while the same or similar results would be achieved. All such similar substitutions and modifications apparent to those skilled in the art are deemed to be within the spirit, scope and concept of the inventions as defined by the appended claims.

Each of the patent and non-patent documents referred to herein are hereby incorporated in their entirety.

The invention claimed is:

1. A container for storing animal serum, the container comprising:
   (i) a front panel and back panel, each of which is rectangular in shape and having a height to width ratio of between 1.0 to 1.0 and 3.5 to 1.0;
   (ii) two side panels each having five edges, wherein two of the edges are vertical edges which are parallel to each other, wherein one of the edges is a horizontal edge, the horizontal edge being located at the bottom of the panel, and two of the edges are angled, upper edges which each extend upward, each from different vertical edges, and meet to form an upside down V;
   (iii) a bottom panel which is rectangular in shape; and
   (iv) two angled, upper panels which are rectangular in shape;
   wherein the above panels are referred to with reference to the container resting on the bottom panel, and wherein at least one of the angled upper panels comprises an access port, wherein the height to width ratio is selected in such a way that a straight line passing through the access port can touch any point on the bottom panel when the container is resting on the bottom panel, and the straight line passing through the access port can touch any point on the back panel when the container is resting on the back panel, and wherein the straight line passing perpendicular to the plane of said access port can point directly at a corner formed by the interception of the back panel and the bottom panel.

2. The container of claim 1, wherein the serum is selected from the group consisting of adult bovine serum, fetal bovine serum, horse serum, newborn bovine calf serum, chicken serum, goat serum, lamb serum, porcine serum, and rabbit serum.

3. The container of claim 1, wherein the container comprises an inner volume selected from the group consisting of from about 125 milliliters to about 500 milliliters; from about 250 milliliters to about 1000 milliliters; and from about 250 milliliters to about 500 milliliters.

4. A container comprising:
   i. a bottom panel;
   ii. a front panel, a back panel, each having a height to width ratio of between 1.0 to 1.0 and 3.5 to 1.0;
   iii. a first side panel, and a second side panel;
   iv. a first top panel and an access port top panel; and
   v. an access port comprised within the access port top panel,
   wherein the height to width ratio is selected in such a way that a straight line passing through the access port can touch any point on the bottom panel when the container is resting on the bottom panel, and the straight line passing through the access port can touch any point on the back panel when the container is resting on the back panel, and wherein the straight line passing perpendicular to the plane of said access port can point directly at a corner formed by the interception of the back panel and the bottom panel.

5. The container of claim 4, wherein the container comprises a label which identifies the contents of the container.

6. The container of claim 4, wherein the opening is designed to accept a cover.

7. The container of claim 4, wherein the opening comprises a raised portion which is threaded.

8. The container of claim 6, wherein the cover can be removed by a rotational movement selected from the group consisting of less than 360°, less than 180° and approximately 90°.

9. The container of claim 8, wherein the cover provides a sterile seal.

10. The container of claim 9, wherein the cover comprises a label.

11. The container of claim 9, wherein the container comprises a label attached to one or more sides of the container, wherein a color is displayed on the label and the same color is displayed on the cover.

12. The container of claim 4, wherein the container comprises a top providing an angled opening, wherein the angled opening is facing upward at an angle when the container is standing on the base panel or lying on the front panel.

13. The container of claim 5, wherein the opening is covered by a cap, and wherein the top of the cap is facing upward at an angle when the container is standing on the bottom surface, lying on the front surface, or lying on the front surface with another container of the same shape stacked on top of the container and lying on the rear surface thereof.

14. The container of claim 4, wherein the container is a flat, stackable bottle comprising a label attached to a panel of (i) and/or (ii), wherein the label comprises an area for user labeling or annotation, wherein the area for user labeling or annotation is from about 40% to about 80% of the total area of the label.

15. The container of claim 4, wherein at least one of the panels of (i) or (ii) includes graduated volume markings.

16. The container of claim 4, wherein the container comprises an inner volume selected from the group consisting of from about 125 milliliters to about 500 milliliters; from about 250 milliliters to about 1000 milliliters; from about 250 milliliters to about 500 milliliters; and from about 600 milliliters to about 1250 milliliters.

17. The container of claim 4, wherein the container comprises cell culture medium is selected from the group consisting of base medium eagle (BME), BGJb medium, Basal Media Eagle (BME), Brinster's BMOC-3 Medium, CMRL Medium, CO2-Independent Medium, Cryopreservation Medium, Dulbecco's Modified Eagle Medium (D-MEM), F-10 Nutrient Mixtures, F-12 Nutrient Mixtures, Glasgow Minimum Essential Medium, Grace's Insect Cell Culture Medium, Improved MEM Zn++ Option (Richter's Modification), IPL-41 Insect Medium, Iscove's Modified Dulbecco's Medium, Leibovitz's L-15 Medium, McCoy's 5A Medium (modified), MCDB 131 Medium, Medium 199, Medium NCTC-109, Minimum Essential Medium (MEM), Modified Eagle Medium (MEM), Opti-MEM® I Reduced Serum Medium, RPMI Medium 1640, Schneider's Drosophila Medium, Waymouth's MB 752/1 Medium, and Williams Medium E.

* * * * *